(12) United States Patent
Walther et al.

(10) Patent No.: US 10,358,663 B2
(45) Date of Patent: *Jul. 23, 2019

(54) METHOD OF PRODUCTION OF 2,4-DIHYDROXYBUTYRIC ACID

(71) Applicant: ADISSEO FRANCE S.A.S., Antony (FR)

(72) Inventors: Thomas Walther, Lacroix-Falgarde (FR); Helene Cordier, Toulouse (FR); Christopher Topham, Toulouse (FR); Isabelle Andre, Toulouse (FR); Magali Remaud-Simeon, Ramonville (FR); Robert Huet, Paris (FR); Jean-Marie Francois, Toulouse (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/945,046

(22) Filed: Nov. 18, 2015

(65) Prior Publication Data

US 2016/0153013 A1 Jun. 2, 2016

Related U.S. Application Data

(63) Continuation of application No. 13/882,372, filed as application No. PCT/IB2011/002870 on Oct. 27, 2011, now Pat. No. 9,238,829.

(30) Foreign Application Priority Data

Oct. 28, 2010 (WO) .................. PCT/IB2010/003153
May 23, 2011 (WO) .................. PCT/IB2011/001559

(51) Int. Cl.
| | |
|---|---|
| C12P 7/42 | (2006.01) |
| C12N 9/02 | (2006.01) |
| C12N 9/04 | (2006.01) |
| C12N 9/12 | (2006.01) |
| C12P 9/00 | (2006.01) |
| C12P 7/40 | (2006.01) |
| C12N 1/21 | (2006.01) |
| C12N 15/53 | (2006.01) |
| C12N 15/54 | (2006.01) |
| C12N 15/70 | (2006.01) |
| C07F 9/09 | (2006.01) |

(52) U.S. Cl.
CPC .............. *C12P 7/42* (2013.01); *C07F 9/096* (2013.01); *C12N 9/0006* (2013.01); *C12N 9/0008* (2013.01); *C12N 9/1217* (2013.01); *C12N 15/70* (2013.01); *C12P 7/40* (2013.01); *C12P 9/00* (2013.01); *C12Y 101/01* (2013.01); *C12Y 102/01018* (2013.01); *C12Y 207/02004* (2013.01); *C12Y 102/01011* (2013.01)

(58) Field of Classification Search
None
See application file for complete search history.

(56) References Cited

U.S. PATENT DOCUMENTS

| | | |
|---|---|---|
| 5,932,453 A | 8/1999 | Kikuchi et al. |
| 6,040,160 A | 3/2000 | Kojima et al. |
| 2010/0120105 A1 | 5/2010 | Anthony et al. |

OTHER PUBLICATIONS

GenBank, Accession No. AP009048, asd gene, 2008, www.ncbi.nlm.nih.gov.*
Blanco et al., The role of substrate-binding groups in the mechanism of aspartate-beta-semialdehyde dehydrogenase, Act. Cryst., 2004, D60, 1388-95.*
pET System Manual, 2003, Novagen.*
Uniprot, Accession No. P44801, 2009, www.uniprot.org.*
Uniprot, Accession No. A4YGN0, 2009, www.uniprot.org.*
Mendel, Site-Directed Mutagenesis With an Expanded Genetic Code, Annu. Rev. Biophys. Biomol. Struct., 1995, 24, 435-62.*
Uniprot, Accession No. P0A9Q9, 2009, www.uniprot.org.*
GenBank, Accession No. AP009048, IysC gene, 2008, www.ncbi.nlm.nih.gov.*
Kikuchi et al., Mutational analysis of the feedback sites of lysine-sensitive aspartokinase of *Escherichia coli*, FEMS Microbiol. Lett., 1999, 173, 211-15.*
GenBank, Accession No. L42023.1, 2009, www.ncbi.nlm.nih.gov.*
Marco-Marin et al., "Site-Directed Mutagenesis of *Escherichia coli* Acetylglutamate Kinase and Aspartokinase III Probes the Catalytic and Substrate-Binding Mechanisms of these Amino Acid Kinase Family Enzymes and Allows Three-Dimensional Modelling of Aspartokinase," J. Mol. Biol., vol. 334, pp. 459-476, 2003.
Ouyang et al., "Use of Structural Comparisons to Select Mutagenic Targets in Aspartate-?-semialdehyde Dehydrogenase," Biochemistry, vol. 34, pp. 6394-6399, 1995.
Hadfield et al., "Active Site Analysis of the Potential Antimicrobial Target Aspartate Semialdehyde Dehydrogenase," Biochemistry, vol. 40, pp. 14475-14483, 2001.
Kockelkorn et al., "Malonic Semialdehyde Reductase, Succinic Semialdehyde Reductase, and Succinyl-Coenzyme A Reductase from Metallosphaera sedula: Enzymes of the Autotrophic 3-Hydroxypropionate/4-Hydroxybutyrate Cycle in Sulfolobales," Journal of Bacteriology, vol. 191, No. 30, pp. 6352-6362, Oct. 2009.
DeLaBarre et al., "Crystal Structures of Homoserine Dehydrogenase Suggest a Novel Catalytic Mechanism for Oxidoreductases," Nature Structural Biology, vol. 7, No. 3, pp. 238-244, Mar. 2000.
Priess et al., "Cloning of the Aspartate-?-Semialdehyde Dehydrogenase Structural Gene from *Escherichia coli* K12," Current Microbiology, vol. 7, pp. 263-268, 1982.
Mar. 20, 2012 International Search Report issued in International Application No. PCT/IB2011/002870.

(Continued)

*Primary Examiner* — Robert B Mondesi
*Assistant Examiner* — Todd M Epstein
(74) *Attorney, Agent, or Firm* — Oliff PLC

(57) ABSTRACT

A method of producing 2,4-dihydroxybutyric acid (2,4-DHB) by a synthetic pathway that includes transforming malate into 4-phospho-malate using a malate kinase, then transforming 4-phospho-malate into malate-4-semialdehyde using a malate semialdehyde dehydrogenase, and then transforming malate-4-semialdehyde into 2,4-DHB using a DHB dehydrogenase.

41 Claims, 7 Drawing Sheets

Specification includes a Sequence Listing.

(56) References Cited

OTHER PUBLICATIONS

Apr. 30, 2013 International Preliminary Report on Patentability issued in International Application No. PCT/IB2011/002870.
UniProt, Accession No. P08660, 2009, www.uniprot.org.

* cited by examiner

```
Ec_AKIII   ------------------------------------------------------------
Ec_AKI     ------------------------------------------------------------
Ec_AKII    ------------------------------------------------------------
Mj         ------------------------------------------------------------
Tt         ------------------------------------------------------------
Cg         ------------------------------------------------------------
At         MAATRVRCCHSNAAFTRLPLTRHRNSPTLPISLNRVDFPTLKKLSLPIGDGSSIRKVSGS  60
Sc         ------------------------------------------------------------

Ec_AKIII   ------------------------MSEIVVSKFGGTSVADF------DAMNRSADIVLSDA  31
Ec_AKI     -----MKNLRLCRRIFISTKGNEVTTMRVLKFGGTSVANA------ERFLRVADILESNA  49
Ec_AKII    ---------------MSVIAQAGAKGRQLHKFGGSSLADV------KCYLRVAGIMAEYS  39
Mj         ------------------MTTVMKFGGTSVGSG--ERIRHVAKIVTKRKKEDD  33
Tt         -----------------------MALVVQKYGGTSVGDL--ERIHKVAQRIAHYREKGH  34
Cg         -----------------------MALVVQKYGGSSLESA--ERIRNVAERIVATKKAGN  34
At         GSRNIVRAVLEEKKTEAITEVDEKGITCVMKFGGSSVASA------ERMKEVADLILTFP 114
Sc         --------------MPMDFQPTSSHSNWVVQKFGGTSVGKFPVQIVDDIVKHYSKPDGPNN  47
                          : *;**;*;  ,

Ec_AKIII   NVRLVVLSASAGITN--LLVALAEGLEPGER-FEKLDAIRNIQFAILERLRYPNVIR---  85
Ec_AKI     RQGQVATVLSAPAKITNHLVAMIEKTISGQDALPNISDAERIFAELLTGLAAAQPGFP-L 108
Ec_AKII    QPDDMMVVSAAGSTTNQLINWLKLSQTDRLSAHQVQQTLRRYQCDLISGLLPAEEADS--  97
Mj         DVVVVVSAMSEVTNALVEISQQALDVRDIAKVG---DFIKFIREKHYKAIEEAIKSEEIK  90
Tt         RLAVVVSAMGHTTDELIALAKRVNPR-----------------------------------  60
Cg         DVVVVVCSAMGDTTDELLELAAAVNPV----------------------------------  60
At         RESPVIVLSAMGKTTNNLLLAGEKAVSCGVSNASEIEELSIIKELHIRTVKELNIDP--- 171
Sc         NVAVVCSARSSYTKABGTTSRLLKCCDLASQESEFQDIIEVIRQDHIDNADRFILNPALQ 107
              :           ,

Ec_AKIII   ----EEIERLLENITVLAEAAALATSPALT--DELVSHGELMSTLLFVEILRERDVQAQW 139
Ec_AKI     AQLKTFVDQEFAQIKHVLHGISLLGQCPDSINAALICRGEKMSIAIMAGVLEARGHNVTV 168
Ec_AKII    -------LISAFVSDLERLAALLDSGINDAVYAEVVGHGEVWSARLMSAVLNQQGLPAAW 150
Mj         EEVKKIIDSRIEELEKVLIGVAYLGELTPKSRDYTLSFGERLSSPILSGAIRDLGEKSIA 150
Tt         -------------------PPFRELDLLTTTGEQVSVALLSMQLWAMGIPAKG  94
Cg         --------------PPAREMDMLLTAGERISNALVAMAIESLGAEAQS  94
At         ----SVILTYLEELEQLLKGIAMMKELTLRTRDYLVSFGECLSTRIFAAYLNTIGVKARQ 227
Sc         AKLVDDTNKELELVKKYLNASKVLGEVSSRTVDLVMSCGEKLSCLFMTALCNDRGCKAKY 167
                                :   **  *  :.

Ec_AKIII   FDVRKV---MRTNDRFGRAEPDIAALAELAALQLLPRLN-EGLVITQGFIGS-ENKGRTT 194
Ec_AKI     IDPVEKL------LAVGHYLESTVDIAESTRRIAASRIPADHMVLMAGFTAG-NEKGELV 221
Ec_AKII    LDAREFLR------AERAAQPQVDEGLSYPLLQQLLVQHPGKRLVVTGFISR-NNAGETV 203
Mj         LEGGEAG------IITDMNPGSARVKRLEVKERLLPLLKEGIIPVVTGFIGT-TEEGYIT 203
Tt         FVQHQIG-------ITTDGRYGDARILEVNPARIREALDQGFVAVIAGFMGTTPEG-EIT 146
Cg         FTGSQAG------VLTTERHGNARIVDVTPGRVREALDEGKICIVAGFQGVNKETRDVT 147
At         YDAFEIG--FITTDDFTNGDILEATYPAVAKRLYDDWMHDPAVPIVTGFLGKGWKTGAVT 285
Sc         VDLSHIVPSDFSASALDNSFYTFLVQALKEKLAPFVSAKERIVPVFTGFFGL-VPTGLLN 226
                            ** .

Ec_AKIII   TLGRGGSDYTAALLAEALHASRVDIWTDVPGIYTTDPRVVSAAKRIDEIAFAEAAEMATF 254
Ec_AKI     VLGRNGSDYSAAVLAACLRADCCEIWTDVDGVYTCDPRQVPDARLLKSMSYQEAMELSYF 281
Ec_AKII    LLGRNGSDYSATQIGALAGVSRVTIWSDVAGVYSADPRKVKDACLLPLLRLDEASELARL 263
Mj         TLGRGGSDYSAALIGYGLDADIIEIWTDVSGVYTTDPRLVPTARRIPKLSYIEAMELAYF 263
Tt         TLGRGGSDTTAVAIAAALGAKECEIYTDTEGVYTTDPHLIPEARKLSVIGYDQMLEMAAL 206
Cg         TLGRGGSDTTAVALAAALNADVCEIYSDVDGVYTADPRIVPNAQKLEKLSFEEMLELAAV 207
At         TLGRGGSDLTATTIGKALGLKEIQVWKDVDGVLTCDPTIYKRATPVPYLTFDEAAELAYF 345
Sc         GVGRGYTDLCAALIAVAVNADELQVWKEVDGIFTADPRKVPEARLLDSVTPEEASELTYY 286
             **, :*   *, :.      - ::.:. *:  : **   *  ;  :  *::

Ec_AKIII   GAKVLHPATLLPAVRSDIPVFVGSSKDPRAGGTLVCN------------------K 292
Ec_AKI     GAKVLHPRTITPIAQFQIPCLIKNTGNPAPGTLIGAS------------------R 320
Ec_AKII    AAPVLHARTLQPVSGSEIDLQLRCSYTPDQGSTRIERV------------------- 301
Mj         GAKVLHPRTIEPAMEKGIPILVKNTFEPESEGTLITND------------------M 302
Tt         GARVLHPRAVYYAKRYGVVLHVRSSFS-YNPGTLVKEV------------------AM 245
Cg         GSKILVLRSVEYARAFNVPLRVRSSYS-NDPGTLIAGS------------------ME 246
At         GAQVLHPQSMRPAREGEIPVRVKNSYNPKAPGTIITKT------------------R 384
Sc         GSEVIHPFTMEQVIRAKIPIRIKNVQNPLGNGTIIYPDNVAKKGESTPPHPPENLSSSFY 346
            .:  ::    ::         :    :      .*  :
```

Figure 2A

```
Ec_AKIII   TENPPLFRALALRRNQTLLTLHSLNMLHSRGFLAEVFGILARHNISVDLITTSEVSVALT  352
Ec_AKI     DEDELPVKGISNLNNMAMFSVSGPGMKGMVGMAARVFAAMSRARISVVLITQSSSEYSIS  380
Ec_AKII    LASGTGARIVTSHDDVCLIEFQVPASQDFKLAHKEIDQILKRAQVRPLAVGVHNDRQLLQ  361
Mj         EMSDSIVKAISTIKNVALINIFGAGMVGVSGTAARIFKALGEEEVNVILISQGSSETNIS  362
Tt         EM---DKAVTGVALDLDHAQIGLIGIPDQPGIAAKVFQALAERGIAVDMIIQGVPGHDPS  302
Cg         DIPVEEAVLTGVATDKSEAKVTVLGISDKPGEAAKVFRALADAEINIDMVLQNVSSVEDG  306
At         DMTKSILTSIVLKRNVTMLDIASTRMLGQVGFLAKVFSIFEELGISVDVVATSEVSISLT  444
Sc         EKRKRGATAITTKNDIFVINIHSNKKTLSHGFLAQIFTILDKYKLVVDLISTSEVHVSMA  406
                   :   ,        .:  :    :     :

Ec_AKIII   LDTTGSTS-TGDTLLTQSLLMELSA-------LCRVEVEEGLALVALIGNDLSKACGVG-  403
Ec_AKI     FCVPQSDCVRAERAMQEEFYLELKEG-----LLEPLAVTERLAIISVVGDGMRTLRGISA  435
Ec_AKII    FCYTSEVADSALKILDEAGLPGELR-----------LRQGLALVAMVGAGVTRNPLHCH  409
Mj         LVVSEEDVDKALKALKREFGDFGKKSFLNNNLIRDVSVDKDVCVISVVGAGMRGAKGIAG  422
Tt         RQQMAFTVKKDFAQEALEALEPVLAEIG----GEAILRPD-IAKVSIVGVGLASTPEVPA  357
Cg         TTDITFTCPRSDGRRAMEILKKLQVQGN----WTNVLYDDQVGKVSLVGAGMKSHPGVTA  362
At         LDPSKLWSRELIQQELDHVVEELEK-------IAVVNLLKGRAIISLIGNVQHSSLILE-  496
Sc         LPIPDADSLKSLRQAEEKLRILG------------SVDITKKLSIVSLVGKHMKQYIGIAG  455
                                         .   ::::*

Ec_AKIII   KEVFGVLEP-FNIRMICYGASSHNLCFLVPGEDAEQVVQKLHSNLFE-------------  449
Ec_AKI     KFFAALARANINIVAIAQGSSERSISVVVNNDDATTGVRVTHQMLFNTDQVIEVFVIGVG  495
Ec_AKII    RFWQQLKGQPVEFTWQS--DDGISLVAVLRTGPTESLIQGLHQSVFRAEKRIGLVLFGKG  467
Mj         KIFTAVSESGANIKMIAQGSSEVNISFVIDEKDLLNCVRKLHEKFIEKTNS---------  473
Tt         KMFQAVASTGANIEMIA--TSEVRISVIIPAEYAEAALRAVHQAFEL---DKA-------  405
Cg         EFMEALRDVNVNIELIS--TSEIRISVLIREDDLDAAARALHEQFQLGGEDEAVVYAGTG  420
At         RAPHVLYTKGVNVQMISQGASKVNISFIVNEAEAEGCVQALHKSFFESGDLSELLIQPRL  556
Sc         TMFTTLAEEGINIEMISQGANEINISCVINESDSIKALQCIHAKLLSERTNTSNQFEHAI  515
                  :  !.  ,  .   :  ::      :  *  .

Ec_AKIII   ------------------------------------------------------------
Ec_AKI     GVGGALLEQLKRQQSWLKNKH-IDLRVCGVANSKALLTNVHGLNLENWQEELAQAKEPFN  554
Ec_AKII    NIGSRWLELFAREQSTLSARTGFEFVLAGVVDSRRSLLSYDGLDASRALAFFNDEAVEQD  527
Mj         ------------------------------------------------------------
Tt         ------------------------------------------------------------
Cg         ------------------------------------------------------------
At         GNGSPVRTLQVEN-----------------------------------------------  569
Sc         DERLEQLKRLGI------------------------------------------------  527

Ec_AKIII   ------------------------------------------------------------
Ec_AKI     LGRLIRLVKEYHLLNPVIVDCTSSQAVADQYADFLREGFHVVTPNKKANTSSMDYYHQLR  614
Ec_AKII    EESLFLWMRAHPYDDLVVLDVTASQQLADQYLDFASHGFHVISANKLAGASDSNKYRQIH  587
Mj         ------------------------------------------------------------
Tt         ------------------------------------------------------------
Cg         ------------------------------------------------------------
At         ------------------------------------------------------------
Sc         ------------------------------------------------------------

Ec_AKIII   ------------------------------------------------------------
Ec_AKI     YAAEKSRRKFLYDTNVGAGLPVIENLQNLLNAGDELMKFSGILSGSLSYIFGKLDEGMSF  674
Ec_AKII    DAFEKTGRHWLYNATVGAGLPINHTVRDLIDSGDTILSISGIFSGTLSWLFLQFDGSVPF  647
Mj         ------------------------------------------------------------
Tt         ------------------------------------------------------------
Cg         ------------------------------------------------------------
At         ------------------------------------------------------------
Sc         ------------------------------------------------------------

Ec_AKIII   ------------------------------------------------------------
Ec_AKI     SEATTLAREMGYTEPDPRDDLSGMDVARKLLILARETGRELELADIEIEPVLPAEFNAEG  734
Ec_AKII    TELVDQAWQQGLTEPDPRDDLSGKDVMRKLVILAREAGYNIEPDQVRVESLVPAHCEG-G  706
Mj         ------------------------------------------------------------
Tt         ------------------------------------------------------------
Cg         ------------------------------------------------------------
At         ------------------------------------------------------------
Sc         ------------------------------------------------------------
```

Figure 2B

```
Ec_AKIII    ---------------------------------------------------------
Ec_AKI      DVAAFMANLSQLDNLFAARVAKARDEGKVLRYVGNIDEDGVCRVKIAEVDSNDPLFKVKN 794
Ec_AKII     SIDHFFENGDELNEQMVQRLEAAREMGLVLRYVARFDANGKARVGVEAVREDHPLASLLP 766
Mj          ---------------------------------------------------------
Tt          ---------------------------------------------------------
Cg          ---------------------------------------------------------
At          ---------------------------------------------------------
Sc          ---------------------------------------------------------

Ec_AKIII    -------------------------------------------
Ec_AKI      GENALAFYSHYYQPLPLVLRGYGAGNDVTAAGVFADLLRTLSWKLGV 841
Ec_AKII     CDNVFAIESRWYRDNPLVIRGPGAGRDVTAGAIQSDINRLAQLL--- 810
Mj          -------------------------------------------
Tt          -------------------------------------------
Cg          -------------------------------------------
At          -------------------------------------------
Sc          -------------------------------------------
```

Figure 2C

```
Ec        --------MKNVGFIGWRGMVGSVLMQRMVEERDFDAIRPVFFSTSQLGQAAPSFGGTTGT  53
Sc        MAG-----KKIAGVLGATGSVGQRFIL-LLAN-HPHFELKVLGASSRSAGKKYVDAVNWKQ  54
Cg        --------MTTIAVVGATGQVGQVMRT-LLEERNFPADTVRFFASPRSAGRKIEFRGTEIE  52
Bs        ----MGRGLHVAVVGATGAVGQQMLK-TLEDRNFEMDTLTLLSSKRSAGTKVTFKGQELT   55
At        -----ESAPSLAVVGVTGAVGQEFLS-VLSDRDFPYSSIKMLASKRSAGKRVAFDGHEYT  54
Tt        --------MRVAVVGATGAVGREILK-VLEARDFPLSDLRLYASPRSAGVRLAFRGEEIP  51
Mj        MSKGEKMKIKVGVLGATGSVGQRFVQ-LLAD-HPMFELTALAASERSAGKKYKDACYWFQ  58
                    ..:*  * **    :      :  ::  :.

Ec        LQDAFD-------------LEALKALDIIVTCQGGDYTNEIYPKLRESGWQGYWIDAASS  100
Sc        TDLLPESATDIIVS--ECKSEFFKECDIVFSGLDADYAGAIEKEFMEAG--IATVSNAKN  110
Cg        VEDITQ----------ATEESLKDIDVALFSAGGTASKQYAPLFAAAG--ATVVDNSSA  99
Bs        VQEAS-----------PESFEGVNIALFSAGGSVSQALAPEAVKRG--AIVIDNTSA    99
At        VEELT-------------ADSFNGVDIALFSAGGSISKEFGPLAAEKG--TIVVDNSSA  98
Tt        VEPLP-------------EGPLP-VDLVLASAGGGISKAKALVWAEGG--ALVVDNSSA  94
Mj        DRDIPENIKDMVVIPTDPKHEEFEDVDIVFSALPSDLAKKFEPEFAKEG--KLIFSNASA  116
                   :  ::  .     . :        *   .. :.

Ec        LRMKDDAIIILDPVNQD---VITDGLNNG---------IRTFVGGNCTVSLMLMSLGGLF  148
Sc        YRREQDVPLIVPVVNPEHLDIVAQKLDTAKAQGKPRPGF-IICISNCSTAGLVAPLKPLI  169
Cg        WRKDDEVPLIVSEVNPSD----KDSLVKG---------IIANPNCTTMAAMPVLKPLH  144
Bs        FRMDENTPLVVPEVNEA-----DLHEHNG---------IIANPNCSTIQMVAALEPIR  143
At        FRMVDGVPLVIPEVNPEAMKGIKVGMGKG---------ALIANPNCSTIICLMAVTPLH  148
Tt        WRYEPWVPLVVPEVNRE-----KIFQHRG---------IIANPNCTTAILAMALWPLH  138
Mj        YRMEEDVPLVIPEVNADHLELIEIQREKRGWDG-----A-IITNPNCSTICAVITLKPIM  170
          *     . :::  **                       :   **:.         :  :

Ec        ANDL-VDWVSVATYQAASGGGARHMRELLTQMGHLYGHVADELATPSSAILDIERKVTTL  207
Sc        EKFGPIDALTTTTLQAISGAGFSPGVPGIDILDNI-----------------------  204
Cg        DAAG-LVKLHVSSYQAVSGSGLAGVETLAKQVAAVGDHNVEFVHDG------------  189
Bs        KAYG-LNKVIVSTYQAVSGAGNEAVKELYSQTQAI--LNKEEIEPE-------------  186
At        HHAK-VKRMVVSTYQAASGAGAAAMEELVQQTREV--LEGK-----------------  186
Tt        RAFQ-AKRVIVATYQAASGAGAKAMEELLTETHRF--LHGE-----------------  176
Mj        DKFG-LEAVFIATMQAVSGAGYN-GVPSMAILDNL----------------------  203
           :  :: ** **.*                 .

Ec        TRSGELPVDNFGVPLAGSLIPWIDKQLDNG--QSREEWKGQAETNKILNTSSVIPVDGLC  265
Sc        -IPYIGGEEDKMEWETKKILAPLAEDKTHVKLLTPEEIKVSAQCNRVAVSDGHT-ECISL  262
Cg        QAADAGDVGPYVSPIAYNVLPFAGNLVDDGTFETDEEQKLRNESRKILGLPDLK-VSGTC  248
Bs        IMPVKGDK--KHYQTAFNAIPQIDKFQDNG--YTFEEMKMINETKKIMHMPDLQ-VAATC  241
At        --PPTCNI--FGQQYAFNLFSHNAPILDNG--YNEEEMKLVKETRKIWNDTEVK-VTATC  239
Tt        --APKAEA--FAHPLPFNVIPHIDAFQENG--YTREEMKVVWETHKIFGDDTIR-ISATA  229
Mj        -IPFIKNEEEKMQTESLKLLGTLKDGK--VELAN---FKISASCNRVAVIDGHT-ESIFV  256
                             . . :         *    . .::

Ec        VRVGALRCHSQAFTIKLKKDVSIPTVEELLAAHNPWAKVVPNDREITMRELTPAAVTGTL  325
Sc        RFKNRPAPSVEQVKTCLKEYVCDAYKLGCHSAPKQTIHVLEQPD--RPQPRLDRNRDSGY  320
Cg        VRVPVFTGHTLTIHAEFDK-AITVDQAQEILGAASGVKLVD--------VPTPLAAAGID  299
Bs        VRLPIQTGHSESVYIEIDRDDATVEDIKNLLKEAPGVTLQDDPS--QQLYPMPADAVGKN  299
At        IRVPVMRAHAESVNLQFEN--PLDENTAREILKKAPGVYIIDDRA--SNTFPTPLDVSNKD  296
Tt        VRVPTLRAHAEAVSVEFAR-PVTPEAAREVLKEAPGVEVVDEPE--AKRYPMPLTASGKW  286
Mj        KTKEGAEP--EEIKEVMDKF--DPLKDLNLPTYAKPIVIREEID--RPQPRLDRNEGNGM  310
                        . :                            .

Ec        TTPVGRLRKLN--MGPEFLSAFTVGDQLLWGAAEPLRRMLRQLA-----  367
Sc        GVSVGIRIREDP----LLDFKMVVLSHNTIIGAAGSGVLIAEILLARNLI  365
Cg        ESLVGIRIRQDSTVDDNRGLVLVVSGDNLRKGAALNTIQIAELLVK----  344
Bs        DVFVGIRIRKDLDRAN--GFHLWVVSDNLLKGAAWNSVQIAESLKKLNLV  346
At        DVAVGIRIRRDVSQDGNFGLDIFVCGDQIRKGAALNAVQIAEMLL-----  340
Tt        DVEVGIRIRKSLAFEN--GLDFFVVGDQLLKGAALNAVQIAEEWLKGA-- 331
Mj        SIVVGIRIRKDP----IFDVKYTALEHNTIRGAGASVLNAEYFVKKYI-  354
          ***:*.           .   . .:   ***       .
```

Figure 3

SEQUENCE LISTING

```
<160> NUMBER OF SEQ ID NOS: 231

<210> SEQ ID NO 1
<211> LENGTH: 33
<212> TYPE: DNA
<213> ORGANISM: Artificial Sequence
<220> FEATURE:
<223> OTHER INFORMATION: Synthetic Construct - Primer for amplification

<400> SEQUENCE: 1
cacgaggtac atatgtctga aattgttgtc tcc                                    33

<210> SEQ ID NO 2
<211> LENGTH: 29
<212> TYPE: DNA
<213> ORGANISM: Artificial Sequence
<220> FEATURE:
<223> OTHER INFORMATION: Synthetic Construct - Primer for amplification

<400> SEQUENCE: 2
cttccagggg atccagtatt tactcaaac                                         29

<210> SEQ ID NO 3
<211> LENGTH: 1350
<212> TYPE: DNA
<213> ORGANISM: Escherichia coli

<400> SEQUENCE: 3
atgtctgaaa ttgttgtctc caaatttggc ggtaccagcg tagctgattt tgacgccatg        60
aaccgcagcg ctgatattgt gctttctgat gccaacgtgc gtttagttgt cctctcggct      120
tctgctggta tcactaatct gctggtcgct ttagctgaag gactggaacc tggcgagcga      180
ttcgaaaaac tcgacgctat ccgcaacatc cagtttgcca ttctggaacg tctgcgttac      240
ccgaacgtta tccgtgaaga gattgaacgt ctgctggaga acattactgt tctggcagaa      300
gcggcggcgc tggcaacgtc tccggcgctg acagatgagc tggtcagcca cggcgagctg      360
atgtcgaccc tgctgtttgt tgagatcctg cgcgaacgcg atgttcaggc acagtggttt      420
gatgtacgta aagtgatgcg taccaacgac cgatttggtc gtgcagagcc agatatagcc      480
gcgctggcgg aactggccgc gctgcagctg ctcccacgtc tcaatgaagg cttagtgatc      540
acccagggat ttatcggtag cgaaaataaa ggtcgtacaa cgacgcttgg ccgtggaggc      600
agcgattata cggcagcctt gctggcggag gctttacacg catctcgtgt tgatatctgg      660
accgacgtcc cgggcatcta caccaccgat ccacgcgtag tttccgcagc aaaacgcatt      720
gatgaaatcg cgtttgccga agcggcagag atggcaactt ttggtgcaaa agtactgcat      780
ccggcaacgt tgctacccgc agtacgcagc gatatcccgg tctttgtcgg ctccagcaaa      840
```

-continued

```
gacccacgcg caggtggtac gctggtgtgc aataaaactg aaaatccgcc gctgttccgc      900
gctctggcgc ttcgtcgcaa tcagactctg ctcactttgc acagcctgaa atgctgcat       960 tctcgcggtt tcctcgcgga agttttcggc atcctcgcgc ggcataatat ttcggtagac     1020
ttaatcacca cgtcagaagt gagcgtggca ttaacccttg ataccaccgg ttcaacctcc     1080
actggcgata cgttgctgac gcaatctctg ctgatggagc tttccgcact gtgtcgggtg    1140
gaggtggaag aaggtctggc gctggtcgcg ttgattggca atgacctgtc aaaagcctgc    1200
ggcgttggca agaggtatt cggcgtactg gaaccgttca acattcgcat gatttgttat     1260
ggcgcatcca gccataacct gtgcttcctg gtgcccggcg aagatgccga gcaggtggtg    1320
caaaaactgc atagtaattt gtttgagtaa                                      1350
```

<210> SEQ ID NO 4
<211> LENGTH: 449
<212> TYPE: PRT
<213> ORGANISM: Escherichia coli

<400> SEQUENCE: 4

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
```

```
                275                 280                 285
Val Cys Asn Lys Thr Glu Asn Pro Pro Leu Phe Arg Ala Leu Ala Leu
            290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
                355                 360                 365

Ser Leu Leu Met Glu Leu Ser Ala Leu Cys Arg Val Glu Val Glu Glu
            370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
                435                 440                 445

Glu

<210> SEQ ID NO 5
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 5
tataatgcta gcatgccaat ggatttccaa cc                                    32

<210> SEQ ID NO 6
<211> LENGTH: 39
<212> TYPE: DNA
<213> ORGANISM: Artificial Sequence
<220> FEATURE:
<223> OTHER INFORMATION: Synthetic Construct - Primer for amplification

<400> SEQUENCE: 6
tataatgaat tcttaaattc caagtctttt caattgttc                             39

<210> SEQ ID NO 7
<211> LENGTH: 1584
<212> TYPE: DNA
<213> ORGANISM: Saccharomyces cerevisiae

<400> SEQUENCE: 7
atgccaatgg atttccaacc tacatcaagt cattcgaact gggtcgtgca aaagttcggt      60
ggtacatctg tcggtaaatt tcccgtccaa atagtggatg acattgtgaa gcactattct     120
aaacctgacg gcccaaacaa taatgtcgct gtcgtttgtt ccgcccgttc ttcatacacc     180
aaggctgaag gtaccacttc tcgtcttttg aaatgttgtg atttggcttc gcaagaatct     240
gaatttcaag acattatcga agttatcaga caagaccata tcgataatgc cgaccgcttc     300
attctcaatc ctgccttgca agccaagtta gtggatgata ccaataaaga acttgaactg     360
gtcaagaaat atttaaatgc ttcaaaagtt ttgggtgaag tgagttcacg tacagtagat     420
```

-continued

```
ctggtgatgt catgtggtga agttgagt tgtttgttca tgactgcttt atgtaatgac    480
cgtggctgta aggccaaata tgtggatttg agccacattg ttccctctga tttcagtgcc    540
agcgctttgg ataacagttt ctacactttc ctggttcaag cattgaaaga aaaattggcc    600 cccttttgtaa gtgctaaaga gcgtatcgtt ccagtcttta cagggttttt tggtttagtt    660
ccaactggtc ttctgaatgg tgttggtcgt ggctataccg atttatgtgc cgctttgata    720
gcagttgctg taaatgctga tgaactacaa gtttggaagg aagttgatgg tatatttact    780
gctgatcctc gtaaggttcc tgaagcacgt ttgctagaca gtgttactcc agaagaagct    840
tctgaattaa catattatgg ttccgaagtt atacatcctt ttacgatgga acaagttatt    900
agggctaaga ttcctattag aatcaagaat gttcaaaatc cattaggtaa cggtaccatt    960
atctacccag ataatgtagc aaagaagggg gaatctactc caccacatcc tcctgagaac   1020
ttatcctcat ctttctatga aaagagaaag agaggtgcca ctgctatcac caccaaaaat   1080
gacattttcg tcatcaacat tcattccaat aagaaaaccc tatcccatgg tttcctagct   1140
caaatattta ccatcctgga taagtacaag ttagtcgtag atttaatatc tacttctgaa   1200
gttcatgttt cgatggcttt gcccattcca gatgcagact cattaaaatc tctgagacaa   1260
gctgaggaaa aattgagaat tttaggttct gttgatatca caagaagtt gtctattgtt   1320 tcattagttg gtaaacatat gaaacaatac atcggcattg ctggtaccat gtttactact   1380
cttgctgaag aaggcatcaa cattgaaatg atttctcaag gggcaaatga aataaacata   1440
tcctgcgtta tcaatgaatc tgactccata aaagcgctac aatgtattca tgccaagtta   1500
ctaagtgagc ggacaaatac ttcaaaccaa tttgaacatg ccattgatga acgtttagaa   1560
caattgaaaa gacttggaat ttaa                                          1584
```

<210> SEQ ID NO 8
<211> LENGTH: 527
<212> TYPE: PRT
<213> ORGANISM: Saccharomyces cerevisiae

<400> SEQUENCE: 8

```
Met Pro Met Asp Phe Gln Pro Thr Ser Ser His Ser Asn Trp Val Val
 1               5                  10                  15

Gln Lys Phe Gly Gly Thr Ser Val Gly Lys Phe Pro Val Gln Ile Val
            20                  25                  30

Asp Asp Ile Val Lys His Tyr Ser Lys Pro Asp Gly Pro Asn Asn Asn
        35                  40                  45

Val Ala Val Val Cys Ser Ala Arg Ser Ser Tyr Thr Lys Ala Glu Gly
    50                  55                  60

Thr Thr Ser Arg Leu Leu Lys Cys Cys Asp Leu Ala Ser Gln Glu Ser
65                  70                  75                  80

Glu Phe Gln Asp Ile Ile Glu Val Ile Arg Gln Asp His Ile Asp Asn
                85                  90                  95

Ala Asp Arg Phe Ile Leu Asn Pro Ala Leu Gln Ala Lys Leu Val Asp
            100                 105                 110

Asp Thr Asn Lys Glu Leu Glu Leu Val Lys Lys Tyr Leu Asn Ala Ser
        115                 120                 125

Lys Val Leu Gly Glu Val Ser Ser Arg Thr Val Asp Leu Val Met Ser
    130                 135                 140

Cys Gly Glu Lys Leu Ser Cys Leu Phe Met Thr Ala Leu Cys Asn Asp
145                 150                 155                 160
```

Arg Gly Cys Lys Ala Lys Tyr Val Asp Leu Ser His Ile Val Pro Ser
            165                 170                 175

Asp Phe Ser Ala Ser Ala Leu Asp Asn Ser Phe Tyr Thr Phe Leu Val
        180                 185                 190

Gln Ala Leu Lys Glu Lys Leu Ala Pro Phe Val Ser Ala Lys Glu Arg
        195                 200                 205

Ile Val Pro Val Phe Thr Gly Phe Gly Leu Val Pro Thr Gly Leu
210                 215                 220

Leu Asn Gly Val Gly Arg Gly Tyr Thr Asp Leu Cys Ala Ala Leu Ile
225                 230                 235                 240

Ala Val Ala Val Asn Ala Asp Glu Leu Gln Val Trp Lys Glu Val Asp
                245                 250                 255

Gly Ile Phe Thr Ala Asp Pro Arg Lys Val Pro Glu Ala Arg Leu Leu
                260                 265                 270

Asp Ser Val Thr Pro Glu Glu Ala Ser Glu Leu Thr Tyr Tyr Gly Ser
            275                 280                 285

Glu Val Ile His Pro Phe Thr Met Glu Gln Val Ile Arg Ala Lys Ile
        290                 295                 300

Pro Ile Arg Ile Lys Asn Val Gln Asn Pro Leu Gly Asn Gly Thr Ile
305                 310                 315                 320

Ile Tyr Pro Asp Asn Val Ala Lys Lys Gly Glu Ser Thr Pro Pro His
                325                 330                 335

Pro Pro Glu Asn Leu Ser Ser Ser Phe Tyr Glu Lys Arg Lys Arg Gly
                340                 345                 350

Ala Thr Ala Ile Thr Thr Lys Asn Asp Ile Phe Val Ile Asn Ile His
            355                 360                 365

Ser Asn Lys Lys Thr Leu Ser His Gly Phe Leu Ala Gln Ile Phe Thr
        370                 375                 380

Ile Leu Asp Lys Tyr Lys Leu Val Val Asp Leu Ile Ser Thr Ser Glu
385                 390                 395                 400

Val His Val Ser Met Ala Leu Pro Ile Pro Asp Ala Asp Ser Leu Lys
                405                 410                 415

Ser Leu Arg Gln Ala Glu Glu Lys Leu Arg Ile Leu Gly Ser Val Asp
                420                 425                 430

Ile Thr Lys Lys Leu Ser Ile Val Ser Leu Val Gly Lys His Met Lys
            435                 440                 445

Gln Tyr Ile Gly Ile Ala Gly Thr Met Phe Thr Thr Leu Ala Glu Glu
        450                 455                 460

Gly Ile Asn Ile Glu Met Ile Ser Gln Gly Ala Asn Glu Ile Asn Ile
465                 470                 475                 480

Ser Cys Val Ile Asn Glu Ser Asp Ser Ile Lys Ala Leu Gln Cys Ile
                485                 490                 495

His Ala Lys Leu Leu Ser Glu Arg Thr Asn Thr Ser Asn Gln Phe Glu
            500                 505                 510

His Ala Ile Asp Glu Arg Leu Glu Gln Leu Lys Arg Leu Gly Ile
        515                 520                 525

<210> SEQ ID NO 9
<211> LENGTH: 449
<212> TYPE: PRT
<213> ORGANISM: Escherichia coli
<220> FEATURE:
<221> NAME/KEY: MISC_FEATURE
<222> LOCATION: (119)..(119)
<223> OTHER INFORMATION: X being any of amino acid except E

```
<400> SEQUENCE: 9

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                    85                  90                  95

Val Leu Ala Glu Ala Ala Leu Ala Thr Ser Pro Ala Leu Thr Asp
                100                 105                 110

Glu Leu Val Ser His Gly Xaa Leu Met Ser Thr Leu Leu Phe Val Glu
                115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
        290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415
```

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu

<210> SEQ ID NO 10
<211> LENGTH: 35
<212> TYPE: DNA
<213> ORGANISM: Artificial Sequence
<220> FEATURE:
<223> OTHER INFORMATION: Synthetic Construct - Primer for amplification
<220> FEATURE:
<221> NAME/KEY: misc_feature
<222> LOCATION: (17)..(19)
<223> OTHER INFORMATION: nnn encoding anyone of the other 19 naturally
      existing proteinogenic amino acids, except glutamine

<400> SEQUENCE: 10
gctggtcagc catggcnnnc tgatgtcgac cctgc                               35

<210> SEQ ID NO 11
<211> LENGTH: 35
<212> TYPE: DNA
<213> ORGANISM: Artificial Sequence
<220> FEATURE:
<223> OTHER INFORMATION: Synthetic Construct - Primer for amplification
<220> FEATURE:
<221> NAME/KEY: misc_feature
<222> LOCATION: (17)..(19)
<223> OTHER INFORMATION: nnn encoding anyone of the other 19 naturally
      existing proteinogenic amino acids, except glutamine

<400> SEQUENCE: 11
gcagggtcga catcagnnng ccatggctga ccagc                               35

<210> SEQ ID NO 12
<211> LENGTH: 449
<212> TYPE: PRT
<213> ORGANISM: Escherichia coli

<400> SEQUENCE: 12

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Cys Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala

```
        145                 150                 155                 160
Ala Leu Ala Glu Leu Ala Ala Leu Gln Leu Leu Pro Arg Leu Asn Glu
                165                 170                 175
Gly Leu Val Ile Thr Gln Gly Phe Ile Gly Ser Glu Asn Lys Gly Arg
            180                 185                 190
Thr Thr Thr Leu Gly Arg Gly Gly Ser Asp Tyr Thr Ala Ala Leu Leu
        195                 200                 205
Ala Glu Ala Leu His Ala Ser Arg Val Asp Ile Trp Thr Asp Val Pro
    210                 215                 220
Gly Ile Tyr Thr Thr Asp Pro Arg Val Val Ser Ala Ala Lys Arg Ile
225                 230                 235                 240
Asp Glu Ile Ala Phe Ala Glu Ala Ala Glu Met Ala Thr Phe Gly Ala
                245                 250                 255
Lys Val Leu His Pro Ala Thr Leu Leu Pro Ala Val Arg Ser Asp Ile
            260                 265                 270
Pro Val Phe Val Gly Ser Ser Lys Asp Pro Arg Ala Gly Gly Thr Leu
        275                 280                 285
Val Cys Asn Lys Thr Glu Asn Pro Pro Leu Phe Arg Ala Leu Ala Leu
    290                 295                 300
Arg Arg Asn Gln Thr Leu Leu Thr Leu His Ser Leu Asn Met Leu His
305                 310                 315                 320
Ser Arg Gly Phe Leu Ala Glu Val Phe Gly Ile Leu Ala Arg His Asn
                325                 330                 335
Ile Ser Val Asp Leu Ile Thr Thr Ser Glu Val Ser Val Ala Leu Thr
            340                 345                 350
Leu Asp Thr Thr Gly Ser Thr Ser Thr Gly Asp Thr Leu Leu Thr Gln
        355                 360                 365
Ser Leu Leu Met Glu Leu Ser Ala Leu Cys Arg Val Glu Val Glu Glu
    370                 375                 380
Gly Leu Ala Leu Val Ala Leu Ile Gly Asn Asp Leu Ser Lys Ala Cys
385                 390                 395                 400
Gly Val Gly Lys Glu Val Phe Gly Val Leu Glu Pro Phe Asn Ile Arg
                405                 410                 415
Met Ile Cys Tyr Gly Ala Ser Ser His Asn Leu Cys Phe Leu Val Pro
            420                 425                 430
Gly Glu Asp Ala Glu Gln Val Val Gln Lys Leu His Ser Asn Leu Phe
        435                 440                 445
Glu

<210> SEQ ID NO 13
<211> LENGTH: 1350
<212> TYPE: DNA
<213> ORGANISM: Escherichia coli

<400> SEQUENCE: 13
atgtctgaaa ttgttgtctc caaatttggc ggtaccagcg tagctgattt tgacgccatg    60
aaccgcagcg ctgatattgt gctttctgat gccaacgtgc gtttagttgt cctctcggct   120
tctgctggta tcactaatct gctggtcgct ttagctgaag gactggaacc tggcgagcga   180
ttcgaaaaac tcgacgctat ccgcaacatc cagtttgcca ttctggaacg tctgcgttac   240
ccgaacgtta tccgtgaaga gattgaacgt ctgctggaga acattactgt tctggcagaa   300
gcggcggcgc tggcaacgtc tccggcgctg acagatgagc tggtcagcca tggctgtctg   360
atgtcgaccc tgctgtttgt tgagatcctg cgcgaacgcg atgttcaggc acagtggttt   420
```

```
gatgtacgta aagtgatgcg taccaacgac cgatttggtc gtgcagagcc agatatagcc    480
gcgctggcgg aactggccgc gctgcagctg ctcccacgtc tcaatgaagg cttagtgatc    540
acccagggat ttatcggtag cgaaaataaa ggtcgtacaa cgacgcttgg ccgtggaggc    600
agcgattata cggcagcctt gctggcggag gctttacacg catctcgtgt tgatatctgg    660
accgacgtcc cgggcatcta caccaccgat ccacgcgtag tttccgcagc aaaacgcatt    720
gatgaaatcg cgtttgccga agcggcagag atggcaactt tggtgcaaa agtactgcat    780
ccggcaacgt tgctacccgc agtacgcagc gatatcccgg tctttgtcgg ctccagcaaa    840
gacccacgcg caggtggtac gctggtgtgc aataaaactg aaaatccgcc gctgttccgc    900
gctctggcgc ttcgtcgcaa tcagactctg ctcactttgc acagcctgaa tatgctgcat    960
tctcgcggtt tcctcgcgga agttttcggc atcctcgcgc ggcataatat ttcggtagac   1020
ttaatcacca cgtcagaagt gagcgtggca ttaaccctttg ataccaccgg ttcaacctcc   1080
actggcgata cgttgctgac gcaatctctg ctgatggagc tttccgcact gtgtcgggtg   1140
gaggtggaag aaggtctggc gctggtcgcg ttgattggca atgacctgtc aaaagcctgc   1200
ggcgttggca aagaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                    1350
```

```
<210> SEQ ID NO 14
<211> LENGTH: 449
<212> TYPE: PRT
<213> ORGANISM: Escherichia coli

<400> SEQUENCE: 14

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Gly Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205
```

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu

<210> SEQ ID NO 15
<211> LENGTH: 1350
<212> TYPE: DNA
<213> ORGANISM: Escherichia coli

<400> SEQUENCE: 15
atgtctgaaa ttgttgtctc caaatttggc ggtaccagcg tagctgattt tgacgccatg     60
aaccgcagcg ctgatattgt gctttctgat gccaacgtgc gtttagttgt cctctcggct    120
tctgctggta tcactaatct gctggtcgct ttagctgaag gactggaacc tggcgagcga    180
ttcgaaaaac tcgacgctat ccgcaacatc cagtttgcca ttctggaacg tctgcgttac    240
ccgaacgtta tccgtgaaga gattgaacgt ctgctggaga acattactgt tctggcagaa    300
gcggcggcgc tggcaacgtc tccggcgctg acagatgagc tggtcagcca tggcggcctg    360
atgtcgaccc tgctgtttgt tgagatcctg cgcgaacgcg atgttcaggc acagtggttt    420
gatgtacgta aagtgatgcg taccaacgac cgatttggtc gtgcagagcc agatatagcc    480
gcgctggcgg aactggccgc gctgcagctg ctcccacgtc tcaatgaagg cttagtgatc    540
acccagggat ttatcggtag cgaaaataaa ggtcgtacaa cgacgcttgg ccgtggaggc    600
agcgattata cggcagcctt gctggcggag gctttacacg catctcgtgt tgatatctgg    660
accgacgtcc cgggcatcta caccaccgat ccacgcgtag tttccgcagc aaaacgcatt    720

-continued

```
gatgaaatcg cgtttgccga agcggcagag atggcaactt ttggtgcaaa agtactgcat    780
ccggcaacgt tgctacccgc agtacgcagc gatatcccgg tctttgtcgg ctccagcaaa    840
gacccacgcg caggtggtac gctggtgtgc aataaaactg aaaatccgcc gctgttccgc    900
gctctggcgc ttcgtcgcaa tcagactctg ctcactttgc acagcctgaa tatgctgcat    960
tctcgcggtt cctcgcgga agttttcggc atcctcgcgc ggcataatat ttcggtagac   1020
ttaatcacca cgtcagaagt gagcgtggca ttaacccttg ataccaccgg ttcaacctcc   1080
actggcgata cgttgctgac gcaatctctg ctgatggagc tttccgcact gtgtcgggtg   1140
gaggtggaag aagtctggc gctggtcgcg ttgattggca atgacctgtc aaaagcctgc   1200
ggcgttggca agaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                   1350
```

<210> SEQ ID NO 16
<211> LENGTH: 449
<212> TYPE: PRT
<213> ORGANISM: Escherichia coli

<400> SEQUENCE: 16

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Asn Leu Met Ser Thr Leu Leu Phe Val Glu
        115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255
```

```
Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 17
<211> LENGTH: 1350
<212> TYPE: DNA
<213> ORGANISM: Escherichia coli

<400> SEQUENCE: 17
atgtctgaaa ttgttgtctc caaatttggc ggtaccagcg tagctgattt tgacgccatg      60
aaccgcagcg ctgatattgt gctttctgat gccaacgtgc gtttagttgt cctctcgggt     120
tctgctggta tcactaatct gctggtcgct ttagctgaag actggaacc tggcgagcga     180 ttcgaaaaac tcgacgctat ccgcaacatc cagtttgcca ttctgaaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca tgcaatctg     360 atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag ctttacacg catctcgtgt tgatatctgg     660
accgacgtcc cgggcatcta caccaccgat ccacgcgtag tttccgcagc aaaacgcatt     720
gatgaaatcg cgtttgccga agcggcagag atggcaactt tggtgcaaa agtactgcat     780 ccggcaacgt tgctacccgc agtacgcagc gatatcccgg tctttgtcgg ctccagcaaa     840
gacccacgcg caggtggtac gctggtgtgc aataaaactg aaaatccgcc gctgttccgc     900
gctctggcgc ttcgtcgcaa tcagactctg ctcactttgc acagcctgaa tatgctgcat     960
tctcgcggtt tcctcgcgga agttttcggc atcctcgcgc ggcataatat ttcggtagac    1020
```

```
ttaatcacca cgtcagaagt gagcgtggca ttaaccettg ataccaccgg ttcaacctcc   1080
actggcgata cgttgctgac gcaatctctg ctgatggagc tttccgcact gtgtcgggtg   1140
gaggtggaag aaggtctggc gctggtcgcg ttgattggca atgacctgtc aaaagcctgc   1200
ggcgttggca agaggtatt cggcgtactg aaccgttca acattcgcat gatttgttat    1260
ggcgcatcca gccataacct gtgcttcctg gtgcccggcg aagatgccga gcaggtggtg   1320
caaaaactgc atagtaattt gtttgagtaa                                   1350
```

<210> SEQ ID NO 18
<211> LENGTH: 449
<212> TYPE: PRT
<213> ORGANISM: Escherichia coli

<400> SEQUENCE: 18

```
Met Ser Glu Ile Val Ser Lys Phe Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Pro Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
```

```
                    305                 310                 315                 320
Ser Arg Gly Phe Leu Ala Glu Val Phe Gly Ile Leu Ala Arg His Asn
                325                 330                 335
Ile Ser Val Asp Leu Ile Thr Thr Ser Glu Val Ser Val Ala Leu Thr
                340                 345                 350
Leu Asp Thr Thr Gly Ser Thr Ser Thr Gly Asp Thr Leu Leu Thr Gln
                355                 360                 365
Ser Leu Leu Met Glu Leu Ser Ala Leu Cys Arg Val Glu Val Glu Glu
                370                 375                 380
Gly Leu Ala Leu Val Ala Leu Ile Gly Asn Asp Leu Ser Lys Ala Cys
385                 390                 395                 400
Gly Val Gly Lys Glu Val Phe Gly Val Leu Glu Pro Phe Asn Ile Arg
                405                 410                 415
Met Ile Cys Tyr Gly Ala Ser Ser His Asn Leu Cys Phe Leu Val Pro
                420                 425                 430
Gly Glu Asp Ala Glu Gln Val Val Gln Lys Leu His Ser Asn Leu Phe
                435                 440                 445
Glu
```

<210> SEQ ID NO 19
<211> LENGTH: 1350
<212> TYPE: DNA
<213> ORGANISM: Escherichia coli

<400> SEQUENCE: 19

```
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag actggaaacc tggcgagcga     180
ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca tggcccgctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cgggcatcta caccaccgat ccacgcgtag tttccgcagc aaaacgcatt     720
gatgaaatcg cgtttgccga gcggcagag atggcaactt tggtgcaaa agtactgcat     780
ccggcaacgt tgctacccgc agtacgcagc gatatcccgg tctttgtcgg ctccagcaaa     840
gacccacgcg caggtggtac gctggtgtgc aataaaactg aaaatccgcc gctgttccgc     900
gctctggcgc ttcgtcgcaa tcagactctg ctcactttgc acagcctgaa atgctgcat      960
tctcgcggtt cctcgcgga gttttcggc atcctcgcgc ggcataatat tcggtagac     1020
ttaatcacca cgtcagaagt gagcgtggca ttaaccttg ataccaccgg ttcaacctcc     1080
actggcgata cgttgctgac gcaatctctg ctgatggagc tttccgcact gtgtcgggtg    1140
gaggtggaag aaggtctggc gctggtcgcg ttgattggca atgacctgtc aaaagcctgc    1200
ggcgttggca agaggtatt cggcgtactg gaaccgttca acattcgcat gatttgttat    1260
ggcgcatcca gccataacct gtgcttcctg gtgcccggcg aagatgccga gcaggtggtg    1320
```
caaaaactgc atagtaattt gtttgagtaa                                                     1350

<210> SEQ ID NO 20
<211> LENGTH: 449
<212> TYPE: PRT
<213> ORGANISM: Escherichia coli

<400> SEQUENCE: 20

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Gln Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

```
Ser Leu Leu Met Glu Leu Ser Ala Leu Cys Arg Val Glu Val Glu Glu
    370                 375                 380
Gly Leu Ala Leu Val Ala Leu Ile Gly Asn Asp Leu Ser Lys Ala Cys
385                 390                 395                 400
Gly Val Gly Lys Glu Val Phe Gly Val Leu Glu Pro Phe Asn Ile Arg
                405                 410                 415
Met Ile Cys Tyr Gly Ala Ser Ser His Asn Leu Cys Phe Leu Val Pro
            420                 425                 430
Gly Glu Asp Ala Glu Gln Val Val Gln Lys Leu His Ser Asn Leu Phe
        435                 440                 445
Glu
```

<210> SEQ ID NO 21
<211> LENGTH: 1350
<212> TYPE: DNA
<213> ORGANISM: Escherichia coli

<400> SEQUENCE: 21

| | | | | | |
|---|---|---|---|---|---|
| atgtctgaaa | ttgttgtctc | caaatttggc | ggtaccagcg | tagctgattt | tgacgccatg | 60 |
| aaccgcagcg | ctgatattgt | gctttctgat | gccaacgtgc | gtttagttgt | cctctcggct | 120 |
| tctgctggta | tcactaatct | gctggtcgct | ttagctgaag | gactggaacc | tggcgagcga | 180 |
| ttcgaaaaac | tcgacgctat | ccgcaacatc | cagtttgcca | ttctggaacg | tctgcgttac | 240 |
| ccgaacgtta | tccgtgaaga | gattgaacgt | ctgctggaga | cattactgt | tctggcagaa | 300 |
| gcggcggcgc | tggcaacgtc | tccggcgctg | acagatgagc | tggtcagcca | tggccagctg | 360 |
| atgtcgaccc | tgctgtttgt | tgagatcctg | cgcgaacgcg | atgttcaggc | acagtggttt | 420 |
| gatgtacgta | aagtgatgcg | taccaacgac | cgatttggtc | gtgcagagcc | agatatagcc | 480 |
| gcgctggcgg | aactggccgc | gctgcagctg | ctcccacgtc | tcaatgaagg | cttagtgatc | 540 |
| acccaggat | tatcggtag | cgaaaataaa | ggtcgtacaa | cgacgcttgg | ccgtggaggc | 600 |
| agcgattata | cggcagcctt | gctggcggag | gctttacacg | catctcgtgt | tgatatctgg | 660 |
| accgacgtcc | cgggcatcta | caccaccgat | ccacgcgtag | tttccgcagc | aaaacgcatt | 720 |
| gatgaaatcg | cgttttgccga | agcggcagag | atggcaactt | ttggtgcaaa | agtactgcat | 780 |
| ccggcaacgt | tgctacccgc | agtacgcagc | gatatcccgg | tctttgtcgg | ctccagcaaa | 840 |
| gacccacgcg | caggtggtac | gctggtgtgc | aataaaactg | aaaatccgcc | gctgttccgc | 900 |
| gctctggcgc | ttcgtcgcaa | tcagactctg | ctcactttgc | acagcctgaa | atgctgcat | 960 |
| tctcgcggtt | cctcgcgga | agttttcggc | atcctcgcgc | ggcataatat | ttcggtagac | 1020 |
| ttaatcacca | cgtcagaagt | gagcgtggca | ttaacccttg | ataccaccgg | ttcaacctcc | 1080 |
| actggcgata | cgttgctgac | gcaatctctg | ctgatggagc | tttccgcact | gtgtcgggtg | 1140 |
| gaggtggaag | aaggtctggc | gctggtcgcg | ttgattggca | atgacctgtc | aaaagcctgc | 1200 |
| ggcgttggca | agaggtatt | cggcgtactg | gaaccgttca | acattcgcat | gatttgttat | 1260 |
| ggcgcatcca | gccataacct | gtgcttcctg | gtgcccggcg | aagatgccga | gcaggtggtg | 1320 |
| caaaaactgc | atagtaattt | gtttgagtaa | | | | 1350 |

<210> SEQ ID NO 22
<211> LENGTH: 449
<212> TYPE: PRT
<213> ORGANISM: Escherichia coli

<400> SEQUENCE: 22

```
Met Ser Glu Ile Val Val Ser Lys Phe Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Gly Ile Thr Asn Leu Leu
            35                  40                  45

Val Ala Leu Ala Glu Gly Leu Glu Pro Gly Glu Arg Phe Glu Lys Leu
50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Ser Leu Met Ser Thr Leu Leu Phe Val Glu
                115                 120                 125

Ile Leu Arg Glu Arg Asp Val Gln Ala Gln Trp Phe Asp Val Arg Lys
            130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
            195                 200                 205

Ala Glu Ala Leu His Ala Ser Arg Val Asp Ile Trp Thr Asp Val Pro
            210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
            290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
            370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415
```

```
Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu
```

<210> SEQ ID NO 23
<211> LENGTH: 1350
<212> TYPE: DNA
<213> ORGANISM: Escherichia coli

<400> SEQUENCE: 23

| | | |
|---|---|---|
| atgtctgaaa ttgttgtctc caaatttggc ggtaccagcg tagctgattt tgacgccatg | 60 |
| aaccgcagcg ctgatattgt gctttctgat gccaacgtgc gtttagttgt cctctcggct | 120 |
| tctgctggta tcactaatct gctggtcgct ttagctgaag actggaacc tggcgagcga | 180 |
| ttcgaaaaac tcgacgctat ccgcaacatc cagtttgcca ttctggaacg tctgcgttac | 240 |
| ccgaacgtta tccgtgaaga gattgaacgt ctgctggaga acattactgt tctggcagaa | 300 |
| gcggcggcgc tggcaacgtc tccggcgctg acagatgagc tggtcagcca tggctcgctg | 360 |
| atgtcgaccc tgctgtttgt tgagatcctg cgcgaacgcg atgttcaggc acagtggttt | 420 |
| gatgtacgta agtgatgcg taccaacgac cgatttggtc gtgcagagcc agatatagcc | 480 |
| gcgctggcgg aactggccgc gctgcagctg ctcccacgtc tcaatgaagg cttagtgatc | 540 |
| acccagggat ttatcggtag cgaaaataaa ggtcgtacaa cgacgcttgg ccgtggaggc | 600 |
| agcgattata cggcagcctt gctggcgag gctttacacg catctcgtgt tgatatctgg | 660 |
| accgacgtcc cgggcatcta caccaccgat ccacgcgtag tttccgcagc aaaacgcatt | 720 |
| gatgaaatcg cgtttgccga agcggcagag atggcaactt tggtgcaaa agtactgcat | 780 |
| ccggcaacgt tgctacccgc agtacgcagc gatatcccgg tctttgtcgg ctccagcaaa | 840 |
| gacccacgcg caggtggtac gctggtgtgc aataaaactg aaaatccgcc gctgttccgc | 900 |
| gctctggcgc ttcgtcgcaa tcagactctg ctcactttgc acagcctgaa tatgctgcat | 960 |
| tctcgcggtt tcctcgcgga gttttcggc atcctcgcgc ggcataatat tcggtagac | 1020 |
| ttaatcacca cgtcagaagt gagcgtggca ttaacccttg ataccaccgg ttcaacctcc | 1080 |
| actggcgata cgttgctgac gcaatctctg ctgatggagc tttccgcact gtgtcgggtg | 1140 |
| gaggtggaag aaggtctggc gctggtcgcg ttgattggca atgacctgtc aaaagcctgc | 1200 |
| ggcgttggca agaggtatt cggcgtactg gaaccgttca acattcgcat gatttgttat | 1260 |
| ggcgcatcca gccataacct gtgcttcctg gtgcccggcg aagatgccga gcaggtggtg | 1320 |
| caaaaactgc atagtaattt gtttgagtaa | 1350 |

<210> SEQ ID NO 24
<211> LENGTH: 449
<212> TYPE: PRT
<213> ORGANISM: Escherichia coli

<400> SEQUENCE: 24

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45
```

Val Ala Leu Ala Glu Gly Leu Glu Pro Gly Glu Arg Phe Glu Lys Leu
 50                  55                  60

Asp Ala Ile Arg Asn Ile Gln Phe Ala Ile Leu Glu Arg Leu Arg Tyr
 65                  70                  75                  80

Pro Asn Val Ile Arg Glu Ile Glu Arg Leu Leu Glu Asn Ile Thr
                     85                  90                  95

Val Leu Ala Glu Ala Ala Leu Ala Thr Ser Pro Ala Leu Thr Asp
                 100                 105                 110

Glu Leu Val Ser His Gly Thr Leu Met Ser Thr Leu Leu Phe Val Glu
                 115                 120                 125

Ile Leu Arg Glu Arg Asp Val Gln Ala Gln Trp Phe Asp Val Arg Lys
 130                 135                 140

Val Met Arg Thr Asn Asp Arg Phe Gly Arg Ala Glu Pro Asp Ile Ala
 145                 150                 155                 160

Ala Leu Ala Glu Leu Ala Ala Leu Gln Leu Leu Pro Arg Leu Asn Glu
                 165                 170                 175

Gly Leu Val Ile Thr Gln Gly Phe Ile Gly Ser Glu Asn Lys Gly Arg
                 180                 185                 190

Thr Thr Thr Leu Gly Arg Gly Gly Ser Asp Tyr Thr Ala Ala Leu Leu
                 195                 200                 205

Ala Glu Ala Leu His Ala Ser Arg Val Asp Ile Trp Thr Asp Val Pro
 210                 215                 220

Gly Ile Tyr Thr Thr Asp Pro Arg Val Val Ser Ala Ala Lys Arg Ile
 225                 230                 235                 240

Asp Glu Ile Ala Phe Ala Glu Ala Ala Glu Met Ala Thr Phe Gly Ala
                 245                 250                 255

Lys Val Leu His Pro Ala Thr Leu Leu Pro Ala Val Arg Ser Asp Ile
                 260                 265                 270

Pro Val Phe Val Gly Ser Ser Lys Asp Pro Arg Ala Gly Gly Thr Leu
                 275                 280                 285

Val Cys Asn Lys Thr Glu Asn Pro Pro Leu Phe Arg Ala Leu Ala Leu
                 290                 295                 300

Arg Arg Asn Gln Thr Leu Leu Thr Leu His Ser Leu Asn Met Leu His
 305                 310                 315                 320

Ser Arg Gly Phe Leu Ala Glu Val Phe Gly Ile Leu Ala Arg His Asn
                 325                 330                 335

Ile Ser Val Asp Leu Ile Thr Thr Ser Glu Val Ser Val Ala Leu Thr
                 340                 345                 350

Leu Asp Thr Thr Gly Ser Thr Ser Thr Gly Asp Thr Leu Leu Thr Gln
                 355                 360                 365

Ser Leu Leu Met Glu Leu Ser Ala Leu Cys Arg Val Glu Val Glu Glu
                 370                 375                 380

Gly Leu Ala Leu Val Ala Leu Ile Gly Asn Asp Leu Ser Lys Ala Cys
 385                 390                 395                 400

Gly Val Gly Lys Glu Val Phe Gly Val Leu Glu Pro Phe Asn Ile Arg
                 405                 410                 415

Met Ile Cys Tyr Gly Ala Ser Ser His Asn Leu Cys Phe Leu Val Pro
                 420                 425                 430

Gly Glu Asp Ala Glu Gln Val Val Gln Lys Leu His Ser Asn Leu Phe
                 435                 440                 445

Glu

<210> SEQ ID NO 25

```
<211> LENGTH: 1350
<212> TYPE: DNA
<213> ORGANISM: Escherichia coli

<400> SEQUENCE: 25
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag gactggaacc tggcgagcga     180
ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca tggcactctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cggcatcta caccaccgat ccacgcgtag tttccgcagc aaaacgcatt     720
gatgaaatcg cgtttgccga agcggcagag atggcaactt ttggtgcaaa agtactgcat     780
ccggcaacgt tgctacccgc agtacgcagc gatatcccgg tctttgtcgg ctccagcaaa     840
gacccacgcg caggtggtac gctggtgtgc aataaaactg aaaatccgcc gctgttccgc     900
gctctggcgc ttcgtcgcaa tcagactctg ctcactttgc acagcctgaa atgctgcat     960 tctcgcggtt cctcgcgga gttttcggc atcctcgcgc ggcataatat tcggtagac    1020 ttaatcacca cgtcagaagt gagcgtggca ttaaccttg ataccaccgg ttcaacctcc    1080
actggcgata cgttgctgac gcaatctctg ctgatggagc tttccgcact gtgtcgggtg    1140
gaggtggaag aagtctggc gctggtcgcg ttgattggca tgacctgtc aaaagcctgc    1200 ggcgttggca agaggtatt cggcgtactg gaaccgttca acattcgcat gatttgttat    1260
ggcgcatcca gccataacct gtgcttcctg gtgcccggcg aagatgccga gcaggtggtg    1320
caaaaactgc atagtaattt gtttgagtaa                                    1350

<210> SEQ ID NO 26
<211> LENGTH: 449
<212> TYPE: PRT
<213> ORGANISM: Escherichia coli

<400> SEQUENCE: 26

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
```

```
                100                 105                 110
Glu Leu Val Ser His Gly Val Leu Met Ser Thr Leu Leu Phe Val Glu
            115                 120                 125

Ile Leu Arg Glu Arg Asp Val Gln Ala Gln Trp Phe Asp Val Arg Lys
        130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Pro Arg Leu Asn Glu
                165                 170                 175

Gly Leu Val Ile Thr Gln Gly Phe Ile Gly Ser Glu Asn Lys Gly Arg
                180                 185                 190

Thr Thr Thr Leu Gly Arg Gly Gly Ser Asp Tyr Thr Ala Ala Leu Leu
            195                 200                 205

Ala Glu Ala Leu His Ala Ser Arg Val Asp Ile Trp Thr Asp Val Pro
        210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu

<210> SEQ ID NO 27
<211> LENGTH: 1350
<212> TYPE: DNA
<213> ORGANISM: Escherichia coli

<400> SEQUENCE: 27
atgtctgaaa ttgttgtctc caaatttggc ggtaccagcg tagctgattt tgacgccatg        60
aaccgcagcg ctgatattgt gctttctgat gccaacgtgc gtttagttgt cctctcggct       120
```

```
tctgctggta tcactaatct gctggtcgct ttagctgaag gactggaacc tggcgagcga      180
ttcgaaaaac tcgacgctat ccgcaacatc cagtttgcca ttctggaacg tctgcgttac      240
ccgaacgtta tccgtgaaga gattgaacgt ctgctggaga acattactgt tctggcagaa      300
gcggcggcgc tggcaacgtc tccggcgctg acagatgagc tggtcagcca tggcgtgctg      360
atgtcgaccc tgctgtttgt tgagatcctg cgcgaacgcg atgttcaggc acagtggttt      420
gatgtacgta aagtgatgcg taccaacgac cgatttggtc gtgcagagcc agatatagcc      480
gcgctggcgg aactggccgc gctgcagctg ctcccacgtc tcaatgaagg cttagtgatc      540
acccagggat ttatcggtag cgaaaataaa ggtcgtacaa cgacgcttgg ccgtggaggc      600
agcgattata cggcagcctt gctggcggag gctttacacg catctcgtgt tgatatctgg      660
accgacgtcc cgggcatcta caccaccgat ccacgcgtag tttccgcagc aaaacgcatt      720
gatgaaatcg cgtttgccga agcggcagag atggcaactt ttggtgcaaa agtactgcat      780
ccggcaacgt tgctacccgc agtacgcagc gatatcccgg tctttgtcgg ctccagcaaa      840
gacccacgcg caggtggtac gctggtgtgc aataaaactg aaaatccgcc gctgttccgc      900
gctctggcgc ttcgtcgcaa tcagactctg ctcactttgc acagcctgaa tatgctgcat      960
tctcgcggtt tcctcgcgga agttttcggc atcctcgcgc ggcataatat ttcggtagac     1020
ttaatcacca cgtcagaagt gagcgtggca ttaacccttg ataccaccgg ttcaacctcc     1080
actggcgata cgttgctgac gcaatctctg ctgatggagc tttccgcact gtgtcgggtg     1140
gaggtggaag aaggtctggc gctggtcgcg ttgattggca atgacctgtc aaaagcctgc     1200
ggcgttggca agaggtatt cggcgtactg gaaccgttca acattcgcat gatttgttat      1260
ggcgcatcca gccataacct gtgcttcctg gtgcccggcg aagatgccga gcaggtggtg     1320
caaaaactgc atagtaattt gtttgagtaa                                      1350
```

<210> SEQ ID NO 28
<211> LENGTH: 34
<212> TYPE: DNA
<213> ORGANISM: Artificial Sequence
<220> FEATURE:
<223> OTHER INFORMATION: Synthetic Construct - Primer for amplification

<400> SEQUENCE: 28

```
gcgtttgccg aagcggcaaa gatggccact tttg                                    34
```

<210> SEQ ID NO 29
<211> LENGTH: 34
<212> TYPE: DNA
<213> ORGANISM: Artificial Sequence
<220> FEATURE:
<223> OTHER INFORMATION: Synthetic Construct - Primer for amplification

<400> SEQUENCE: 29

```
caaaagtggc catctttgcc gcttcggcaa acgc                                    34
```

<210> SEQ ID NO 30
<211> LENGTH: 35
<212> TYPE: DNA
<213> ORGANISM: Artificial Sequence
<220> FEATURE:
<223> OTHER INFORMATION: Synthetic Construct - Primer for amplification

<400> SEQUENCE: 30

```
ggtagatcta atcaccatgt cagaagtgag cgtgg                                   35
```

```
<210> SEQ ID NO 31
<211> LENGTH: 35
<212> TYPE: DNA
<213> ORGANISM: Artificial Sequence
<220> FEATURE:
<223> OTHER INFORMATION: Synthetic Construct - Primer for amplification

<400> SEQUENCE: 31
ccacgctcac ttctgacatg gtgattagat ctacc                              35

<210> SEQ ID NO 32
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 32
ggtagatcta atcaccacgt tagaagtgag cgtggc                             36

<210> SEQ ID NO 33
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 33
gccacgctca cttctaacgt ggtgattaga tctacc                             36

<210> SEQ ID NO 34
<211> LENGTH: 35
<212> TYPE: DNA
<213> ORGANISM: Artificial Sequence
<220> FEATURE:
<223> OTHER INFORMATION: Synthetic Construct - Primer for amplification

<400> SEQUENCE: 34
ggtagatcta atcaccatgt cagaagtgag cgtgg                              35

<210> SEQ ID NO 35
<211> LENGTH: 35
<212> TYPE: DNA
<213> ORGANISM: Artificial Sequence
<220> FEATURE:
<223> OTHER INFORMATION: Synthetic Construct - Primer for amplification

<400> SEQUENCE: 35
ccacgctcac ttctgacatg gtgattagat ctacc                              35

<210> SEQ ID NO 36
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 36
gtcagaagtg agcgtggcat taattctaga taccac                             36

<210> SEQ ID NO 37
<211> LENGTH: 36
<212> TYPE: DNA
<213> ORGANISM: Artificial Sequence
<220> FEATURE:
<223> OTHER INFORMATION: Synthetic Construct - Primer for amplification
```

<400> SEQUENCE: 37

```
gtggtatcta gaattaatgc cacgctcact tctgac                                  36
```

<210> SEQ ID NO 38
<211> LENGTH: 1350
<212> TYPE: DNA
<213> ORGANISM: Escherichia coli

<400> SEQUENCE: 38

```
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag gactggaacc tggcgagcga     180
ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca tggcggcctg     360
atgtcgaccc tgctgtttgt tgagatcctg cgcgaacgcg atgttcaggc acagtggttt     420
gatgtacgta agtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cgggcatcta caccaccgat ccacgcgtag tttccgcagc aaaacgcatt     720
gatgaaatcg cgtttgccga agcggcaaag atggccactt tggtgcaaaa agtactgcat     780
ccggcaacgt tgctacccgc agtacgcagc gatatcccgg tctttgtcgg ctccagcaaa     840
gacccacgcg caggtggtac gctggtgtgc aataaaactg aaaatccgcc gctgttccgc     900
gctctggcgc ttcgtcgcaa tcagactctg ctcactttgc acagcctgaa tatgctgcat     960
tctcgcggtt tcctcgcgga agttttcggc atcctcgcgc ggcataatat tcggtagac    1020
ttaatcacca cgtcagaagt gagcgtggca ttaacccttg ataccaccgg ttcaacctcc    1080
actggcgata cgttgctgac gcaatctctg ctgatggagc tttccgcact gtgtcgggtg    1140
gaggtggaag aaggtctggc gctggtcgcg ttgattggca atgacctgtc aaaagcctgc    1200
ggcgttggca agaggtatt cggcgtactg gaaccgttca acattcgcat gatttgttat    1260
ggcgcatcca gccataacct gtgcttcctg gtgcccggcg aagatgccga gcaggtggtg    1320
caaaaactgc atagtaattt gtttgagtaa                                     1350
```

<210> SEQ ID NO 39
<211> LENGTH: 449
<212> TYPE: PRT
<213> ORGANISM: Escherichia coli

<400> SEQUENCE: 39

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
```

```
              65                  70                  75                  80
Pro Asn Val Ile Arg Glu Glu Ile Glu Arg Leu Leu Glu Asn Ile Thr
                        85                  90                  95

Val Leu Ala Glu Ala Ala Ala Leu Ala Thr Ser Pro Ala Leu Thr Asp
                100                 105                 110

Glu Leu Val Ser His Gly Gly Leu Met Ser Thr Leu Leu Phe Val Glu
                115                 120                 125

Ile Leu Arg Glu Arg Asp Val Gln Ala Gln Trp Phe Asp Val Arg Lys
            130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Lys Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 40
<211> LENGTH: 1350
<212> TYPE: DNA
<213> ORGANISM: Escherichia coli
```

<400> SEQUENCE: 40

```
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag gactggaacc tggcgagcga     180
ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca tggcggcctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cgggcatcta caccaccgat ccacgcgtag tttccgcagc aaaacgcatt     720
gatgaaatcg cgtttgccga agcggcagag atggcaactt ttggtgcaaa agtactgcat     780
ccggcaacgt tgctacccgc agtacgcagc gatatcccgg tctttgtcgg ctccagcaaa     840
gacccacgcg caggtggtac gctggtgtgc aataaaactg aaaatccgcc gctgttccgc     900
gctctggcgc ttcgtcgcaa tcagactctg ctcactttgc acagcctgaa atgctgcat      960
tctcgcggtt cctcgcgga agttttcggc atcctcgcgc ggcataatat tcggtagat    1020
ctaatcacca tgtcagaagt gagcgtggca ttaaccccttg ataccaccgg ttcaacctcc    1080
actggcgata cgttgctgac gcaatctctg ctgatggagc tttccgcact gtgtcgggtg    1140
gaggtggaag aaggtctggc gctggtcgcg ttgattggca atgacctgtc aaaagcctgc    1200
ggcgttggca agaggtatt cggcgtactg gaaccgttca acattcgcat gatttgttat    1260
ggcgcatcca gccataacct gtgcttcctg gtgcccggcg aagatgccga gcaggtggtg    1320
caaaaactgc atagtaattt gtttgagtaa                                     1350
```

<210> SEQ ID NO 41
<211> LENGTH: 449
<212> TYPE: PRT
<213> ORGANISM: Escherichia coli

<400> SEQUENCE: 41

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Gly Leu Met Ser Thr Leu Leu Phe Val Glu
        115                 120                 125
```

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Pro Arg Leu Asn Glu
            165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Met Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 42
<211> LENGTH: 1350
<212> TYPE: DNA
<213> ORGANISM: Escherichia coli

<400> SEQUENCE: 42
atgtctgaaa ttgttgtctc caaatttggc ggtaccagcg tagctgattt tgacgccatg     60
aaccgcagcg ctgatattgt gctttctgat gccaacgtgc gtttagttgt cctctcggct    120
tctgctggta tcactaatct gctggtcgct ttagctgaag gactggaacc tggcgagcga    180
ttcgaaaaac tcgacgctat ccgcaacatc cagtttgcca ttctggaacg tctgcgttac    240

-continued

| | |
|---|---|
| ccgaacgtta tccgtgaaga gattgaacgt ctgctggaga acattactgt tctggcagaa | 300 |
| gcggcggcgc tggcaacgtc tccggcgctg acagatgagc tggtcagcca tggcggcctg | 360 |
| atgtcgaccc tgctgtttgt tgagatcctg cgcgaacgcg atgttcaggc acagtggttt | 420 |
| gatgtacgta aagtgatgcg taccaacgac cgatttggtc gtgcagagcc agatatagcc | 480 |
| gcgctggcgg aactggccgc gctgcagctg ctcccacgtc tcaatgaagg cttagtgatc | 540 |
| acccagggat ttatcggtag cgaaaataaa ggtcgtacaa cgacgcttgg ccgtggaggc | 600 |
| agcgattata cggcagcctt gctggcggag gctttacacg catctcgtgt tgatatctgg | 660 |
| accgacgtcc cgggcatcta caccaccgat ccacgcgtag tttccgcagc aaaacgcatt | 720 |
| gatgaaatcg cgtttgccga agcggcagag atggcaactt ttggtgcaaa agtactgcat | 780 |
| ccggcaacgt tgctacccgc agtacgcagc gatatcccgg tctttgtcgg ctccagcaaa | 840 |
| gacccacgcg caggtggtac gctggtgtgc aataaaactg aaaatccgcc gctgttccgc | 900 |
| gctctggcgc ttcgtcgcaa tcagactctg ctcactttgc acagcctgaa tatgctgcat | 960 |
| tctcgcggtt tcctcgcgga gttttcggc atcctcgcgc ggcataatat ttcggtagac | 1020 |
| ttaatcacca cgtcagaagt gagcgtggca ttaattctag ataccaccgg ttcaacctcc | 1080 |
| actggcgata cgttgctgac gcaatctctg ctgatggagc tttccgcact gtgtcgggtg | 1140 |
| gaggtggaag aaggtctggc gctggtcgcg ttgattggca atgacctgtc aaaagcctgc | 1200 |
| ggcgttggca agaggtatt cggcgtactg gaaccgttca acattcgcat gatttgttat | 1260 |
| ggcgcatcca gccataacct gtgcttcctg gtgcccggcg aagatgccga gcaggtggtg | 1320 |
| caaaaactgc atagtaattt gtttgagtaa | 1350 |

<210> SEQ ID NO 43
<211> LENGTH: 449
<212> TYPE: PRT
<213> ORGANISM: Escherichia coli

<400> SEQUENCE: 43

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Gly Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

-continued

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Ile
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 44
<211> LENGTH: 1350
<212> TYPE: DNA
<213> ORGANISM: Escherichia coli

<400> SEQUENCE: 44

```
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag gactgaaacc tggcgagcga     180
ttcgaaaaac tcgacgctat ccgcaacatc cagtttgcca ttctggaacg tctgcgttac     240
ccgaacgtta tccgtgaaga gattgaacgt ctgctggaga cattactgt tctggcagaa     300 gcggcggcgc tggcaacgtc tccggcgctg acagatgagc tggtcagcca tggcggcctg     360
atgtcgaccc tgctgtttgt tgagatcctg cgcgaacgcg atgttcaggc acagtggttt     420
gatgtacgta agtgatgcg taccaacgac cgatttggtc gtgcagagcc agatatagcc     480
gcgctggcgg aactggccgc gctgcagctg ctcccacgtc tcaatgaagg cttagtgatc     540
```

-continued

```
acccagggat ttatcggtag cgaaaataaa ggtcgtacaa cgacgcttgg ccgtggaggc      600
agcgattata cggcagcctt gctggcggag gctttacacg catctcgtgt tgatatctgg      660
accgacgtcc cgggcatcta caccaccgat ccacgcgtag tttccgcagc aaaacgcatt      720
gatgaaatcg cgtttgccga agcggcagag atggcaactt ttggtgcaaa agtactgcat      780
ccggcaacgt tgctacccgc agtacgcagc gatatcccgg tctttgtcgg ctccagcaaa      840
gacccacgcg caggtggtac gctggtgtgc aataaaactg aaaatccgcc gctgttccgc      900
gctctggcgc ttcgtcgcaa tcagactctg ctcactttgc acagcctgaa atatgctgcat     960 tctcgcggtt tcctcgcgga agttttcggc atcctcgcgc ggcataatat ttcggtagat     1020
ctaatcacca cgttagaagt gagcgtggca ttaacccttg ataccaccgg ttcaacctcc     1080
actggcgata cgttgctgac gcaatctctg ctgatggagc tttccgcact gtgtcgggtg     1140
gaggtggaag aaggtctggc gctggtcgcg ttgattggca atgacctgtc aaaagcctgc     1200
ggcgttggca agaggtatt cggcgtactg gaaccgttca acattcgcat gatttgttat      1260
ggcgcatcca gccataacct gtgcttcctg gtgcccggcg aagatgccga gcaggtggtg     1320
caaaaactgc atagtaattt gtttgagtaa                                      1350
```

<210> SEQ ID NO 45
<211> LENGTH: 449
<212> TYPE: PRT
<213> ORGANISM: Escherichia coli

<400> SEQUENCE: 45

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Gly Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
```

```
            225                 230                 235                 240
Asp Glu Ile Ala Phe Ala Glu Ala Ala Glu Met Ala Thr Phe Gly Ala
                245                 250                 255
Lys Val Leu His Pro Ala Thr Leu Leu Pro Ala Val Arg Ser Asp Ile
            260                 265                 270
Pro Val Phe Val Gly Ser Ser Lys Asp Pro Arg Ala Gly Gly Thr Leu
        275                 280                 285
Val Cys Asn Lys Thr Glu Asn Pro Pro Leu Phe Arg Ala Leu Ala Leu
    290                 295                 300
Arg Arg Asn Gln Thr Leu Leu Thr Leu His Ser Leu Asn Met Leu His
305                 310                 315                 320
Ser Arg Gly Phe Leu Ala Glu Val Phe Gly Ile Leu Ala Arg His Asn
            325                 330                 335
Ile Ser Val Asp Leu Ile Thr Thr Leu Glu Val Ser Val Ala Leu Thr
        340                 345                 350
Leu Asp Thr Thr Gly Ser Thr Ser Thr Gly Asp Thr Leu Leu Thr Gln
    355                 360                 365
Ser Leu Leu Met Glu Leu Ser Ala Leu Cys Arg Val Glu Val Glu Glu
370                 375                 380
Gly Leu Ala Leu Val Ala Leu Ile Gly Asn Asp Leu Ser Lys Ala Cys
385                 390                 395                 400
Gly Val Gly Lys Glu Val Phe Gly Val Leu Glu Pro Phe Asn Ile Arg
            405                 410                 415
Met Ile Cys Tyr Gly Ala Ser Ser His Asn Leu Cys Phe Leu Val Pro
            420                 425                 430
Gly Glu Asp Ala Glu Gln Val Val Gln Lys Leu His Ser Asn Leu Phe
        435                 440                 445
Glu

<210> SEQ ID NO 46
<211> LENGTH: 35
<212> TYPE: DNA
<213> ORGANISM: Artificial Sequence
<220> FEATURE:
<223> OTHER INFORMATION: Synthetic Construct - Primer for amplification

<400> SEQUENCE: 46
tataatgcta gcatgaaaaa tgttggtttt atcgg                          35

<210> SEQ ID NO 47
<211> LENGTH: 31
<212> TYPE: DNA
<213> ORGANISM: Artificial Sequence
<220> FEATURE:
<223> OTHER INFORMATION: Synthetic Construct - Primer for amplification

<400> SEQUENCE: 47
tataatggat ccttacgcca gttgacgaag c                              31

<210> SEQ ID NO 48
<211> LENGTH: 1104
<212> TYPE: DNA
<213> ORGANISM: Escherichia coli

<400> SEQUENCE: 48
atgaaaaatg ttggttttat cggctggcgc ggtatggtcg gctccgttct catgcaacgc    60
atggttgaag agcgcgactt cgacgccatt cgccctgtct tctttctac ttctcagctt   120
```

```
ggccaggctg cgccgtcttt tggcggaacc actggcacac ttcaggatgc ctttgatctg      180
gaggcgctaa aggccctcga tatcattgtg acctgtcagg gcggcgatta taccaacgaa      240
atctatccaa agcttcgtga agcggatgg caaggttact ggattgacgc agcatcgtct      300
ctgcgcatga agatgacgc catcatcatt cttgaccccg tcaatcagga cgtcattacc      360
gacggattaa ataatggcat caggactttt gttggcggta actgtaccgt aagcctgatg      420
ttgatgtcgt tgggtggttt attcgccaat gatcttgttg attgggtgtc cgttgcaacc      480
taccaggccg cttccggcgg tggtgcgcga catatgcgtg agttattaac ccagatgggc      540
catctgtatg gccatgtggc agatgaactc gcgaccccgt cctctgctat tctcgatatc      600
gaacgcaaag tcacaacctt aacccgtagc ggtgagctgc cggtggataa ctttggcgtg      660
ccgctggcgg gtagcctgat tccgtggatc gacaaacagc tcgataacgg tcagagccgc      720
gaagagtgga agggcaggc ggaaaccaac aagatcctca acacatcttc cgtaattccg      780
gtagatggtt tatgtgtgcg tgtcgggca ttgcgctgcc acagccaggc attcactatt      840
aaattgaaaa aagatgtgtc tattccgacc gtggaagaac tgctggctgc gcacaatccg      900
tgggcgaaag tcgttccgaa cgatcggaa atcactatgc gtgagctaac cccagctgcc      960
gttaccggca cgctgaccac gccggtaggc cgcctgcgta agctgaatat gggaccagag     1020
ttcctgtcag cctttaccgt gggcgaccag ctgctgtggg gggccgcgga ccgctgcgt     1080
cggatgcttc gtcaactggc gtaa                                             1104

<210> SEQ ID NO 49
<211> LENGTH: 367
<212> TYPE: PRT
<213> ORGANISM: Escherichia coli

<400> SEQUENCE: 49

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
```

```
            195                 200                 205
Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
                260                 265                 270

Cys His Ser Gln Ala Phe Thr Ile Lys Leu Lys Lys Asp Val Ser Ile
                275                 280                 285

Pro Thr Val Glu Glu Leu Leu Ala Ala His Asn Pro Trp Ala Lys Val
                290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
                340                 345                 350

Trp Gly Ala Ala Glu Pro Leu Arg Arg Met Leu Arg Gln Leu Ala
                355                 360                 365
```

<210> SEQ ID NO 50
<211> LENGTH: 45
<212> TYPE: DNA
<213> ORGANISM: Artificial Sequence
<220> FEATURE:
<223> OTHER INFORMATION: Synthetic Construct - Primer for amplification
<220> FEATURE:
<221> NAME/KEY: misc_feature
<222> LOCATION: (24)..(26)
<223> OTHER INFORMATION: nnn encoding anyone of the other 19 naturally
      existing proteinogenic amino acids, except glutamine

<400> SEQUENCE: 50
agctcgataa cggtcagagt cgannngagt ggaaagggca ggcgg                45

<210> SEQ ID NO 51
<211> LENGTH: 45
<212> TYPE: DNA
<213> ORGANISM: Artificial Sequence
<220> FEATURE:
<223> OTHER INFORMATION: Synthetic Construct - Primer for amplification
<220> FEATURE:
<221> NAME/KEY: misc_feature
<222> LOCATION: (20)..(22)
<223> OTHER INFORMATION: nnn encoding anyone of the other 19 naturally
      existing proteinogenic amino acids, except glutamine

<400> SEQUENCE: 51
ccgcctgccc tttccactcn nntcgactct gaccgttatc gagct                45

<210> SEQ ID NO 52
<211> LENGTH: 37
<212> TYPE: DNA
<213> ORGANISM: Artificial Sequence
<220> FEATURE:
<223> OTHER INFORMATION: Synthetic Construct - Primer for amplification

<400> SEQUENCE: 52
ttttgttggc ggtaactgta acgtgtccct gatgttg                          37

<210> SEQ ID NO 53
<211> LENGTH: 37
<212> TYPE: DNA
<213> ORGANISM: Artificial Sequence
<220> FEATURE:
<223> OTHER INFORMATION: Synthetic Construct - Primer for amplification

<400> SEQUENCE: 53
caacatcagg gacacgttac agttaccgcc aacaaaa					37

<210> SEQ ID NO 54
<211> LENGTH: 367
<212> TYPE: PRT
<213> ORGANISM: Escherichia coli

<400> SEQUENCE: 54

```
Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Ala Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320
```

Val Thr Gly Thr Leu Thr Thr Pro Val Gly Arg Leu Arg Lys Leu Asn
            325                 330                 335

Met Gly Pro Glu Phe Leu Ser Ala Phe Thr Val Gly Asp Gln Leu Leu
        340                 345                 350

Trp Gly Ala Ala Glu Pro Leu Arg Arg Met Leu Arg Gln Leu Ala
    355                 360                 365

<210> SEQ ID NO 55
<211> LENGTH: 1104
<212> TYPE: DNA
<213> ORGANISM: Escherichia coli

<400> SEQUENCE: 55

```
atgaaaaatg ttggttttat cggctggcgc ggtatggtcg gctccgttct catgcaacgc      60
atggttgaag agcgcgactt cgacgccatt cgccctgtct tcttttctac ttctcagctt     120
ggccaggctg cgccgtcttt tggcggaacc actggcacac ttcaggatgc ctttgatctg     180
gaggcgctaa aggccctcga tatcattgtg acctgtcagg gcggcgatta taccaacgaa     240
atctatccaa agcttcgtga agcggatgg caaggttact ggattgacgc agcatcgtct      300
ctgcgcatga agatgacgc catcatcatt cttgaccccg tcaatcagga cgtcattacc      360
gacggattaa ataatggcat caggactttt gttggcggta actgtaccgt aagcctgatg     420
ttgatgtcgt tgggtggttt attcgccaat gatcttgttg attgggtgtc cgttgcaacc     480
taccaggccg cttccggcgg tggtgcgcga catatgcgtg agttattaac ccagatgggc     540
catctgtatg gccatgtggc agatgaactc gcgaccccgt cctctgctat tctcgatatc     600
gaacgcaaag tcacaacctt aaccccgtagc ggtgagctgc cggtggataa ctttggcgtg    660
ccgctggcgg gtagcctgat tccgtggatc gacaaacagc tcgataacgg tcagagtcga     720
gctgagtgga agggcaggc ggaaaccaac aagatcctca acacatcttc cgtaattccg      780
gtagatggtt tatgtgtgcg tgtcggggca ttgcgctgcc acagccaggc attcactatt     840
aaattgaaaa aagatgtgtc tattccgacc gtggaagaac tgctggctgc gcacaatccg     900
tgggcgaaag tcgttccgaa cgatcgggaa atcactatgc gtgagctaac cccagctgcc     960
gttaccggca cgctgaccac gccggtaggc cgcctgcgta agctgaatat gggaccagag    1020
ttcctgtcag cctttaccgt gggcgaccag ctgctgtggg gggccgcgga gccgctgcgt    1080
cggatgcttc gtcaactggc gtaa                                           1104
```

<210> SEQ ID NO 56
<211> LENGTH: 367
<212> TYPE: PRT
<213> ORGANISM: Escherichia coli

<400> SEQUENCE: 56

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp

|   |   |   | 85 |   |   |   |   | 90 |   |   |   |   | 95 |   |   |
|---|---|---|---|---|---|---|---|---|---|---|---|---|---|---|---|

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
            115                 120                 125

Thr Phe Val Gly Gly Asn Cys Thr Val Ser Leu Met Leu Met Ser Leu
            130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
            195                 200                 205

Arg Ser Gly Glu Leu Pro Val Asp Asn Phe Gly Val Pro Leu Ala Gly
210                 215                 220

Ser Leu Ile Pro Trp Ile Asp Lys Gln Leu Asp Asn Gly Gln Ser Arg
225                 230                 235                 240

Cys Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
            275                 280                 285

Pro Thr Val Glu Glu Leu Leu Ala Ala His Asn Pro Trp Ala Lys Val
290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
            355                 360                 365

<210> SEQ ID NO 57
<211> LENGTH: 1104
<212> TYPE: DNA
<213> ORGANISM: Escherichia coli

<400> SEQUENCE: 57

```
atgaaaaatg ttggttttat cggctggcgc ggtatggtcg ctccgttct  catgcaacgc      60 atggttgaag agcgcgactt cgacgccatt cgccctgtct tcttttctac ttctcagctt     120
ggccaggctg cgccgtcttt tggcggaacc actggcacac ttcaggatgc ctttgatctg     180
gaggcgctaa aggccctcga tatcattgtg acctgtcagg gcggcgatta taccaacgaa     240
atctatccaa agcttcgtga agcggatggc caaggttact ggattgacgc agcatcgtct     300
ctgcgcatga agatgacgc catcatcatt cttgaccccg tcaatcagga cgtcattacc     360
gacggattaa ataatggcat caggactttt gttggcggta actgtaccgt aagcctgatg     420
ttgatgtcgt tgggtggttt attcgccaat gatcttgttg attgggtgtc cgttgcaacc     480
taccaggccg cttccggcgg tgctcgcgcg catatgcgtg agttattaac ccagatgggc     540
```

-continued

```
catctgtatg gccatgtggc agatgaactc gcgaccccgt cctctgctat tctcgatatc      600
gaacgcaaag tcacaacctt aacccgtagc ggtgagctgc cggtggataa ctttggcgtg      660
ccgctggcgg gtagcctgat tccgtggatc gacaaacagc tcgataacgg tcagagtcga      720
tgtgagtgga agggcaggc ggaaaccaac aagatcctca acacatcttc cgtaattccg       780
gtagatggtt tatgtgtgcg tgtcggggca ttgcgctgcc acagccaggc attcactatt      840
aaattgaaaa aagatgtgtc tattccgacc gtggaagaac tgctggctgc gcacaatccg      900
tgggcgaaag tcgttccgaa cgatcgggaa atcactatgc gtgagctaac cccagctgcc      960
gttaccggca cgctgaccac gccggtaggc cgcctgcgta agctgaatat gggaccagag      1020
ttcctgtcag cctttaccgt gggcgaccag ctgctgtggg gggccgcgga gccgctgcgt      1080
cggatgcttc gtcaactggc gtaa                                             1104
```

<210> SEQ ID NO 58
<211> LENGTH: 367
<212> TYPE: PRT
<213> ORGANISM: Escherichia coli

<400> SEQUENCE: 58

```
Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Gly Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270
```

Cys His Ser Gln Ala Phe Thr Ile Lys Leu Lys Lys Asp Val Ser Ile
            275                 280                 285

Pro Thr Val Glu Glu Leu Leu Ala Ala His Asn Pro Trp Ala Lys Val
        290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
            325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
            355                 360                 365

<210> SEQ ID NO 59
<211> LENGTH: 1104
<212> TYPE: DNA
<213> ORGANISM: Escherichia coli

<400> SEQUENCE: 59
atgaaaaatg ttggttttat cggctggcgc ggtatggtcg gctccgttct catgcaacgc     60
atggttgaag agcgcgactt cgacgccatt cgccctgtct tcttttctac ttctcagctt    120
ggccaggctg cgccgtcttt tggcggaacc actggcacac ttcaggatgc ctttgatctg    180
gaggcgctaa aggccctcga tatcattgtg acctgtcagg cggcgattta accaacgaa    240 atctatccaa agcttcgtga agcggatggc aaggttact ggattgacgc agcatcgtct    300
ctgcgcatga agatgacgc catcatcatt cttgacccc tcaatcagga cgtcattacc    360
gacggattaa ataatggcat caggactttt gttggcggta actgtaccgt aagcctgatg    420
ttgatgtcgt tggtggtttt attcgccaat gatcttgttg attgggtgtc cgttgcaacc    480
taccaggccg cttccggcgg tggtgcgcga catatgcgtg agttattaac ccagatgggc    540
catctgtatg ccatgtggc agatgaactc gcgaccccgt cctctgctat tctcgatatc    600
gaacgcaaag tcacaacctt aacccgtagc ggtgagctgc cggtggataa ctttggcgtg    660
ccgctggcgg gtagcctgat tccgtggatc gacaaacagc tcgataacgg tcagagtcga    720 gggggagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac cccagctgcc    960
gttaccggca cgctgaccac gccggtaggc cgcctgcgta agctgaatat gggaccagag   1020
ttcctgtcag cctttaccgt gggcgaccag ctgctgtggg gggccgcgga gccgctgcgt   1080
cggatgcttc gtcaactggc gtaa                                          1104

<210> SEQ ID NO 60
<211> LENGTH: 367
<212> TYPE: PRT
<213> ORGANISM: Escherichia coli

<400> SEQUENCE: 60

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly

```
            35                  40                  45
Gly Thr Thr Gly Thr Leu Gln Asp Ala Phe Asp Leu Glu Ala Leu Lys
 50                  55                  60

Ala Leu Asp Ile Ile Val Thr Cys Gln Gly Gly Asp Tyr Thr Asn Glu
 65                  70                  75                  80

Ile Tyr Pro Lys Leu Arg Glu Ser Gly Trp Gln Gly Tyr Trp Ile Asp
                 85                  90                  95

Ala Ala Ser Ser Leu Arg Met Lys Asp Asp Ala Ile Ile Ile Leu Asp
             100                 105                 110

Pro Val Asn Gln Asp Val Ile Thr Asp Gly Leu Asn Asn Gly Ile Arg
         115                 120                 125

Thr Phe Val Gly Gly Asn Cys Thr Val Ser Leu Met Leu Met Ser Leu
130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
             180                 185                 190

Pro Ser Ser Ala Ile Leu Asp Ile Glu Arg Lys Val Thr Thr Leu Thr
         195                 200                 205

Arg Ser Gly Glu Leu Pro Val Asp Asn Phe Gly Val Pro Leu Ala Gly
210                 215                 220

Ser Leu Ile Pro Trp Ile Asp Lys Gln Leu Asp Asn Gly Gln Ser Arg
225                 230                 235                 240

His Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
             260                 265                 270

Cys His Ser Gln Ala Phe Thr Ile Lys Leu Lys Asp Val Ser Ile
         275                 280                 285

Pro Thr Val Glu Glu Leu Leu Ala Ala His Asn Pro Trp Ala Lys Val
290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
             340                 345                 350

Trp Gly Ala Ala Glu Pro Leu Arg Arg Met Leu Arg Gln Leu Ala
         355                 360                 365

<210> SEQ ID NO 61
<211> LENGTH: 1104
<212> TYPE: DNA
<213> ORGANISM: Escherichia coli

<400> SEQUENCE: 61
atgaaaaatg ttggttttat cggctggcgc ggtatggtcg gctccgttct catgcaacgc      60
atggttgaag agcgcgactt cgacgccatt cgccctgtct tcttttctac ttctcagctt    120
ggccaggctg cgccgtcttt tggcggaacc actggcacac ttcaggatgc ctttgatctg    180
gaggcgctaa aggccctcga tatcattgtg acctgtcagg gcggcgatta taccaacgaa    240
atctatccaa agcttcgtga aagcggatgg caaggttact ggattgacgc agcatcgtct    300
```

-continued

```
ctgcgcatga aagatgacgc catcatcatt cttgaccccg tcaatcagga cgtcattacc    360
gacggattaa ataatggcat caggactttt gttggcggta actgtaccgt aagcctgatg    420
ttgatgtcgt tgggtggttt attcgccaat gatcttgttg attgggtgtc cgttgcaacc    480
taccaggccg cttccggcgg tggtgcgcga catatgcgtg agttattaac ccagatgggc    540
catctgtatg gccatgtggc agatgaactc gcgaccccgt cctctgctat tctcgatatc    600
gaacgcaaag tcacaacctt aacccgtagc ggtgagctgc cggtggataa ctttggcgtg    660
ccgctggcgg gtagcctgat tccgtggatc gacaaacagc tcgataacgg tcagagtcga    720
catgagtgga aagggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac cccagctgcc    960
gttaccggca cgctgaccac gccggtaggc cgcctgcgta agctgaatat gggaccagag   1020
ttcctgtcag ccttttaccgt gggcgaccag ctgctgtggg gggccgcgga ccgctgcgt   1080 cggatgcttc gtcaactggc gtaa                                          1104
```

<210> SEQ ID NO 62
<211> LENGTH: 367
<212> TYPE: PRT
<213> ORGANISM: Escherichia coli

<400> SEQUENCE: 62

```
Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220
```

```
Ser Leu Ile Pro Trp Ile Asp Lys Gln Leu Asp Asn Gly Gln Ser Arg
225                 230                 235                 240

Ile Glu Trp Lys Gly Gln Ala Glu Thr Asn Lys Ile Leu Asn Thr Ser
            245                 250                 255

Ser Val Ile Pro Val Asp Gly Leu Cys Val Arg Val Gly Ala Leu Arg
        260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365
```

<210> SEQ ID NO 63
<211> LENGTH: 1104
<212> TYPE: DNA
<213> ORGANISM: Escherichia coli

<400> SEQUENCE: 63

```
atgaaaaatg ttggttttat cggctggcgc ggtatggtcg gctccgttct catgcaacgc      60
atggttgaag agcgcgactt cgacgccatt cgccctgtct tcttttctac ttctcagctt     120
ggccaggctg cgccgtcttt tggcggaacc actggcacac ttcaggatgc ctttgatctg     180
gaggcgctaa aggccctcga tatcattgtg acctgtcagg gcggcgatta taccaacgaa     240
atctatccaa agcttcgtga agcggatggc aaggttact  ggattgacgc agcatcgtct     300
ctgcgcatga agatgacgc  catcatcatt cttgaccccg tcaatcagga cgtcattacc     360
gacggattaa ataatggcat caggactttt gttggcggta actgtaccgt aagcctgatg     420
ttgatgtcgt tgggtggttt attcgccaat gatcttgttg attgggtgtc cgttgcaacc     480
taccaggccg cttccggcgg tggtgcgcga catatgcgtg agttattaac ccagatgggc     540
catctgtatg gccatgtggc agatgaactc gcgaccccgt cctctgctat tctcgatatc     600
gaacgcaaag tcacaacctt aacccgtagc ggtgagctgc cggtggataa ctttggcgtg     660
ccgctggcgg gtagcctgat ccgtggatc  gacaaacagc tcgataacgg tcagagtcga     720
attgagtgga agggcaggc  ggaaaccaac aagatcctca acacatcttc cgtaattccg     780
gtagatggtt tatgtgtgcg tgtcggggca ttgcgctgcc acagccaggc attcactatt     840
aaaattgaaa aagatgtgtc tattccgacc gtggaagaac tgctggctgc gcacaatccg     900
tgggcgaaag tcgttccgaa cgatcgggaa atcactatgc gtgagctaac cccagctgcc     960
gttaccggca cgctgaccac gccggtaggc cgcctgcgta agctgaatat gggaccagag    1020
ttcctgtcag cctttaccgt gggcgaccag ctgctgtggg gggccgcgga gccgctgcgt    1080
cggatgcttc gtcaactggc gtaa                                           1104
```

<210> SEQ ID NO 64
<211> LENGTH: 367
<212> TYPE: PRT
<213> ORGANISM: Escherichia coli

<400> SEQUENCE: 64

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Met Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365

<210> SEQ ID NO 65
<211> LENGTH: 1104
<212> TYPE: DNA
<213> ORGANISM: Escherichia coli

<400> SEQUENCE: 65

```
atgaaaaatg ttggttttat cggctggcgc ggtatggtcg gctccgttct catgcaacgc      60
atggttgaag agcgcgactt cgacgccatt cgccctgtct tcttttctac ttctcagctt     120
ggccaggctg cgccgtcttt tggcggaacc actggcacac ttcaggatgc ctttgatctg     180
gaggcgctaa aggccctcga tatcattgtg acctgtcagg gcggcgatta taccaacgaa     240
atctatccaa agcttcgtga agcggatgg caaggttact ggattgacgc agcatcgtct     300
ctgcgcatga agatgacgc catcatcatt cttgaccccg tcaatcagga cgtcattacc     360
gacggattaa ataatggcat caggactttt gttggcggta actgtaccgt aagcctgatg     420
ttgatgtcgt tgggtggttt attcgccaat gatcttgttg attgggtgtc cgttgcaacc     480
taccaggccg cttccggcgg tggtgcgcga catatgcgtg agttattaac ccagatgggc     540
catctgtatg ccatgtggc agatgaactc gcgaccccgt cctctgctat tctcgatatc     600
gaacgcaaag tcacaacctt aacccgtagc ggtgagctgc cggtggataa ctttggcgtg     660
ccgctggcgg gtagcctgat tccgtggatc gacaaacagc tcgataacgg tcagagtcga     720
atggagtgga aagggcaggc ggaaaccaac aagatcctca acacatcttc cgtaattccg     780
gtagatggtt tatgtgtgcg tgtcgggca ttgcgctgcc acagccaggc attcactatt     840
aaattgaaaa aagatgtgtc tattccgacc gtggaagaac tgctggctgc gcacaatccg     900
tgggcgaaag tcgttccgaa cgatcgggaa atcactatgc gtgagctaac cccagctgcc     960
gttaccggca cgctgaccac gccggtaggc cgcctgcgta agctgaatat gggaccagag    1020
ttcctgtcag cctttaccgt gggcgaccag ctgctgtggg gggccgcgga ccgctgcgt     1080 cggatgcttc gtcaactggc gtaa                                           1104
```

<210> SEQ ID NO 66
<211> LENGTH: 367
<212> TYPE: PRT
<213> ORGANISM: Escherichia coli

<400> SEQUENCE: 66

```
Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175
```

```
Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Gln Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365

<210> SEQ ID NO 67
<211> LENGTH: 1104
<212> TYPE: DNA
<213> ORGANISM: Escherichia coli

<400> SEQUENCE: 67
atgaaaaatg ttggttttat cggctggcgc ggtatggtcg ctccgttct  catgcaacgc      60
atggttgaag agcgcgactt cgacgccatt cgccctgtct ctttttctac ttctcagctt     120
ggccaggctg cgccgtcttt tggcggaacc actggcacac ttcaggatgc ctttgatctg     180
gaggcgctaa aggccctcga tatcattgtg acctgtcagg cggcgattaa taccaacgaa     240
atctatccaa agcttcgtga agcggatgg  caaggttact ggattgacgc agcatcgtct     300
ctgcgcatga agatgacgc  catcatcatt ctttgacccc gtcaatcagga cgtcattacc     360
gacggattaa ataatggcat caggactttt gttggcggta actgtaccgt aagcctgatg     420
ttgatgtcgt tgggtggttt attcgccaat gatcttgttg attgggtgtc cgttgcaacc     480
taccaggccg cttccggcgg tggtgcgcga catatgcgtg agttattaac ccagatgggc     540
catctgtatg gccatgtggc agatgaactc gcgaccccgt cctctgctat tctcgatatc     600
gaacgcaaag tcacaacctt aacccgtagc ggtgagctgc cggtggataa ctttggcgtg     660
ccgctggcgg gtagcctgat tccgtggatc gacaaacagc tcgataacgg tcagagtcga     720
caggagtgga agggcaggc  ggaaaccaac aagatcctca acacatcttc cgtaattccg     780
gtagatggtt tatgtgtgcg tgtcggggca ttgcgctgcc acagccaggc attcactatt     840
aaaattgaaa aagatgtgtc tattccgacc gtggaagaac tgctggctgc gcacaatccg     900
tgggcgaaag tcgttccgaa cgatcgggaa atcactatgc gtgagctaac cccagctgcc     960
gttaccggca cgctgaccac gccggtaggc cgctgcgta  agctgaatat gggaccagag    1020
ttcctgtcag cctttaccgt gggcgaccag ctgctgtggg gggccgcgga gccgctgcgt    1080
```

-continued

```
cggatgcttc gtcaactggc gtaa                                          1104
```

\<210\> SEQ ID NO 68
\<211\> LENGTH: 367
\<212\> TYPE: PRT
\<213\> ORGANISM: Escherichia coli
\<220\> FEATURE:
\<221\> NAME/KEY: MISC_FEATURE
\<222\> LOCATION: (241)..(241)
\<223\> OTHER INFORMATION: X being any aminoacid other than glutamine

\<400\> SEQUENCE: 68

```
Met Lys Asn Val Gly Phe Ile Gly Trp Arg Gly Met Val Gly Ser Val
1               5                  10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Ala Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Xaa Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
```

```
            340                 345                 350
Trp Gly Ala Ala Glu Pro Leu Arg Arg Met Leu Arg Gln Leu Ala
        355                 360                 365
```

<210> SEQ ID NO 69
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 69
tataatgcta gcatgaaagc tgcagtactt ca                                    32

<210> SEQ ID NO 70
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 70
tataatgaat tcttacggga ttatgagact tc                                    32

<210> SEQ ID NO 71
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 71
tataatgcta gcatgcctgc tacgttaaag aa                                    32

<210> SEQ ID NO 72
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 72
tataatgagc tctcattgga aaattgggaa gg                                    32

<210> SEQ ID NO 73
<211> LENGTH: 939
<212> TYPE: DNA
<213> ORGANISM: Saccharomyces cerevisiae

<400> SEQUENCE: 73
atgcctgcta cgttaaagaa ttcttctgct acattaaaac taaatactgg tgcctccatt      60
ccagtgttgg gtttcggcac ttggcgttcc gttgacaata acggttacca ttctgtaatt     120
gcagctttga agctggata cagacacatt gatgctgcgg ctatctattt gaatgaagaa     180
gaagttggca gggctattaa agattccgga gtccctcgtg aggaaatttt tattactact     240
aagctttggg gtacggaaca acgtgatccg gaagctgctc taaacaagtc tttgaaagaa     300
ctaggcttga ttatgttga cctatatctg atgcattggc cagtgccttt gaaaaccgac     360
agagttactg atggtaacgt tctgtgcatt ccaacattag aagatggcac tgttgacatc     420
gatactaagg aatggaattt tatcaagacg tgggagttga tgcaagagtt gccaaagacg     480
ggcaaaacta agccgttggg tgtctctaat tttctatta acaacattaa agaattatta     540

```
gaatctccaa ataacaaggt ggtaccagct actaatcaaa ttgaaattca tccattgcta    600
ccacaagacg aattgattgc cttttgtaag gaaaagggta ttgttgttga agcctactca    660
ccatttggga gtgctaatgc tcctttacta aaagagcaag caattattga tatggctaaa    720
aagcacggcg ttgagccagc acagcttatt atcagttgga gtattcaaag aggctacgtt    780
gttctggcca atcggttaa tcctgaaaga attgtatcca attttaagat tttcactctg    840
cctgaggatg atttcaagac tattagtaac ctatccaaag tgcatggtac aaagagagtc    900
gttgatatga agtggggatc cttcccaatt ttccaatga                          939
```

<210> SEQ ID NO 74
<211> LENGTH: 312
<212> TYPE: PRT
<213> ORGANISM: Saccharomyces cerevisiae

<400> SEQUENCE: 74

```
Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
                20                  25                  30

Asn Asn Gly Tyr His Ser Val Ile Ala Ala Leu Lys Ala Gly Tyr Arg
            35                  40                  45

His Ile Asp Ala Ala Ala Ile Tyr Leu Asn Glu Glu Glu Val Gly Arg
        50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Ala Ala Leu Asn Lys
                85                  90                  95

Ser Leu Lys Arg Leu Gly Leu Asp Tyr Val Asp Leu Tyr Leu Met His
                100                 105                 110

Trp Pro Val Pro Leu Lys Thr Asp Arg Val Thr Asp Gly Asn Val Leu
            115                 120                 125

Cys Ile Pro Thr Leu Glu Asp Gly Thr Val Asp Ile Asp Thr Lys Glu
        130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Val Glu Ala Tyr Ser Pro Phe Gly Ser
    210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
            260                 265                 270

Ser Asn Phe Lys Ile Phe Thr Leu Pro Glu Asp Asp Phe Lys Thr Ile
        275                 280                 285

Ser Asn Leu Ser Lys Val His Gly Thr Lys Arg Val Val Asp Met Lys
    290                 295                 300
```

Trp Gly Ser Phe Pro Ile Phe Gln
305                 310

<210> SEQ ID NO 75
<211> LENGTH: 1083
<212> TYPE: DNA
<213> ORGANISM: Metallosphaera sedula

<400> SEQUENCE: 75

| | | | | | |
|---|---|---|---|---|---|
| atgaaagctg | cagtacttca | tacgtataag | gaaccgctgt | ccattgagga | cgtgaatatc | 60 |
| tcccaaccta | aggctgggga | agtcaagatc | aaggtcaagg | caaccgggct | ctgtcactcc | 120 |
| gacgtcaatg | tctttgaggg | gaaaacccca | gttcctcccc | cagtggttgc | tggacacgaa | 180 |
| atatcaggga | ttgtggagga | agtgggacct | ggggtgacca | gggttaaacc | aggtgatagg | 240 |
| gtgatttcag | cgtttattca | ccctgtggt | aaatgcggta | actgcgttgc | aggaaaggag | 300 |
| aatctgtgtg | agaccttctc | ccaggtcaga | ctcaagggag | taatgccaga | tggaacgtca | 360 |
| aggctgtcaa | aggacggaaa | ggagataagg | actttccttg | gaggcggttt | cgcggagtac | 420 |
| gccattgtgg | gagagaacgc | gctaaccagg | gttccagagg | acatggacct | agagaaggta | 480 |
| gctgtcctag | gttgtgctgg | gttaacaggg | tacggtgcca | tatcatcatc | caagattgag | 540 |
| cctggagaca | ctgtggccgt | gataggcgta | ggaggagtgg | gtttgtccac | aatacaactc | 600 |
| ctaagggcct | cgggtgccgg | gaggataatc | gccgtgggaa | cgaaaaagtg | gaaacttgac | 660 |
| agggccatgg | agctaggtgc | aactgacgtg | gtaaactcga | aggagataga | tcccgtcaaa | 720 |
| gcaataaagg | agatcacggg | tggagggcca | caggtggtga | tagaggctgg | aggaaatgag | 780 |
| gatacgattc | atatggcgct | ggattcagtt | agaattggag | gaaaggtggt | tctggtaggg | 840 |
| ttacctccag | caacggccat | gatacccatc | agggtagcgt | caatagttag | ggaggcata | 900 |
| gaggttgtgg | ggaattacgg | aggaagacct | agggttgata | tgcccaagct | tctcgagcta | 960 |
| gtgaggcagg | gaagatacga | tccgtctagg | cttgtgacgg | gtagattcag | gttggaggaa | 1020 |
| ataaatgagg | cagtcaaaat | gcttgaggaa | ggagaggcca | taagaagtct | cataatcccg | 1080 |
| taa | | | | | | 1083 |

<210> SEQ ID NO 76
<211> LENGTH: 360
<212> TYPE: PRT
<213> ORGANISM: Metallosphaera sedula

<400> SEQUENCE: 76

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
            20                  25                  30

Lys Ala Thr Gly Leu Cys His Ser Asp Val Asn Val Phe Glu Gly Lys
        35                  40                  45

Thr Pro Val Pro Pro Val Ala Gly His Glu Ile Ser Gly Ile
    50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu

```
                115                 120                 125
Ile Arg Thr Phe Leu Gly Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205

Ile Ile Ala Val Gly Thr Lys Lys Trp Lys Leu Asp Arg Ala Met Glu
    210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Pro Gln Val Val Ile Glu Ala
                245                 250                 255

Gly Gly Asn Glu Asp Thr Ile His Met Ala Leu Asp Ser Val Arg Ile
                260                 265                 270

Gly Gly Lys Val Val Leu Val Gly Leu Pro Pro Ala Thr Ala Met Ile
            275                 280                 285

Pro Ile Arg Val Ala Ser Ile Val Arg Gly Gly Ile Glu Val Val Gly
    290                 295                 300

Asn Tyr Gly Gly Arg Pro Arg Val Asp Met Pro Lys Leu Leu Glu Leu
305                 310                 315                 320

Val Arg Gln Gly Arg Tyr Asp Pro Ser Arg Leu Val Thr Gly Arg Phe
                325                 330                 335

Arg Leu Glu Glu Ile Asn Glu Ala Val Lys Met Leu Glu Glu Gly Glu
                340                 345                 350

Ala Ile Arg Ser Leu Ile Ile Pro
            355                 360

<210> SEQ ID NO 77
<211> LENGTH: 37
<212> TYPE: DNA
<213> ORGANISM: Artificial Sequence
<220> FEATURE:
<223> OTHER INFORMATION: Synthetic Construct - Primer for amplification

<400> SEQUENCE: 77
gtcaaggcaa ccggtctctg tcgctccgac gtcaatg                              37

<210> SEQ ID NO 78
<211> LENGTH: 37
<212> TYPE: DNA
<213> ORGANISM: Artificial Sequence
<220> FEATURE:
<223> OTHER INFORMATION: Synthetic Construct - Primer for amplification

<400> SEQUENCE: 78
cattgacgtc ggagcgacag agaccggttg ccttgac                              37

<210> SEQ ID NO 79
<211> LENGTH: 40
<212> TYPE: DNA
<213> ORGANISM: Artificial Sequence
<220> FEATURE:
<223> OTHER INFORMATION: Synthetic Construct - Primer for amplification
```

<400> SEQUENCE: 79
ggctctgtca ctccgacgta catgtctttg aggggaaaac                                    40

<210> SEQ ID NO 80
<211> LENGTH: 40
<212> TYPE: DNA
<213> ORGANISM: Artificial Sequence
<220> FEATURE:
<223> OTHER INFORMATION: Synthetic Construct - Primer for amplification

<400> SEQUENCE: 80
gttttcccct caaagacatg tacgtcggag tgacagagcc                                    40

<210> SEQ ID NO 81
<211> LENGTH: 360
<212> TYPE: PRT
<213> ORGANISM: Metallosphaera sedula

<400> SEQUENCE: 81

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
            20                  25                  30

Lys Ala Thr Gly Leu Cys Arg Ser Asp Val His Val Phe Glu Gly Lys
        35                  40                  45

Thr Pro Val Pro Pro Val Ala Gly His Glu Ile Ser Gly Ile
    50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu
        115                 120                 125

Ile Arg Thr Phe Leu Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205

Ile Ile Ala Val Gly Thr Lys Lys Trp Lys Leu Asp Arg Ala Met Glu
    210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Pro Gln Val Val Ile Glu Ala
                245                 250                 255

Gly Gly Asn Glu Asp Thr Ile His Met Ala Leu Asp Ser Val Arg Ile
            260                 265                 270

Gly Gly Lys Val Val Leu Val Gly Leu Pro Pro Ala Thr Ala Met Ile
        275                 280                 285

Pro Ile Arg Val Ala Ser Ile Val Arg Gly Gly Ile Glu Val Val Gly

Asn Tyr Gly Gly Arg Pro Arg Val Asp Met Pro Lys Leu Leu Glu Leu
305             310                 315                 320

Val Arg Gln Gly Arg Tyr Asp Pro Ser Arg Leu Val Thr Gly Arg Phe
            325                 330                 335

Arg Leu Glu Glu Ile Asn Glu Ala Val Lys Met Leu Glu Glu Gly Glu
            340                 345                 350

Ala Ile Arg Ser Leu Ile Ile Pro
            355                 360

<210> SEQ ID NO 82
<211> LENGTH: 1083
<212> TYPE: DNA
<213> ORGANISM: Metallosphaera sedula

<400> SEQUENCE: 82

| | |
|---|---|
| atgaaagcag cagttctgca tacctataaa gaaccgctga gcattgaaga tgtgaatatt | 60 |
| tcacagccga agccggtga agtgaaaatc aaagttaaag caaccggtct gtgtcgtagt | 120 |
| gatgttcatg tttttgaagg taaaacaccg gttccgcctc cggttgttgc aggtcatgaa | 180 |
| attagcggta ttgttgaaga ggttggtccg gtgttaccc gtgttaaacc gggtgatcgt | 240 |
| gttattagcg catttattca tccgtgtggt aaatgcggta attgtgttgc cggtaaagaa | 300 |
| aatctgtgtg aaacctttag ccaggttcgt ctgaaaggtg ttatgccgga tggcaccagc | 360 |
| cgtctgagca agatggcaa agaaattcgt acctttctgg gtggtggttt tgcagaatat | 420 |
| gcaattgttg gtgaaaatgc actgacccgt gttccggaag atatggatct ggaaaaagtt | 480 |
| gcagttctgg gttgtgccgg tctgaccggt tatggtgcaa ttagcagcag caaaattgaa | 540 |
| cctggtgata ccgttgcagt tattggtgtt ggtggtgtgg gtctgagcac cattcagctg | 600 |
| ctgcgtgcaa gcggtgcagg tcgtattatt gcagttggca ccaaaaaatg gaaactggat | 660 |
| cgtgcaatgg aactgggtgc aaccgatgtt gttaacagta agaaattga tccggtgaaa | 720 |
| gccatcaaag aaatcaccgg tggtggtccg caggttgtta ttgaagccgg tggtaatgaa | 780 |
| gataccattc acatggcact ggatagcgtt cgtattggtg gtaaagttgt tctggttggt | 840 |
| ctgcctccgg caaccgcaat gattccgatt cgtgttgcaa gcattgttcg tggtggtatt | 900 |
| gaagttgttg gtaattatgg tggtcgtccg cgtgttgata tgccgaaact gctggaactg | 960 |
| gttcgtcagg gtcgttatga tccgagccgt ctggttaccg gtcgtttcg tctggaagaa | 1020 |
| attaatgaag ccgtcaaaat gctggaagaa ggtgaagcaa ttcgtagcct gattattccg | 1080 |
| taa | 1083 |

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct - Primer for amplification

<400> SEQUENCE: 83
tataaggatc cgtttaactt taagaaggag atataccatg gg                    42

<210> SEQ ID NO 84
<211> LENGTH: 29
<212> TYPE: DNA
<213> ORGANISM: Artificial Sequence
<220> FEATURE:
<223> OTHER INFORMATION: Synthetic Construct - Primer for amplification

<400> SEQUENCE: 84
tataagaatt cttacgccag ttgacgaag                                          29

<210> SEQ ID NO 85
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 85
tataagcggc cgcgtttaac tttaagaagg agatat                                  36

<210> SEQ ID NO 86
<211> LENGTH: 29
<212> TYPE: DNA
<213> ORGANISM: Artificial Sequence
<220> FEATURE:
<223> OTHER INFORMATION: Synthetic Construct - Primer for amplification

<400> SEQUENCE: 86
tataaactcg agcttacgga ataatcagg                                          29

<210> SEQ ID NO 87
<211> LENGTH: 841
<212> TYPE: PRT
<213> ORGANISM: Escherichia coli

<400> SEQUENCE: 87

Met Lys Asn Leu Arg Leu Cys Arg Arg Ile Phe Ile Ser Thr Lys Gly
1               5                   10                  15

Asn Glu Val Thr Thr Met Arg Val Leu Lys Phe Gly Gly Thr Ser Val
            20                  25                  30

Ala Asn Ala Glu Arg Phe Leu Arg Val Ala Asp Ile Leu Glu Ser Asn
        35                  40                  45

Ala Arg Gln Gly Gln Val Ala Thr Val Leu Ser Ala Pro Ala Lys Ile
    50                  55                  60

Thr Asn His Leu Val Ala Met Ile Glu Lys Thr Ile Ser Gly Gln Asp
65                  70                  75                  80

Ala Leu Pro Asn Ile Ser Asp Ala Glu Arg Ile Phe Ala Glu Leu Leu
                85                  90                  95

Thr Gly Leu Ala Ala Ala Gln Pro Gly Phe Pro Leu Ala Gln Leu Lys
            100                 105                 110

Thr Phe Val Asp Gln Glu Phe Ala Gln Ile Lys His Val Leu His Gly
        115                 120                 125

Ile Ser Leu Leu Gly Gln Cys Pro Asp Ser Ile Asn Ala Ala Leu Ile
    130                 135                 140

Cys Arg Gly Glu Lys Met Ser Ile Ala Ile Met Ala Gly Val Leu Glu
145                 150                 155                 160

Ala Arg Gly His Asn Val Thr Val Ile Asp Pro Val Glu Lys Leu Leu
                165                 170                 175

Ala Val Gly His Tyr Leu Glu Ser Thr Val Asp Ile Ala Glu Ser Thr
            180                 185                 190

Arg Arg Ile Ala Ala Ser Arg Ile Pro Ala Asp His Met Val Leu Met
        195                 200                 205

Ala Gly Phe Thr Ala Gly Asn Glu Lys Gly Glu Leu Val Val Leu Gly
    210                 215                 220

-continued

Arg Asn Gly Ser Asp Tyr Ser Ala Ala Val Leu Ala Ala Cys Leu Arg
225                 230                 235                 240

Ala Asp Cys Cys Glu Ile Trp Thr Asp Val Asp Gly Val Tyr Thr Cys
            245                 250                 255

Asp Pro Arg Gln Val Pro Asp Ala Arg Leu Leu Lys Ser Met Ser Tyr
        260                 265                 270

Gln Glu Ala Met Glu Leu Ser Tyr Phe Gly Ala Lys Val Leu His Pro
    275                 280                 285

Arg Thr Ile Thr Pro Ile Ala Gln Phe Gln Ile Pro Cys Leu Ile Lys
290                 295                 300

Asn Thr Gly Asn Pro Gln Ala Pro Gly Thr Leu Ile Gly Ala Ser Arg
305                 310                 315                 320

Asp Glu Asp Glu Leu Pro Val Lys Gly Ile Ser Asn Leu Asn Asn Met
            325                 330                 335

Ala Met Phe Ser Val Ser Gly Pro Gly Met Lys Gly Met Val Gly Met
        340                 345                 350

Ala Ala Arg Val Phe Ala Ala Met Ser Arg Ala Arg Ile Ser Val Val
    355                 360                 365

Leu Ile Thr Gln Ser Ser Ser Glu Tyr Ser Ile Ser Phe Cys Val Pro
370                 375                 380

Gln Ser Asp Cys Val Arg Ala Glu Arg Ala Met Gln Glu Glu Phe Tyr
385                 390                 395                 400

Leu Glu Leu Lys Glu Gly Leu Leu Glu Pro Leu Ala Val Thr Glu Arg
            405                 410                 415

Leu Ala Ile Ile Ser Val Val Gly Asp Gly Met Arg Thr Leu Arg Gly
        420                 425                 430

Ile Ser Ala Lys Phe Phe Ala Ala Leu Ala Arg Ala Asn Ile Asn Ile
    435                 440                 445

Val Ala Ile Ala Gln Gly Ser Ser Glu Arg Ser Ile Ser Val Val Val
450                 455                 460

Asn Asn Asp Asp Ala Thr Thr Gly Val Arg Val Thr His Gln Met Leu
465                 470                 475                 480

Phe Asn Thr Asp Gln Val Ile Glu Val Phe Val Ile Gly Val Gly Gly
            485                 490                 495

Val Gly Gly Ala Leu Leu Glu Gln Leu Lys Arg Gln Gln Ser Trp Leu
        500                 505                 510

Lys Asn Lys His Ile Asp Leu Arg Val Cys Gly Val Ala Asn Ser Lys
    515                 520                 525

Ala Leu Leu Thr Asn Val His Gly Leu Asn Leu Glu Asn Trp Gln Glu
530                 535                 540

Glu Leu Ala Gln Ala Lys Glu Pro Phe Asn Leu Gly Arg Leu Ile Arg
545                 550                 555                 560

Leu Val Lys Glu Tyr His Leu Leu Asn Pro Val Ile Val Asp Cys Thr
            565                 570                 575

Ser Ser Gln Ala Val Ala Asp Gln Tyr Ala Asp Phe Leu Arg Glu Gly
        580                 585                 590

Phe His Val Val Thr Pro Asn Lys Lys Ala Asn Thr Ser Ser Met Asp
    595                 600                 605

Tyr Tyr His Gln Leu Arg Tyr Ala Ala Glu Lys Ser Arg Arg Lys Phe
610                 615                 620

Leu Tyr Asp Thr Asn Val Gly Ala Gly Leu Pro Val Ile Glu Asn Leu
625                 630                 635                 640

Gln Asn Leu Leu Asn Ala Gly Asp Glu Leu Met Lys Phe Ser Gly Ile

```
                    645                 650                 655
Leu Ser Gly Ser Leu Ser Tyr Ile Phe Gly Lys Leu Asp Glu Gly Met
            660                 665                 670
Ser Phe Ser Glu Ala Thr Thr Leu Ala Arg Glu Met Gly Tyr Thr Glu
            675                 680                 685
Pro Asp Pro Arg Asp Asp Leu Ser Gly Met Asp Val Ala Arg Lys Leu
            690                 695                 700
Leu Ile Leu Ala Arg Glu Thr Gly Arg Glu Leu Glu Leu Ala Asp Ile
705                 710                 715                 720
Glu Ile Glu Pro Val Leu Pro Ala Glu Phe Asn Ala Glu Gly Asp Val
            725                 730                 735
Ala Ala Phe Met Ala Asn Leu Ser Gln Leu Asp Asn Leu Phe Ala Ala
            740                 745                 750
Arg Val Ala Lys Ala Arg Asp Glu Gly Lys Val Leu Arg Tyr Val Gly
            755                 760                 765
Asn Ile Asp Glu Asp Gly Val Cys Arg Val Lys Ile Ala Glu Val Asp
            770                 775                 780
Ser Asn Asp Pro Leu Phe Lys Val Lys Asn Gly Glu Asn Ala Leu Ala
785                 790                 795                 800
Phe Tyr Ser His Tyr Tyr Gln Pro Leu Pro Leu Val Leu Arg Gly Tyr
            805                 810                 815
Gly Ala Gly Asn Asp Val Thr Ala Ala Gly Val Phe Ala Asp Leu Leu
            820                 825                 830
Arg Thr Leu Ser Trp Lys Leu Gly Val
            835                 840

<210> SEQ ID NO 88
<211> LENGTH: 810
<212> TYPE: PRT
<213> ORGANISM: Escherichia coli

<400> SEQUENCE: 88

Met Ser Val Ile Ala Gln Ala Gly Ala Lys Gly Arg Gln Leu His Lys
1               5                   10                  15
Phe Gly Gly Ser Ser Leu Ala Asp Val Lys Cys Tyr Leu Arg Val Ala
            20                  25                  30
Gly Ile Met Ala Glu Tyr Ser Gln Pro Asp Asp Met Met Val Val Ser
            35                  40                  45
Ala Ala Gly Ser Thr Thr Asn Gln Leu Ile Asn Trp Leu Lys Leu Ser
        50                  55                  60
Gln Thr Asp Arg Leu Ser Ala His Gln Val Gln Gln Thr Leu Arg Arg
65                  70                  75                  80
Tyr Gln Cys Asp Leu Ile Ser Gly Leu Leu Pro Ala Glu Glu Ala Asp
            85                  90                  95
Ser Leu Ile Ser Ala Phe Val Ser Asp Leu Glu Arg Leu Ala Ala Leu
            100                 105                 110
Leu Asp Ser Gly Ile Asn Asp Ala Val Tyr Ala Glu Val Val Gly His
            115                 120                 125
Gly Glu Val Trp Ser Ala Arg Leu Met Ser Ala Val Leu Asn Gln Gln
        130                 135                 140
Gly Leu Pro Ala Ala Trp Leu Asp Ala Arg Glu Phe Leu Arg Ala Glu
145                 150                 155                 160
Arg Ala Ala Gln Pro Gln Val Asp Glu Gly Leu Ser Tyr Pro Leu Leu
            165                 170                 175
```

-continued

```
Gln Gln Leu Leu Val Gln His Pro Gly Lys Arg Leu Val Thr Gly
            180                 185                 190
Phe Ile Ser Arg Asn Asn Ala Gly Glu Thr Val Leu Leu Gly Arg Asn
        195                 200                 205
Gly Ser Asp Tyr Ser Ala Thr Gln Ile Gly Ala Leu Ala Gly Val Ser
    210                 215                 220
Arg Val Thr Ile Trp Ser Asp Val Ala Gly Val Tyr Ser Ala Asp Pro
225                 230                 235                 240
Arg Lys Val Lys Asp Ala Cys Leu Leu Pro Leu Leu Arg Leu Asp Glu
                245                 250                 255
Ala Ser Glu Leu Ala Arg Leu Ala Ala Pro Val Leu His Ala Arg Thr
            260                 265                 270
Leu Gln Pro Val Ser Gly Ser Glu Ile Asp Leu Gln Leu Arg Cys Ser
        275                 280                 285
Tyr Thr Pro Asp Gln Gly Ser Thr Arg Ile Glu Arg Val Leu Ala Ser
    290                 295                 300
Gly Thr Gly Ala Arg Ile Val Thr Ser His Asp Asp Val Cys Leu Ile
305                 310                 315                 320
Glu Phe Gln Val Pro Ala Ser Gln Asp Phe Lys Leu Ala His Lys Glu
                325                 330                 335
Ile Asp Gln Ile Leu Lys Arg Ala Gln Val Arg Pro Leu Ala Val Gly
            340                 345                 350
Val His Asn Asp Arg Gln Leu Leu Gln Phe Cys Tyr Thr Ser Glu Val
        355                 360                 365
Ala Asp Ser Ala Leu Lys Ile Leu Asp Glu Ala Gly Leu Pro Gly Glu
    370                 375                 380
Leu Arg Leu Arg Gln Gly Leu Ala Leu Val Ala Met Val Gly Ala Gly
385                 390                 395                 400
Val Thr Arg Asn Pro Leu His Cys His Arg Phe Trp Gln Gln Leu Lys
                405                 410                 415
Gly Gln Pro Val Glu Phe Thr Trp Gln Ser Asp Gly Ile Ser Leu
            420                 425                 430
Val Ala Val Leu Arg Thr Gly Pro Thr Glu Ser Leu Ile Gln Gly Leu
        435                 440                 445
His Gln Ser Val Phe Arg Ala Glu Lys Arg Ile Gly Leu Val Leu Phe
    450                 455                 460
Gly Lys Gly Asn Ile Gly Ser Arg Trp Leu Glu Leu Phe Ala Arg Glu
465                 470                 475                 480
Gln Ser Thr Leu Ser Ala Arg Thr Gly Phe Glu Phe Val Leu Ala Gly
                485                 490                 495
Val Val Asp Ser Arg Arg Ser Leu Leu Ser Tyr Asp Gly Leu Asp Ala
            500                 505                 510
Ser Arg Ala Leu Ala Phe Phe Asn Asp Glu Ala Val Glu Gln Asp Glu
        515                 520                 525
Glu Ser Leu Phe Leu Trp Met Arg Ala His Pro Tyr Asp Asp Leu Val
    530                 535                 540
Val Leu Asp Val Thr Ala Ser Gln Gln Leu Ala Asp Gln Tyr Leu Asp
545                 550                 555                 560
Phe Ala Ser His Gly Phe His Val Ile Ser Ala Asn Lys Leu Ala Gly
                565                 570                 575
Ala Ser Asp Ser Asn Lys Tyr Arg Gln Ile His Asp Ala Phe Glu Lys
            580                 585                 590
Thr Gly Arg His Trp Leu Tyr Asn Ala Thr Val Gly Ala Gly Leu Pro
```

```
                595                 600                 605
Ile Asn His Thr Val Arg Asp Leu Ile Asp Ser Gly Asp Thr Ile Leu
        610                 615                 620

Ser Ile Ser Gly Ile Phe Ser Gly Thr Leu Ser Trp Leu Phe Leu Gln
625                 630                 635                 640

Phe Asp Gly Ser Val Pro Phe Thr Glu Leu Val Asp Gln Ala Trp Gln
                645                 650                 655

Gln Gly Leu Thr Glu Pro Asp Pro Arg Asp Asp Leu Ser Gly Lys Asp
            660                 665                 670

Val Met Arg Lys Leu Val Ile Leu Ala Arg Glu Ala Gly Tyr Asn Ile
        675                 680                 685

Glu Pro Asp Gln Val Arg Val Glu Ser Leu Val Pro Ala His Cys Glu
        690                 695                 700

Gly Gly Ser Ile Asp His Phe Phe Glu Asn Gly Asp Glu Leu Asn Glu
705                 710                 715                 720

Gln Met Val Gln Arg Leu Glu Ala Ala Arg Glu Met Gly Leu Val Leu
                725                 730                 735

Arg Tyr Val Ala Arg Phe Asp Ala Asn Gly Lys Ala Arg Val Gly Val
            740                 745                 750

Glu Ala Val Arg Glu Asp His Pro Leu Ala Ser Leu Leu Pro Cys Asp
        755                 760                 765

Asn Val Phe Ala Ile Glu Ser Arg Trp Tyr Arg Asp Asn Pro Leu Val
770                 775                 780

Ile Arg Gly Pro Gly Ala Gly Arg Asp Val Thr Ala Gly Ala Ile Gln
785                 790                 795                 800

Ser Asp Ile Asn Arg Leu Ala Gln Leu Leu
                805                 810

<210> SEQ ID NO 89
<211> LENGTH: 473
<212> TYPE: PRT
<213> ORGANISM: Methanococcus jannaschii

<400> SEQUENCE: 89

Met Thr Thr Val Met Lys Phe Gly Gly Thr Ser Val Gly Ser Gly Glu
1               5                   10                  15

Arg Ile Arg His Val Ala Lys Ile Val Thr Lys Arg Lys Lys Glu Asp
                20                  25                  30

Asp Val Val Val Val Val Ser Ala Met Ser Glu Val Thr Asn Ala
            35                  40                  45

Leu Val Glu Ile Ser Gln Gln Ala Leu Asp Val Arg Asp Ile Ala Lys
50                  55                  60

Val Gly Asp Phe Ile Lys Phe Ile Arg Glu Lys His Tyr Lys Ala Ile
65                  70                  75                  80

Glu Glu Ala Ile Lys Ser Glu Glu Ile Lys Glu Val Lys Lys Ile
                85                  90                  95

Ile Asp Ser Arg Ile Glu Glu Leu Glu Lys Val Leu Ile Gly Val Ala
                100                 105                 110

Tyr Leu Gly Glu Leu Thr Pro Lys Ser Arg Asp Tyr Ile Leu Ser Phe
            115                 120                 125

Gly Glu Arg Leu Ser Ser Pro Ile Leu Ser Gly Ala Ile Arg Asp Leu
        130                 135                 140

Gly Glu Lys Ser Ile Ala Leu Glu Gly Gly Glu Ala Gly Ile Ile Thr
145                 150                 155                 160
```

-continued

Asp Asn Asn Phe Gly Ser Ala Arg Val Lys Arg Leu Glu Val Lys Glu
            165                 170                 175

Arg Leu Leu Pro Leu Leu Lys Glu Gly Ile Ile Pro Val Thr Gly
        180                 185                 190

Phe Ile Gly Thr Thr Glu Glu Gly Tyr Ile Thr Thr Leu Gly Arg Gly
            195                 200                 205

Gly Ser Asp Tyr Ser Ala Ala Leu Ile Gly Tyr Gly Leu Asp Ala Asp
        210                 215                 220

Ile Ile Glu Ile Trp Thr Asp Val Ser Gly Val Tyr Thr Thr Asp Pro
225                 230                 235                 240

Arg Leu Val Pro Thr Ala Arg Arg Ile Pro Lys Leu Ser Tyr Ile Glu
            245                 250                 255

Ala Met Glu Leu Ala Tyr Phe Gly Ala Lys Val Leu His Pro Arg Thr
            260                 265                 270

Ile Glu Pro Ala Met Glu Lys Gly Ile Pro Ile Leu Val Lys Asn Thr
        275                 280                 285

Phe Glu Pro Glu Ser Glu Gly Thr Leu Ile Thr Asn Asp Met Glu Met
    290                 295                 300

Ser Asp Ser Ile Val Lys Ala Ile Ser Thr Ile Lys Asn Val Ala Leu
305                 310                 315                 320

Ile Asn Ile Phe Gly Ala Gly Met Val Gly Val Ser Gly Thr Ala Ala
            325                 330                 335

Arg Ile Phe Lys Ala Leu Gly Glu Glu Val Asn Val Ile Leu Ile
            340                 345                 350

Ser Gln Gly Ser Ser Glu Thr Asn Ile Ser Leu Val Val Ser Glu Glu
    355                 360                 365

Asp Val Asp Lys Ala Leu Lys Ala Leu Lys Arg Glu Phe Gly Asp Phe
370                 375                 380

Gly Lys Lys Ser Phe Leu Asn Asn Asn Leu Ile Arg Asp Val Ser Val
385                 390                 395                 400

Asp Lys Asp Val Cys Val Ile Ser Val Val Gly Ala Gly Met Arg Gly
            405                 410                 415

Ala Lys Gly Ile Ala Gly Lys Ile Phe Thr Ala Val Ser Glu Ser Gly
            420                 425                 430

Ala Asn Ile Lys Met Ile Ala Gln Gly Ser Ser Glu Val Asn Ile Ser
            435                 440                 445

Phe Val Ile Asp Glu Lys Asp Leu Leu Asn Cys Val Arg Lys Leu His
        450                 455                 460

Glu Lys Phe Ile Glu Lys Thr Asn Ser
465                 470

<210> SEQ ID NO 90
<211> LENGTH: 405
<212> TYPE: PRT
<213> ORGANISM: Thermus thermophilus

<400> SEQUENCE: 90

Met Ala Leu Val Val Gln Lys Tyr Gly Gly Thr Ser Val Gly Asp Leu
1               5                   10                  15

Glu Arg Ile His Lys Val Ala Gln Arg Ile Ala His Tyr Arg Glu Lys
                20                  25                  30

Gly His Arg Leu Ala Val Val Val Ser Ala Met Gly His Thr Thr Asp
            35                  40                  45

Glu Leu Ile Ala Leu Ala Lys Arg Val Asn Pro Arg Pro Pro Phe Arg
        50                  55                  60

```
Glu Leu Asp Leu Leu Thr Thr Thr Gly Glu Gln Val Ser Val Ala Leu
 65                  70                  75                  80

Leu Ser Met Gln Leu Trp Ala Met Gly Ile Pro Ala Lys Gly Phe Val
             85                  90                  95

Gln His Gln Ile Gly Ile Thr Thr Asp Gly Arg Tyr Gly Asp Ala Arg
            100                 105                 110

Ile Leu Glu Val Asn Pro Ala Arg Ile Arg Glu Ala Leu Asp Gln Gly
        115                 120                 125

Phe Val Ala Val Ile Ala Gly Phe Met Gly Thr Thr Pro Glu Gly Glu
130                 135                 140

Ile Thr Thr Leu Gly Arg Gly Gly Ser Asp Thr Thr Ala Val Ala Ile
145                 150                 155                 160

Ala Ala Ala Leu Gly Ala Lys Glu Cys Glu Ile Tyr Thr Asp Thr Glu
                165                 170                 175

Gly Val Tyr Thr Thr Asp Pro His Leu Ile Pro Glu Ala Arg Lys Leu
            180                 185                 190

Ser Val Ile Gly Tyr Asp Gln Met Leu Glu Met Ala Ala Leu Gly Ala
        195                 200                 205

Arg Val Leu His Pro Arg Ala Val Tyr Tyr Ala Lys Arg Tyr Gly Val
210                 215                 220

Val Leu His Val Arg Ser Ser Phe Ser Tyr Asn Pro Gly Thr Leu Val
225                 230                 235                 240

Lys Glu Val Ala Met Glu Met Asp Lys Ala Val Thr Gly Val Ala Leu
                245                 250                 255

Asp Leu Asp His Ala Gln Ile Gly Leu Ile Gly Ile Pro Asp Gln Pro
            260                 265                 270

Gly Ile Ala Ala Lys Val Phe Gln Ala Leu Ala Glu Arg Gly Ile Ala
        275                 280                 285

Val Asp Met Ile Ile Gln Gly Val Pro Gly His Asp Pro Ser Arg Gln
290                 295                 300

Gln Met Ala Phe Thr Val Lys Lys Asp Phe Ala Gln Glu Ala Leu Glu
305                 310                 315                 320

Ala Leu Glu Pro Val Leu Ala Glu Ile Gly Gly Glu Ala Ile Leu Arg
                325                 330                 335

Pro Asp Ile Ala Lys Val Ser Ile Val Gly Val Gly Leu Ala Ser Thr
            340                 345                 350

Pro Glu Val Pro Ala Lys Met Phe Gln Ala Val Ala Ser Thr Gly Ala
        355                 360                 365

Asn Ile Glu Met Ile Ala Thr Ser Glu Val Arg Ile Ser Val Ile Ile
370                 375                 380

Pro Ala Glu Tyr Ala Glu Ala Leu Arg Ala Val His Gln Ala Phe
385                 390                 395                 400

Glu Leu Asp Lys Ala
            405

<210> SEQ ID NO 91
<211> LENGTH: 420
<212> TYPE: PRT
<213> ORGANISM: Corynebacterium glutamicum

<400> SEQUENCE: 91

Met Ala Leu Val Val Gln Lys Tyr Gly Gly Ser Ser Leu Glu Ser Ala
1               5                  10                   15

Glu Arg Ile Arg Asn Val Ala Glu Arg Ile Val Ala Thr Lys Lys Ala
```

Gly Asn Asp Val Val Val Cys Ser Ala Met Gly Asp Thr Thr Asp
         20                  25                  30
    35                  40                  45

Glu Leu Leu Glu Leu Ala Ala Ala Val Asn Pro Val Pro Pro Ala Arg
 50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
            210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
            290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly
            420

<210> SEQ ID NO 92

-continued

```
<211> LENGTH: 569
<212> TYPE: PRT
<213> ORGANISM: Arabidopsis thaliana

<400> SEQUENCE: 92

Met Ala Ala Thr Arg Val Arg Cys Cys His Ser Asn Ala Ala Phe Thr
1               5                   10                  15

Arg Leu Pro Leu Thr Arg His Arg Asn Ser Pro Thr Leu Pro Ile Ser
            20                  25                  30

Leu Asn Arg Val Asp Phe Pro Thr Leu Lys Lys Leu Ser Leu Pro Ile
        35                  40                  45

Gly Asp Gly Ser Ser Ile Arg Lys Val Ser Gly Ser Gly Ser Arg Asn
50                  55                  60

Ile Val Arg Ala Val Leu Glu Glu Lys Lys Thr Glu Ala Ile Thr Glu
65                  70                  75                  80

Val Asp Glu Lys Gly Ile Thr Cys Val Met Lys Phe Gly Gly Ser Ser
            85                  90                  95

Val Ala Ser Ala Glu Arg Met Lys Glu Val Ala Asp Leu Ile Leu Thr
        100                 105                 110

Phe Pro Glu Glu Ser Pro Val Ile Val Leu Ser Ala Met Gly Lys Thr
    115                 120                 125

Thr Asn Asn Leu Leu Leu Ala Gly Glu Lys Ala Val Ser Cys Gly Val
130                 135                 140

Ser Asn Ala Ser Glu Ile Glu Glu Leu Ser Ile Ile Lys Glu Leu His
145                 150                 155                 160

Ile Arg Thr Val Lys Glu Leu Asn Ile Asp Pro Ser Val Ile Leu Thr
            165                 170                 175

Tyr Leu Glu Glu Leu Glu Gln Leu Leu Lys Gly Ile Ala Met Met Lys
        180                 185                 190

Glu Leu Thr Leu Arg Thr Arg Asp Tyr Leu Val Ser Phe Gly Glu Cys
    195                 200                 205

Leu Ser Thr Arg Ile Phe Ala Ala Tyr Leu Asn Thr Ile Gly Val Lys
    210                 215                 220

Ala Arg Gln Tyr Asp Ala Phe Glu Ile Gly Phe Ile Thr Thr Asp Asp
225                 230                 235                 240

Phe Thr Asn Gly Asp Ile Leu Glu Ala Thr Tyr Pro Ala Val Ala Lys
            245                 250                 255

Arg Leu Tyr Asp Asp Trp Met His Asp Pro Ala Val Pro Ile Val Thr
        260                 265                 270

Gly Phe Leu Gly Lys Gly Trp Lys Thr Gly Ala Val Thr Thr Leu Gly
    275                 280                 285

Arg Gly Gly Ser Asp Leu Thr Ala Thr Ile Gly Lys Ala Leu Gly
    290                 295                 300

Leu Lys Glu Ile Gln Val Trp Lys Asp Val Asp Gly Val Leu Thr Cys
305                 310                 315                 320

Asp Pro Thr Ile Tyr Lys Arg Ala Thr Pro Val Pro Tyr Leu Thr Phe
            325                 330                 335

Asp Glu Ala Ala Glu Leu Ala Tyr Phe Gly Ala Gln Val Leu His Pro
        340                 345                 350

Gln Ser Met Arg Pro Ala Arg Glu Gly Glu Ile Pro Val Arg Val Lys
    355                 360                 365

Asn Ser Tyr Asn Pro Lys Ala Pro Gly Thr Ile Ile Thr Lys Thr Arg
    370                 375                 380

Asp Met Thr Lys Ser Ile Leu Thr Ser Ile Val Leu Lys Arg Asn Val
```

```
                385                 390                 395                 400
        Thr Met Leu Asp Ile Ala Ser Thr Arg Met Leu Gly Gln Val Gly Phe
                        405                 410                 415

Leu Ala Lys Val Phe Ser Ile Phe Glu Glu Leu Gly Ile Ser Val Asp
                        420                 425                 430

Val Val Ala Thr Ser Glu Val Ser Ile Ser Leu Thr Leu Asp Pro Ser
                        435                 440                 445

Lys Leu Trp Ser Arg Glu Leu Ile Gln Gln Glu Leu Asp His Val Val
                        450                 455                 460

Glu Glu Leu Glu Lys Ile Ala Val Val Asn Leu Leu Lys Gly Arg Ala
        465                 470                 475                 480

Ile Ile Ser Leu Ile Gly Asn Val Gln His Ser Ser Leu Ile Leu Glu
                        485                 490                 495

Arg Ala Phe His Val Leu Tyr Thr Lys Gly Val Asn Val Gln Met Ile
                        500                 505                 510

Ser Gln Gly Ala Ser Lys Val Asn Ile Ser Phe Ile Val Asn Glu Ala
                        515                 520                 525

Glu Ala Glu Gly Cys Val Gln Ala Leu His Lys Ser Phe Phe Glu Ser
                        530                 535                 540

Gly Asp Leu Ser Glu Leu Leu Ile Gln Pro Arg Leu Gly Asn Gly Ser
        545                 550                 555                 560

Pro Val Arg Thr Leu Gln Val Glu Asn
                        565

<210> SEQ ID NO 93
<211> LENGTH: 527
<212> TYPE: PRT
<213> ORGANISM: Saccharomyces cerevisiae

<400> SEQUENCE: 93

Met Pro Met Asp Phe Gln Pro Thr Ser His Ser Asn Trp Val Val
        1               5                   10                  15

Gln Lys Phe Gly Gly Thr Ser Val Gly Lys Phe Pro Val Gln Ile Val
                        20                  25                  30

Asp Asp Ile Val Lys His Tyr Ser Lys Pro Asp Gly Pro Asn Asn Asn
                        35                  40                  45

Val Ala Val Val Cys Ser Ala Arg Ser Ser Tyr Thr Lys Ala Glu Gly
                50                  55                  60

Thr Thr Ser Arg Leu Leu Lys Cys Cys Asp Leu Ala Ser Gln Glu Ser
        65                  70                  75                  80

Glu Phe Gln Asp Ile Ile Glu Val Ile Arg Gln Asp His Ile Asp Asn
                        85                  90                  95

Ala Asp Arg Phe Ile Leu Asn Pro Ala Leu Gln Ala Lys Leu Val Asp
                        100                 105                 110

Asp Thr Asn Lys Glu Leu Glu Leu Val Lys Lys Tyr Leu Asn Ala Ser
                        115                 120                 125

Lys Val Leu Gly Glu Val Ser Ser Arg Thr Val Asp Leu Val Met Ser
                        130                 135                 140

Cys Gly Glu Lys Leu Ser Cys Leu Phe Met Thr Ala Leu Cys Asn Asp
        145                 150                 155                 160

Arg Gly Cys Lys Ala Lys Tyr Val Asp Leu Ser His Ile Val Pro Ser
                        165                 170                 175

Asp Phe Ser Ala Ser Ala Leu Asp Asn Ser Phe Tyr Thr Phe Leu Val
                        180                 185                 190
```

Gln Ala Leu Lys Glu Lys Leu Ala Pro Phe Val Ser Ala Lys Glu Arg
    195                 200                 205

Ile Val Pro Val Phe Thr Gly Phe Phe Gly Leu Val Pro Thr Gly Leu
    210                 215                 220

Leu Asn Gly Val Gly Arg Gly Tyr Thr Asp Leu Cys Ala Ala Leu Ile
225                 230                 235                 240

Ala Val Ala Val Asn Ala Asp Glu Leu Gln Val Trp Lys Glu Val Asp
                245                 250                 255

Gly Ile Phe Thr Ala Asp Pro Arg Lys Val Pro Glu Ala Arg Leu Leu
                260                 265                 270

Asp Ser Val Thr Pro Glu Glu Ala Ser Glu Leu Thr Tyr Tyr Gly Ser
            275                 280                 285

Glu Val Ile His Pro Phe Thr Met Glu Gln Val Ile Arg Ala Lys Ile
        290                 295                 300

Pro Ile Arg Ile Lys Asn Val Gln Asn Pro Leu Gly Asn Gly Thr Ile
305                 310                 315                 320

Ile Tyr Pro Asp Asn Val Ala Lys Lys Gly Glu Ser Thr Pro Pro His
                325                 330                 335

Pro Pro Glu Asn Leu Ser Ser Ser Phe Tyr Glu Lys Arg Lys Arg Gly
            340                 345                 350

Ala Thr Ala Ile Thr Thr Lys Asn Asp Ile Phe Val Ile Asn Ile His
        355                 360                 365

Ser Asn Lys Lys Thr Leu Ser His Gly Phe Leu Ala Gln Ile Phe Thr
    370                 375                 380

Ile Leu Asp Lys Tyr Lys Leu Val Val Asp Leu Ile Ser Thr Ser Glu
385                 390                 395                 400

Val His Val Ser Met Ala Leu Pro Ile Pro Asp Ala Asp Ser Leu Lys
                405                 410                 415

Ser Leu Arg Gln Ala Glu Glu Lys Leu Arg Ile Leu Gly Ser Val Asp
            420                 425                 430

Ile Thr Lys Lys Leu Ser Ile Val Ser Leu Val Gly Lys His Met Lys
        435                 440                 445

Gln Tyr Ile Gly Ile Ala Gly Thr Met Phe Thr Thr Leu Ala Glu Glu
    450                 455                 460

Gly Ile Asn Ile Glu Met Ile Ser Gln Gly Ala Asn Glu Ile Asn Ile
465                 470                 475                 480

Ser Cys Val Ile Asn Glu Ser Asp Ser Ile Lys Ala Leu Gln Cys Ile
                485                 490                 495

His Ala Lys Leu Leu Ser Glu Arg Thr Asn Thr Ser Asn Gln Phe Glu
            500                 505                 510

His Ala Ile Asp Glu Arg Leu Glu Gln Leu Lys Arg Leu Gly Ile
        515                 520                 525

<210> SEQ ID NO 94
<211> LENGTH: 354
<212> TYPE: PRT
<213> ORGANISM: Methanococcus jannaschii

<400> SEQUENCE: 94

Met Ser Lys Gly Glu Lys Met Lys Ile Lys Val Gly Val Leu Gly Ala
1               5                   10                  15

Thr Gly Ser Val Gly Gln Arg Phe Val Gln Leu Leu Ala Asp His Pro
            20                  25                  30

Met Phe Glu Leu Thr Ala Leu Ala Ala Ser Glu Arg Ser Ala Gly Lys
        35                  40                  45

Lys Tyr Lys Asp Ala Cys Tyr Trp Phe Gln Asp Arg Asp Ile Pro Glu
            50                  55                  60

Asn Ile Lys Asp Met Val Val Ile Pro Thr Asp Pro Lys His Glu Glu
 65                  70                  75                  80

Phe Glu Asp Val Asp Ile Val Phe Ser Ala Leu Pro Ser Asp Leu Ala
                    85                  90                  95

Lys Lys Phe Glu Pro Glu Phe Ala Lys Glu Gly Lys Leu Ile Phe Ser
            100                 105                 110

Asn Ala Ser Ala Tyr Arg Met Glu Glu Asp Val Pro Leu Val Ile Pro
            115                 120                 125

Glu Val Asn Ala Asp His Leu Glu Leu Ile Glu Ile Gln Arg Glu Lys
            130                 135                 140

Arg Gly Trp Asp Gly Ala Ile Ile Thr Asn Pro Asn Cys Ser Thr Ile
145                 150                 155                 160

Cys Ala Val Ile Thr Leu Lys Pro Ile Met Asp Lys Phe Gly Leu Glu
                165                 170                 175

Ala Val Phe Ile Ala Thr Met Gln Ala Val Ser Gly Ala Gly Tyr Asn
                180                 185                 190

Gly Val Pro Ser Met Ala Ile Leu Asp Asn Leu Ile Pro Phe Ile Lys
                195                 200                 205

Asn Glu Glu Lys Met Gln Thr Glu Ser Leu Lys Leu Leu Gly Thr
210                 215                 220

Leu Lys Asp Gly Lys Val Glu Leu Ala Asn Phe Lys Ile Ser Ala Ser
225                 230                 235                 240

Cys Asn Arg Val Ala Val Ile Asp Gly His Thr Glu Ser Ile Phe Val
                245                 250                 255

Lys Thr Lys Glu Gly Ala Glu Pro Glu Glu Ile Lys Glu Val Met Asp
                260                 265                 270

Lys Phe Asp Pro Leu Lys Asp Leu Asn Leu Pro Thr Tyr Ala Lys Pro
            275                 280                 285

Ile Val Ile Arg Glu Glu Ile Asp Arg Pro Gln Pro Arg Leu Asp Arg
            290                 295                 300

Asn Glu Gly Asn Gly Met Ser Ile Val Val Gly Arg Ile Arg Lys Asp
305                 310                 315                 320

Pro Ile Phe Asp Val Lys Tyr Thr Ala Leu Glu His Asn Thr Ile Arg
                325                 330                 335

Gly Ala Ala Gly Ala Ser Val Leu Asn Ala Glu Tyr Phe Val Lys Lys
            340                 345                 350

Tyr Ile

<210> SEQ ID NO 95
<211> LENGTH: 331
<212> TYPE: PRT
<213> ORGANISM: Thermus thermophilus

<400> SEQUENCE: 95

Met Arg Val Ala Val Val Gly Ala Thr Gly Ala Val Gly Arg Glu Ile
 1               5                  10                  15

Leu Lys Val Leu Glu Ala Arg Asp Phe Pro Leu Ser Asp Leu Arg Leu
                20                  25                  30

Tyr Ala Ser Pro Arg Ser Ala Gly Val Arg Leu Ala Phe Arg Gly Glu
            35                  40                  45

Glu Ile Pro Val Glu Pro Leu Pro Glu Gly Pro Leu Pro Val Asp Leu
 50                  55                  60

Val Leu Ala Ser Ala Gly Gly Ile Ser Lys Ala Lys Ala Leu Val
65                  70                  75                  80

Trp Ala Glu Gly Gly Ala Leu Val Val Asp Asn Ser Ser Ala Trp Arg
            85                  90                  95

Tyr Glu Pro Trp Val Pro Leu Val Val Pro Glu Val Asn Arg Glu Lys
                100                 105                 110

Ile Phe Gln His Arg Gly Ile Ile Ala Asn Pro Asn Cys Thr Thr Ala
            115                 120                 125

Ile Leu Ala Met Ala Leu Trp Pro Leu His Arg Ala Phe Gln Ala Lys
130                 135                 140

Arg Val Ile Val Ala Thr Tyr Gln Ala Ala Ser Gly Ala Gly Ala Lys
145                 150                 155                 160

Ala Met Glu Glu Leu Leu Thr Glu Thr His Arg Phe Leu His Gly Glu
                165                 170                 175

Ala Pro Lys Ala Glu Ala Phe Ala His Pro Leu Pro Phe Asn Val Ile
            180                 185                 190

Pro His Ile Asp Ala Phe Gln Glu Asn Gly Tyr Thr Arg Glu Glu Met
        195                 200                 205

Lys Val Val Trp Glu Thr His Lys Ile Phe Gly Asp Asp Thr Ile Arg
210                 215                 220

Ile Ser Ala Thr Ala Val Arg Val Pro Thr Leu Arg Ala His Ala Glu
225                 230                 235                 240

Ala Val Ser Val Glu Phe Ala Arg Pro Val Thr Pro Glu Ala Ala Arg
                245                 250                 255

Glu Val Leu Lys Glu Ala Pro Gly Val Glu Val Val Asp Glu Pro Glu
            260                 265                 270

Ala Lys Arg Tyr Pro Met Pro Leu Thr Ala Ser Gly Lys Trp Asp Val
        275                 280                 285

Glu Val Gly Arg Ile Arg Lys Ser Leu Ala Phe Glu Asn Gly Leu Asp
    290                 295                 300

Phe Phe Val Val Gly Asp Gln Leu Leu Lys Gly Ala Ala Leu Asn Ala
305                 310                 315                 320

Val Gln Ile Ala Glu Glu Trp Leu Lys Gly Ala
                325                 330

<210> SEQ ID NO 96
<211> LENGTH: 346
<212> TYPE: PRT
<213> ORGANISM: Bacillus subtilis

<400> SEQUENCE: 96

Met Gly Arg Gly Leu His Val Ala Val Val Gly Ala Thr Gly Ala Val
1               5                   10                  15

Gly Gln Gln Met Leu Lys Thr Leu Glu Asp Arg Asn Phe Glu Met Asp
                20                  25                  30

Thr Leu Thr Leu Leu Ser Ser Lys Arg Ser Ala Gly Thr Lys Val Thr
            35                  40                  45

Phe Lys Gly Gln Glu Leu Thr Val Gln Glu Ala Ser Pro Glu Ser Phe
        50                  55                  60

Glu Gly Val Asn Ile Ala Leu Phe Ser Ala Gly Ser Val Ser Gln
65                  70                  75                  80

Ala Leu Ala Pro Glu Ala Val Lys Arg Gly Ala Ile Val Ile Asp Asn
                85                  90                  95

Thr Ser Ala Phe Arg Met Asp Glu Asn Thr Pro Leu Val Val Pro Glu

```
            100                 105                 110
Val Asn Glu Ala Asp Leu His Glu His Asn Gly Ile Ile Ala Asn Pro
            115                 120                 125

Asn Cys Ser Thr Ile Gln Met Val Ala Ala Leu Pro Ile Arg Lys
130                 135                 140

Ala Tyr Gly Leu Asn Lys Val Ile Val Ser Thr Tyr Gln Ala Val Ser
145                 150                 155                 160

Gly Ala Gly Asn Glu Ala Val Lys Glu Leu Tyr Ser Gln Thr Gln Ala
                165                 170                 175

Ile Leu Asn Lys Glu Glu Ile Glu Pro Glu Ile Met Pro Val Lys Gly
                180                 185                 190

Asp Lys Lys His Tyr Gln Ile Ala Phe Asn Ala Ile Pro Gln Ile Asp
                195                 200                 205

Lys Phe Gln Asp Asn Gly Tyr Thr Phe Glu Glu Met Lys Met Ile Asn
            210                 215                 220

Glu Thr Lys Lys Ile Met His Met Pro Asp Leu Gln Val Ala Ala Thr
225                 230                 235                 240

Cys Val Arg Leu Pro Ile Gln Thr Gly His Ser Glu Ser Val Tyr Ile
                245                 250                 255

Glu Ile Asp Arg Asp Asp Ala Thr Val Glu Asp Ile Lys Asn Leu Leu
                260                 265                 270

Lys Glu Ala Pro Gly Val Thr Leu Gln Asp Asp Pro Ser Gln Gln Leu
                275                 280                 285

Tyr Pro Met Pro Ala Asp Ala Val Gly Lys Asn Asp Val Phe Val Gly
            290                 295                 300

Arg Ile Arg Lys Asp Leu Asp Arg Ala Asn Gly Phe His Leu Trp Val
305                 310                 315                 320

Val Ser Asp Asn Leu Leu Lys Gly Ala Ala Trp Asn Ser Val Gln Ile
                325                 330                 335

Ala Glu Ser Leu Lys Lys Leu Asn Leu Val
                340                 345

<210> SEQ ID NO 97
<211> LENGTH: 344
<212> TYPE: PRT
<213> ORGANISM: Corynebacterium glutamicum

<400> SEQUENCE: 97

Met Thr Thr Ile Ala Val Val Gly Ala Thr Gly Gln Val Gly Gln Val
1               5                   10                  15

Met Arg Thr Leu Leu Glu Glu Arg Asn Phe Pro Ala Asp Thr Val Arg
                20                  25                  30

Phe Phe Ala Ser Pro Arg Ser Ala Gly Arg Lys Ile Glu Phe Arg Gly
            35                  40                  45

Thr Glu Ile Glu Val Glu Asp Ile Thr Gln Ala Thr Glu Glu Ser Leu
        50                  55                  60

Lys Asp Ile Asp Val Ala Leu Phe Ser Ala Gly Gly Thr Ala Ser Lys
65                  70                  75                  80

Gln Tyr Ala Pro Leu Phe Ala Ala Ala Gly Ala Thr Val Val Asp Asn
                85                  90                  95

Ser Ser Ala Trp Arg Lys Asp Asp Glu Val Pro Leu Ile Val Ser Glu
                100                 105                 110

Val Asn Pro Ser Asp Lys Asp Ser Leu Val Lys Gly Ile Ile Ala Asn
            115                 120                 125
```

```
Pro Asn Cys Thr Thr Met Ala Ala Met Pro Val Leu Lys Pro Leu His
    130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
            180                 185                 190

Asp Ala Gly Asp Val Gly Pro Tyr Val Ser Pro Ile Ala Tyr Asn Val
        195                 200                 205

Leu Pro Phe Ala Gly Asn Leu Val Asp Asp Gly Thr Phe Glu Thr Asp
210                 215                 220

Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Glu Phe Asp Lys Ala Ile Thr Val Asp
            260                 265                 270

Gln Ala Gln Glu Ile Leu Gly Ala Ala Ser Gly Val Lys Leu Val Asp
        275                 280                 285

Val Pro Thr Pro Leu Ala Ala Ala Gly Ile Asp Glu Ser Leu Val Gly
290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
            340

<210> SEQ ID NO 98
<211> LENGTH: 340
<212> TYPE: PRT
<213> ORGANISM: Arabidopsis thaliana

<400> SEQUENCE: 98

Glu Ser Ala Pro Ser Leu Ala Val Val Gly Val Thr Gly Ala Val Gly
1               5                   10                  15

Gln Glu Phe Leu Ser Val Leu Ser Asp Arg Asp Phe Pro Tyr Ser Ser
            20                  25                  30

Ile Lys Met Leu Ala Ser Lys Arg Ser Ala Gly Lys Arg Val Ala Phe
        35                  40                  45

Asp Gly His Glu Tyr Thr Val Glu Glu Leu Thr Ala Asp Ser Phe Asn
    50                  55                  60

Gly Val Asp Ile Ala Leu Phe Ser Ala Gly Ser Ile Ser Lys Glu
65                  70                  75                  80

Phe Gly Pro Leu Ala Ala Glu Lys Gly Thr Ile Val Val Asp Asn Ser
                85                  90                  95

Ser Ala Phe Arg Met Val Asp Gly Val Pro Leu Val Ile Pro Glu Val
            100                 105                 110

Asn Pro Glu Ala Met Lys Gly Ile Lys Val Gly Met Gly Lys Gly Ala
        115                 120                 125

Leu Ile Ala Asn Pro Asn Cys Ser Thr Ile Ile Cys Leu Met Ala Val
    130                 135                 140

Thr Pro Leu His His His Ala Lys Val Lys Arg Met Val Val Ser Thr
145                 150                 155                 160
```

```
Tyr Gln Ala Ala Ser Gly Ala Gly Ala Ala Met Glu Glu Leu Val
                165                 170                 175

Gln Gln Thr Arg Glu Val Leu Glu Gly Lys Pro Pro Thr Cys Asn Ile
            180                 185                 190

Phe Gly Gln Gln Tyr Ala Phe Asn Leu Phe Ser His Asn Ala Pro Ile
        195                 200                 205

Leu Asp Asn Gly Tyr Asn Glu Glu Met Lys Leu Val Lys Glu Thr
    210                 215                 220

Arg Lys Ile Trp Asn Asp Thr Glu Val Lys Val Thr Ala Thr Cys Ile
225                 230                 235                 240

Arg Val Pro Val Met Arg Ala His Ala Glu Ser Val Asn Leu Gln Phe
                245                 250                 255

Glu Asn Pro Leu Asp Glu Asn Thr Ala Arg Glu Ile Leu Lys Lys Ala
            260                 265                 270

Pro Gly Val Tyr Ile Ile Asp Asp Arg Ala Ser Asn Thr Phe Pro Thr
        275                 280                 285

Pro Leu Asp Val Ser Asn Lys Asp Val Ala Val Gly Arg Ile Arg
    290                 295                 300

Arg Asp Val Ser Gln Asp Gly Asn Phe Gly Leu Asp Ile Phe Val Cys
305                 310                 315                 320

Gly Asp Gln Ile Arg Lys Gly Ala Ala Leu Asn Ala Val Gln Ile Ala
                325                 330                 335

Glu Met Leu Leu
            340

<210> SEQ ID NO 99
<211> LENGTH: 365
<212> TYPE: PRT
<213> ORGANISM: Saccharomyces cerevisiae

<400> SEQUENCE: 99

Met Ala Gly Lys Lys Ile Ala Gly Val Leu Gly Ala Thr Gly Ser Val
1               5                   10                  15

Gly Gln Arg Phe Ile Leu Leu Leu Ala Asn His Pro His Phe Glu Leu
            20                  25                  30

Lys Val Leu Gly Ala Ser Ser Arg Ser Ala Gly Lys Lys Tyr Val Asp
        35                  40                  45

Ala Val Asn Trp Lys Gln Thr Asp Leu Leu Pro Glu Ser Ala Thr Asp
    50                  55                  60

Ile Ile Val Ser Glu Cys Lys Ser Glu Phe Lys Glu Cys Asp Ile
65                  70                  75                  80

Val Phe Ser Gly Leu Asp Ala Asp Tyr Ala Gly Ala Ile Glu Lys Glu
                85                  90                  95

Phe Met Glu Ala Gly Ile Ala Ile Val Ser Asn Ala Lys Asn Tyr Arg
            100                 105                 110

Arg Glu Gln Asp Val Pro Leu Ile Val Pro Val Asn Pro Glu His
        115                 120                 125

Leu Asp Ile Val Ala Gln Lys Leu Asp Thr Ala Lys Ala Gln Gly Lys
    130                 135                 140

Pro Arg Pro Gly Phe Ile Ile Cys Ile Ser Asn Cys Ser Thr Ala Gly
145                 150                 155                 160

Leu Val Ala Pro Leu Lys Pro Leu Ile Glu Lys Phe Gly Pro Ile Asp
                165                 170                 175

Ala Leu Thr Thr Thr Thr Leu Gln Ala Ile Ser Gly Ala Gly Phe Ser
```

```
            180                 185                 190
Pro Gly Val Pro Gly Ile Asp Ile Leu Asp Asn Ile Ile Pro Tyr Ile
            195                 200                 205

Gly Gly Glu Glu Asp Lys Met Glu Trp Glu Thr Lys Lys Ile Leu Ala
        210                 215                 220

Pro Leu Ala Glu Asp Lys Thr His Val Lys Leu Leu Thr Pro Glu Glu
225                 230                 235                 240

Ile Lys Val Ser Ala Gln Cys Asn Arg Val Ala Val Ser Asp Gly His
                245                 250                 255

Thr Glu Cys Ile Ser Leu Arg Phe Lys Asn Arg Pro Ala Pro Ser Val
            260                 265                 270

Glu Gln Val Lys Thr Cys Leu Lys Glu Tyr Val Cys Asp Ala Tyr Lys
        275                 280                 285

Leu Gly Cys His Ser Ala Pro Lys Gln Thr Ile His Val Leu Glu Gln
    290                 295                 300

Pro Asp Arg Pro Gln Pro Arg Leu Asp Arg Asn Arg Asp Ser Gly Tyr
305                 310                 315                 320

Gly Val Ser Val Gly Arg Ile Arg Glu Asp Pro Leu Leu Asp Phe Lys
                325                 330                 335

Met Val Val Leu Ser His Asn Thr Ile Ile Gly Ala Ala Gly Ser Gly
            340                 345                 350

Val Leu Ile Ala Glu Ile Leu Leu Ala Arg Asn Leu Ile
        355                 360                 365

<210> SEQ ID NO 100
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 100
tataatcccg ggatgcgcgt taacaatggt ttgacc                                 36

<210> SEQ ID NO 101
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 101
tataattcta gattacagtt tcggaccagc cg                                     32

<210> SEQ ID NO 102
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 102
gaaggttgcg cctacactaa gcatagttgt tgatgagtgt aggctggagc tgcttc          56

<210> SEQ ID NO 103
<211> LENGTH: 56
<212> TYPE: DNA
<213> ORGANISM: Artificial Sequence
<220> FEATURE:
<223> OTHER INFORMATION: Synthetic Construct - Primer for amplification
```

<400> SEQUENCE: 103
ttaaaccagt tcgttcgggc aggtttcgcc tttttcatgg gaattagcca tggtcc        56

<210> SEQ ID NO 104
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 104
atggctgtta ctaatgtcgc tgaacttaac gcactcgtag agcgtgtgta ggctggagct        60
gcttc        65

<210> SEQ ID NO 105
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 105
ttaagcggat ttttcgctt ttttctcagc tttagccgga gcagccatat gaatatcctc        60
cttag        65

<210> SEQ ID NO 106
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 106
atgtcgagta agttagtact ggttctgaac tgcggtagtt cttcagtgta ggctggagct        60
gcttc        65

<210> SEQ ID NO 107
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 107
tcaggcagtc aggcggctcg cgtcttgcgc gataaccagt tcttccatat gaatatcctc        60
cttag        65

<210> SEQ ID NO 108
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 108
ttactccgta tttgcataaa aaccatgcga gttacgggcc tataagtgta ggctggagct        60
gcttc        65

<210> SEQ ID NO 109
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 109
atagattgag tgaaggtacg agtaataacg tcctgctgct gttctcatat gaatatcctc    60
cttag    65

<210> SEQ ID NO 110
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 110
gtgtcccgta ttattatgct gatccctacc ggaaccagcg tcggtgtgta ggctggagct    60
gcttc    65

<210> SEQ ID NO 111
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 111
ttactgctgc tgtgcagact gaatcgcagt cagcgcgatg gtgtacatat gaatatcctc    60
cttag    65

<210> SEQ ID NO 112
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 112
atgaaacaaa cggttgcagc ttatatcgcc aaaacactcg aatcggtgta ggctggagct    60
gcttc    65

<210> SEQ ID NO 113
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 113
ttaccttagc cagtttgttt tcgccagttc gatcacttca tcacccatat gaatatcctc    60
cttag    65

<210> SEQ ID NO 114
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 114
atgaccatta ctccggcaac tcatgcaatt tcgataaatc ctgccgtgta ggctggagct    60
gcttc    65

<210> SEQ ID NO 115
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 115
tcagatccgg tctttccaca ccgtctggat attacagaat tcgtgcatat gaatatcctc    60
cttag                                                                65

<210> SEQ ID NO 116
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 116
atgaaactta acgacagtaa cttattccgc cagcaggcgt tgattgtgta ggctggagct    60
gcttc                                                                65

<210> SEQ ID NO 117
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 117
ttaaagaccg atgcacatat atttgatttc taagtaatct tcgatcatat gaatatcctc    60
cttag                                                                65

<210> SEQ ID NO 118
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 118
atggaccaga agctgttaac ggatttccgc tcagaactac tcgatgtgta ggctggagct    60
gcttc                                                                65

<210> SEQ ID NO 119
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 119
tcaggtgtgt ttaaagctgt tctgctgggc aatccctgc agtttcatat gaatatcctc     60
cttag                                                                65

<210> SEQ ID NO 120
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 120
atggataaga agcaagtaac ggatttaagg tcggaactac tcgatgtgta ggctggagct     60
gcttc                                                                65

<210> SEQ ID NO 121
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 121
tcaggtatgt ttaaagctgt tctgttgggc aataccctgc agtttcatat gaatatcctc     60
cttag                                                                65

<210> SEQ ID NO 122
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 122
atggctacat cagtacagac aggtaaagct aagcagctca cattagtgta ggctggagct     60
gcttc                                                                65

<210> SEQ ID NO 123
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 123
ttagtgtttc ttgtcattca tcacaatata gtgtggtgaa cgtgccatat gaatatcctc     60
cttag                                                                65

<210> SEQ ID NO 124
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 124
atggaaccaa aaacaaaaaa acagcgttcg ctttatatcc cttacgtgta ggctggagct     60
gcttc                                                                65

<210> SEQ ID NO 125
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 125
ttagatggag gtacggcggt agtcgcggta ttcggcttgc cagaacatat gaatatcctc     60
cttag                                                                65

<210> SEQ ID NO 126
<211> LENGTH: 65
<212> TYPE: DNA

<213> ORGANISM: Artificial Sequence
<220> FEATURE:
<223> OTHER INFORMATION: Synthetic Construct - Primer for amplification

<400> SEQUENCE: 126
atggatgacc agttaaaaca aagtgcactt gatttccatg aatttgtgta ggctggagct    60
gcttc    65

<210> SEQ ID NO 127
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 127
ttacagcggt tgggtttgcg cttctaccac ggccagcgcc accatcatat gaatatcctc    60
cttag    65

<210> SEQ ID NO 128
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 128
atgaacgaac aatattccgc attgcgtagt aatgtcagta tgctcgtgta ggctggagct    60
gcttc    65

<210> SEQ ID NO 129
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 129
ttagccggta ttacgcatac ctgccgcaat cccggcaata gtgaccatat gaatatcctc    60
cttag    65

<210> SEQ ID NO 130
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 130
atgtccagaa ggcttcgcag aacaaaaatc gttaccacgt taggcgtgta ggctggagct    60
gcttc    65

<210> SEQ ID NO 131
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 131
ttactctacc gttaaaatac gcgtggtatt agtagaaccc acggtcatat gaatatcctc    60
cttag    65

<210> SEQ ID NO 132
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 132
atgaaaaaga ccaaaattgt ttgcaccatc ggaccgaaaa ccgaagtgta ggctggagct    60
gcttc    65

<210> SEQ ID NO 133
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 133
ttacaggacg tgaacagatg cggtgttagt agtgccgctc ggtaccatat gaatatcctc    60
cttag    65

<210> SEQ ID NO 134
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 134
atggaactga cgactcgcac tttacctgcg cggaaacata ttgcggtgta ggctggagct    60
gcttc    65

<210> SEQ ID NO 135
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 135
ttacttcaga cggtccgcga gataacgctg ataatcgggg atcagcatat gaatatcctc    60
cttag    65

<210> SEQ ID NO 136
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 136
atggtcgcac ccattcccgc gaaacgcggc agaaaacccg ccgttgtgta ggctggagct    60
gcttc    65

<210> SEQ ID NO 137
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 137
tcagcgcatt ccaccgtacg ccagcgtcac ttccttcgcc gctttcatat gaatatcctc    60
cttag    65

<210> SEQ ID NO 138
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 138
atggaaagta aagtagttgt tccggcacaa ggcaagaaga tcaccgtgta ggctggagct    60
gcttc    65

<210> SEQ ID NO 139
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 139
ttacatgttt tcgatgatcg cgtcaccaaa ctctgaacat ttcagcatat gaatatcctc    60
cttag    65

<210> SEQ ID NO 140
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 140
atgcagaaca gcgctttgaa agcctggttg gactcttctt acctcgtgta ggctggagct    60
gcttc    65

<210> SEQ ID NO 141
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 141
ttattcgacg ttcagcgcgt cattaaccag atcttgttgc tgtttcatat gaatatcctc    60
cttag    65

<210> SEQ ID NO 142
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 142
atgagtagcg tagatattct ggtccctgac ctgcctgaat ccgtagtgta ggctggagct    60
gcttc    65

<210> SEQ ID NO 143
<211> LENGTH: 65

```
<212> TYPE: DNA
<213> ORGANISM: Artificial Sequence
<220> FEATURE:
<223> OTHER INFORMATION: Synthetic Construct - Primer for amplification

<400> SEQUENCE: 143
ctacacgtcc agcagcagac gcgtcggatc ttccagcaac tctttcatat gaatatcctc    60
cttag                                                                65

<210> SEQ ID NO 144
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 144
gtgcaaacct ttcaagccga tcttgccatt gtaggcgccg gtggcgtgta ggctggagct    60
gcttc                                                                65

<210> SEQ ID NO 145
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 145
tcagccattc gccttctcct tcttattggc tgcttccgcc ttatccatat gaatatcctc    60
cttag                                                                65

<210> SEQ ID NO 146
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 146
atggctgaga tgaaaaacct gaaaattgag gtggtgcgct ataacgtgta ggctggagct    60
gcttc                                                                65

<210> SEQ ID NO 147
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 147
ttagcgtggt ttcagggtcg cgataagaaa gtctttcgaa ctttccatat gaatatcctc    60
cttag                                                                65

<210> SEQ ID NO 148
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 148
atgacgacta aacgtaaacc gtatgtacgg ccaatgacgt ccaccgtgta ggctggagct    60
``` gcttc 65

<210> SEQ ID NO 149
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 149
ttaccagtac agggcaacaa acaggattac gatggtggca accaccatat gaatatcctc    60
cttag    65

<210> SEQ ID NO 150
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 150
atgattaatc caaatccaaa gcgttctgac gaaccggtat tctgggtgta ggctggagct    60
gcttc    65

<210> SEQ ID NO 151
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 151
ttagattgta acgacaccaa tcagcgtgac aactgtcagg atagccatat gaatatcctc    60
cttag    65

<210> SEQ ID NO 152
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 152
atgtttaaga atgcatttgc taacctgcaa aaggtcggta aatcggtgta ggctggagct    60
gcttc    65

<210> SEQ ID NO 153
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 153
ttagtggtta cggatgtact catccatctc ggttttcagg ttatccatat gaatatcctc    60
cttag    65

<210> SEQ ID NO 154
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 154
atgatttcag gcattttagc atccccgggt atcgctttcg gtaaagtgta ggctggagct    60
gcttc    65

<210> SEQ ID NO 155
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 155
ttagcagatt gtttttctt caatgaactt gttaaccagc gtcatcatat gaatatcctc    60
cttag    65

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 156
cggtgccctg aatgaactgc    20

<210> SEQ ID NO 157
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 157
cagtcatagc cgaatagcct    20

<210> SEQ ID NO 158
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 158
atacgtgtcc cgagcggtag    20

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 159
tacacatccc gccatcagca    20

<210> SEQ ID NO 160
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 160
gaagtaaacg ggaaaatcaa                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 161
agaagtggca taagaaaacg                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 162
ccattggctg aaaattacgc                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 163
gttccattgc acggatcacg                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 164
atgccgtaga agccgccagt                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 165
tgttggtgcg cagctcgaag                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 166
gcaaatctgg tttcatcaac                                               20

<210> SEQ ID NO 167
<211> LENGTH: 20
<212> TYPE: DNA
<213> ORGANISM: Artificial Sequence

```
<220> FEATURE:
<223> OTHER INFORMATION: Synthetic Construct - Primer for amplification

<400> SEQUENCE: 167
tcccttgcac aaaacaaagt                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 168
ggatttggtt ctcgcataat                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 169
agcattaacg gtagggtcgt                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 170
gctgattctc gcgaataaac                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 171
aaaaacgttc ttgcgcgtct                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 172
tctgtttgtc accacccgc                                                20

<210> SEQ ID NO 173
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 173
aagccagcac ctggaagcag                                               20
```

<210> SEQ ID NO 174
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 174
aagagctgcc gcaggaggat                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 175
gccgccctct taagtcaaat                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 176
ggattttagc aatattcgct                                              20

<210> SEQ ID NO 177
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 177
cctaatagca ggaagaagac                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 178
gctgaactgt tgctggaaga                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 179
ggcgtgcttt tacaactaca                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic Construct - Primer for amplification

```
<400> SEQUENCE: 180
tagtaaataa cccaaccggc                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 181
tcagtgagcg cagtgtttta                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 182
attaatggtg agagtttgga                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 183 tgctttttt tattattcgc                                                20

<210> SEQ ID NO 184
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 184
gctttataaa agacgacgaa                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 185
gtaacgacaa ttccttaagg                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 186
tttatatgcc catggtttct                                               20

<210> SEQ ID NO 187
```

```
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 187
atctgttaga ggcggatgat                                               20

<210> SEQ ID NO 188
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 188
ctggaacgtt aaatctttga                                               20

<210> SEQ ID NO 189
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 189
ccagtttagt agctttcatt                                               20

<210> SEQ ID NO 190
<211> LENGTH: 25
<212> TYPE: DNA
<213> ORGANISM: Artificial Sequence
<220> FEATURE:
<223> OTHER INFORMATION: Synthetic Construct - Primer for amplification

<400> SEQUENCE: 190
gatttgttca acattaactc atcgg                                         25

<210> SEQ ID NO 191
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 191
tgcgattaac agacaccctt                                               20

<210> SEQ ID NO 192
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 192
tctcaggtgc tcacagaaca                                               20

<210> SEQ ID NO 193
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 193
```
tatggaagag gcgctactgc                                                20

<210> SEQ ID NO 194
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 194
cgacctgctg cataaacacc                                                20

<210> SEQ ID NO 195
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 195
tgaacgctaa ggtgattgca                                                20

<210> SEQ ID NO 196
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 196
acgtagacaa gagctcgcaa                                                20

<210> SEQ ID NO 197
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 197
catcacgtac gactgcgtcg                                                20

<210> SEQ ID NO 198
<211> LENGTH: 19
<212> TYPE: DNA
<213> ORGANISM: Artificial Sequence
<220> FEATURE:
<223> OTHER INFORMATION: Synthetic Construct - Primer for amplification

<400> SEQUENCE: 198
tgcaactttg tgctgagca                                                 19

<210> SEQ ID NO 199
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 199
tatcgcttcc gggcattgtc                                                20

<210> SEQ ID NO 200
<211> LENGTH: 25
<212> TYPE: DNA

```
<213> ORGANISM: Artificial Sequence
<220> FEATURE:
<223> OTHER INFORMATION: Synthetic Construct - Primer for amplification

<400> SEQUENCE: 200
aaatcgatct cgtcaaattt cagac                                          25

<210> SEQ ID NO 201
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 201
aggaaccaca aatcgccata                                                20

<210> SEQ ID NO 202
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 202
gacgtgaaga ttactacgct                                                20

<210> SEQ ID NO 203
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 203
agttcaatgc tgaaccacac                                                20

<210> SEQ ID NO 204
<211> LENGTH: 25
<212> TYPE: DNA
<213> ORGANISM: Artificial Sequence
<220> FEATURE:
<223> OTHER INFORMATION: Synthetic Construct - Primer for amplification

<400> SEQUENCE: 204
tagccgcgac cacggtaaga aggag                                          25

<210> SEQ ID NO 205
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 205
cagcgcatca cccggaaaca                                                20

<210> SEQ ID NO 206
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 206
atcgtgatca ttaacctgat                                                20
```

```
<210> SEQ ID NO 207
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 207
ttaccctgat aaattaccgc                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 208
ccatccgttg aatgagtttt                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 209
tggtgttaac tggcaaaatc                                               20

<210> SEQ ID NO 210
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 210
gtgacttcca acggcaaaag                                               20

<210> SEQ ID NO 211
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 211
ccgttggttt gatagcaata                                               20

<210> SEQ ID NO 212
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 212
tataatcccg ggatgcgcgt taacaatggt ttgacc                             36

<210> SEQ ID NO 213
<211> LENGTH: 32
<212> TYPE: DNA
<213> ORGANISM: Artificial Sequence
<220> FEATURE:
```

<223> OTHER INFORMATION: Synthetic Construct - Primer for amplification

<400> SEQUENCE: 213
tataattcta gattacagtt tcggaccagc cg                                        32

<210> SEQ ID NO 214
<211> LENGTH: 30
<212> TYPE: DNA
<213> ORGANISM: Artificial Sequence
<220> FEATURE:
<223> OTHER INFORMATION: Synthetic Construct - Primer for amplification

<400> SEQUENCE: 214
tataatcccg ggatgaacga acaatattcc                                           30

<210> SEQ ID NO 215
<211> LENGTH: 30
<212> TYPE: DNA
<213> ORGANISM: Artificial Sequence
<220> FEATURE:
<223> OTHER INFORMATION: Synthetic Construct - Primer for amplification

<400> SEQUENCE: 215
tataattcta gattagccgg tattacgcat                                           30

<210> SEQ ID NO 216
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 216
tataatcccg ggatgtccag aaggcttcgc agaaca                                    36

<210> SEQ ID NO 217
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 217
tataattcta gattactcta ccgttaaaat ac                                        32

<210> SEQ ID NO 218
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 218
tataatcccg ggatgaaaac ccgtacacaa caaatt                                    36

<210> SEQ ID NO 219
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 219
tataattcta gattagaact gcgattcttc ag                                        32

```
<210> SEQ ID NO 220
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 220
tataatcccg ggatgaaaaa actactcgtc gccaat                              36

<210> SEQ ID NO 221
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 221
tataattcta gattaattaa tttcgattaa ca                                  32

<210> SEQ ID NO 222
<211> LENGTH: 40
<212> TYPE: DNA
<213> ORGANISM: Artificial Sequence
<220> FEATURE:
<223> OTHER INFORMATION: Synthetic Construct - Primer for amplification

<400> SEQUENCE: 222
tataatcccg ggatgcctga cgctaaaaaa cagggggcggt                         40

<210> SEQ ID NO 223
<211> LENGTH: 33
<212> TYPE: DNA
<213> ORGANISM: Artificial Sequence
<220> FEATURE:
<223> OTHER INFORMATION: Synthetic Construct - Primer for amplification

<400> SEQUENCE: 223
tataattcta gattaatcgt gagcgcctat ttc                                 33

<210> SEQ ID NO 224
<211> LENGTH: 1083
<212> TYPE: DNA
<213> ORGANISM: Metallosphaera sedula

<400> SEQUENCE: 224
atgaaagctg cagtacttca tacgtataag gaaccgctgt ccattgagga cgtgaatatc    60
tcccaaccta aggctgggga agtcaagatc aaggtcaagg caaccggtct ctgtcgctcc   120
gacgtcaatg tctttgaggg gaaaaccccca gttcctcccc cagtggttgc tggacacgaa   180
atatcaggga ttgtggagga agtgggacct ggggtgacca gggttaaacc aggtgatagg   240
gtgatttcag cgtttattca cccctgtggt aaatgcggta actgcgttgc aggaaaggag   300
aatctgtgtg agaccttctc ccaggtcaga ctcaagggag taatgccaga tggaacgtca   360
aggctgtcaa aggacggaaa ggagataagg actttccttg gaggcggttt cgcggagtac   420
gccattgtgg gagagaacgc gctaaccagg gttccagagg acatggacct agagaaggta   480
gctgtcctag gttgtgctgg gttaacaggg tacggtgcca tatcatcatc caagattgag   540
cctggagaca ctgtggccgt gataggcgta ggaggagtgg gtttgtccac aatacaactc   600
ctaagggcct cgggtgccgg gaggataatc gccgtgggaa cgaaaaagtg gaaacttgac   660
agggccatgg agctaggtgc aactgacgtg gtaaactcga aggagataga tcccgtcaaa   720
```

-continued

```
gcaataaagg agatcacggg tggagggcca caggtggtga tagaggctgg aggaaatgag    780
gatacgattc atatggcgct ggattcagtt agaattggag gaaaggtggt tctggtaggg    840
ttacctccag caacggccat gatacccatc agggtagcgt caatagttag gggaggcata    900
gaggttgtgg ggaattacgg aggaagacct agggttgata tgcccaagct tctcgagcta    960
gtgaggcagg gaagatacga tccgtctagg cttgtgacgg gtagattcag gttggaggaa   1020
ataaatgagg cagtcaaaat gcttgaggaa ggagaggcca taagaagtct cataatcccg   1080
taa                                                                  1083
```

<210> SEQ ID NO 225
<211> LENGTH: 360
<212> TYPE: PRT
<213> ORGANISM: Metallosphaera sedula

<400> SEQUENCE: 225

```
Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
            20                  25                  30

Lys Ala Thr Gly Leu Cys Arg Ser Asp Val Asn Val Phe Glu Gly Lys
        35                  40                  45

Thr Pro Val Pro Pro Val Ala Gly His Glu Ile Ser Gly Ile
    50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu
        115                 120                 125

Ile Arg Thr Phe Leu Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205

Ile Ile Ala Val Gly Thr Lys Lys Trp Lys Leu Asp Arg Ala Met Glu
    210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Gly Pro Gln Val Val Ile Glu Ala
                245                 250                 255

Gly Gly Asn Glu Asp Thr Ile His Met Ala Leu Asp Ser Val Arg Ile
            260                 265                 270

Gly Gly Lys Val Val Leu Val Gly Leu Pro Pro Ala Thr Ala Met Ile
        275                 280                 285

Pro Ile Arg Val Ala Ser Ile Val Arg Gly Gly Ile Glu Val Val Gly
    290                 295                 300
```

Asn Tyr Gly Gly Arg Pro Arg Val Asp Met Pro Lys Leu Leu Glu Leu
305                 310                 315                 320

Val Arg Gln Gly Arg Tyr Asp Pro Ser Arg Leu Val Thr Gly Arg Phe
            325                 330                 335

Arg Leu Glu Glu Ile Asn Glu Ala Val Lys Met Leu Glu Glu Gly Glu
        340                 345                 350

Ala Ile Arg Ser Leu Ile Ile Pro
        355                 360

<210> SEQ ID NO 226
<211> LENGTH: 1083
<212> TYPE: DNA
<213> ORGANISM: Metallosphaera sedula

<400> SEQUENCE: 226

| | | | | | |
|---|---|---|---|---|---|
| atgaaagctg | cagtacttca | tacgtataag | gaaccgctgt | ccattgagga | cgtgaatatc | 60 |
| tcccaaccta | aggctgggga | agtcaagatc | aaggtcaagg | caaccgggct | ctgtcactcc | 120 |
| gacgtacatg | tctttgaggg | gaaaacccca | gttcctcccc | cagtggttgc | tggacacgaa | 180 |
| atatcaggga | ttgtggagga | agtgggacct | ggggtgacca | gggttaaacc | aggtgatagg | 240 |
| gtgatttcag | cgtttattca | cccctgtggt | aaatgcggta | actgcgttgc | aggaaaggag | 300 |
| aatctgtgtg | agaccttctc | ccaggtcaga | ctcaagggag | taatgccaga | tggaacgtca | 360 |
| aggctgtcaa | aggacggaaa | ggagataagg | actttccttg | gaggcggttt | cgcggagtac | 420 |
| gccattgtgg | gagagaacgc | gctaaccagg | gttccagagg | acatggacct | agagaaggta | 480 |
| gctgtcctag | gttgtgctgg | gttaacaggg | tacggtgcca | tatcatcatc | caagattgag | 540 |
| cctggagaca | ctgtggccgt | gataggcgta | ggaggagtgg | gtttgtccac | aatacaactc | 600 |
| ctaagggcct | cgggtgccgg | gaggataatc | gccgtgggaa | cgaaaaagtg | gaaacttgac | 660 |
| agggccatgg | agctaggtgc | aactgacgtg | gtaaactcga | aggagataga | tcccgtcaaa | 720 |
| gcaataaagg | agatcacggg | tggagggcca | caggtggtga | tagaggctgg | aggaaatgag | 780 |
| gatacgattc | atatggcgct | ggattcagtt | agaattggag | gaaaggtggt | tctggtaggg | 840 |
| ttacctccag | caacggccat | gataccatc | agggtagcgt | caatagttag | ggaggcata | 900 |
| gaggttgtgg | ggaattacgg | aggaagacct | agggttgata | tgcccaagct | tctcgagcta | 960 |
| gtgaggcagg | gaagatacga | tccgtctagg | cttgtgacgg | gtagattcag | gttggaggaa | 1020 |
| ataaatgagg | cagtcaaaat | gcttgaggaa | ggagaggcca | taagaagtct | cataatcccg | 1080 |
| taa | | | | | | 1083 |

<210> SEQ ID NO 227
<211> LENGTH: 360
<212> TYPE: PRT
<213> ORGANISM: Metallosphaera sedula

<400> SEQUENCE: 227

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
            20                  25                  30

Lys Ala Thr Gly Leu Cys His Ser Asp Val His Val Phe Glu Gly Lys
        35                  40                  45

Thr Pro Val Pro Pro Val Val Ala Gly His Glu Ile Ser Gly Ile
    50                  55                  60

Val Glu Glu Val Gly Pro Gly Val Thr Arg Val Lys Pro Gly Asp Arg

```
                65                  70                  75                  80
        Val Ile Ser Ala Phe Ile His Pro Cys Gly Lys Cys Gly Asn Cys Val
                        85                  90                  95
        Ala Gly Lys Glu Asn Leu Cys Glu Thr Phe Ser Gln Val Arg Leu Lys
                        100                 105                 110
        Gly Val Met Pro Asp Gly Thr Ser Arg Leu Ser Lys Asp Gly Lys Glu
                        115                 120                 125
        Ile Arg Thr Phe Leu Gly Gly Phe Ala Glu Tyr Ala Ile Val Gly
                130                 135                 140
        Glu Asn Ala Leu Thr Arg Val Pro Glu Asp Met Asp Leu Glu Lys Val
        145                 150                 155                 160
        Ala Val Leu Gly Cys Ala Gly Leu Thr Gly Tyr Gly Ala Ile Ser Ser
                        165                 170                 175
        Ser Lys Ile Glu Pro Gly Asp Thr Val Ala Val Ile Gly Val Gly Gly
                        180                 185                 190
        Val Gly Leu Ser Thr Ile Gln Leu Leu Arg Ala Ser Gly Ala Gly Arg
                        195                 200                 205
        Ile Ile Ala Val Gly Thr Lys Lys Trp Lys Leu Asp Arg Ala Met Glu
                210                 215                 220
        Leu Gly Ala Thr Asp Val Val Asn Ser Lys Glu Ile Asp Pro Val Lys
        225                 230                 235                 240
        Ala Ile Lys Glu Ile Thr Gly Gly Pro Gln Val Val Ile Glu Ala
                        245                 250                 255
        Gly Gly Asn Glu Asp Thr Ile His Met Ala Leu Asp Ser Val Arg Ile
                        260                 265                 270
        Gly Gly Lys Val Val Leu Val Gly Leu Pro Pro Ala Thr Ala Met Ile
                        275                 280                 285
        Pro Ile Arg Val Ala Ser Ile Val Arg Gly Gly Ile Glu Val Val Gly
                        290                 295                 300
        Asn Tyr Gly Gly Arg Pro Arg Val Asp Met Pro Lys Leu Leu Glu Leu
        305                 310                 315                 320
        Val Arg Gln Gly Arg Tyr Asp Pro Ser Arg Leu Val Thr Gly Arg Phe
                        325                 330                 335
        Arg Leu Glu Glu Ile Asn Glu Ala Val Lys Met Leu Glu Glu Gly Glu
                        340                 345                 350
        Ala Ile Arg Ser Leu Ile Ile Pro
                        355                 360

<210> SEQ ID NO 228
<211> LENGTH: 1083
<212> TYPE: DNA
<213> ORGANISM: Artificial Sequence
<220> FEATURE:
<223> OTHER INFORMATION: Synthetic Construct - M. sedula codon optimized
      sequence

<400> SEQUENCE: 228
atgaaagcag cagttctgca tacctataaa gaaccgctga gcattgaaga tgtgaatatt    60
tcacagccga agccggtga agtgaaaatc aaagttaaag caaccggtct gtgtcgtagt   120
gatgttcatg tttttgaagg taaaacaccg gttccgcctc cggttgttgc aggtcatgaa   180
attagcggta ttgttgaaga ggttggtccg ggtgttaccc gtgttaaacc gggtgatcgt   240
gttattagcg catttattca tccgtgtggt aaatgcggta ttgtgttgc cggtaaagaa   300 aatctgtgtg aaacctttag ccaggttcgt ctgaaaggtg ttatgccgga tggcaccagc   360
```

```
cgtctgagca aagatggcaa agaaattcgt acctttctgg gtggtggttt tgcagaatat    420
gcaattgttg gtgaaaatgc actgacccgt gttccggaag atatggatct ggaaaaagtt    480
gcagttctgg gttgtgccgg tctgaccggt tatggtgcaa ttagcagcag caaaattgaa    540
cctggtgata ccgttgcagt tattggtgtt ggtggtgtgg gtctgagcac cattcagctg    600
ctgcgtgcaa gcggtgcagg tcgtattatt gcagttggca ccaaaaaatg gaaactggat    660
cgtgcaatgg aactgggtgc aaccgatgtt gttaacagta agaaattgat tccggtgaaa    720
gccatcaaag aaatcaccgg tggtggtccg caggttgtta ttgaagccgg tggtaatgaa    780
gataccattc acatggcact ggatagcgtt cgtattggtg gtaaagttgt tctggttggt    840
ctgcctccgg caaccgcaat gattccgatt cgtgttgcaa gcattgttcg tggtggtatt    900
gaagttgttg gtaattatgg tggtcgtccg cgtgttgata tgccgaaact gctggaactg    960
gttcgtcagg gtcgttatga tccgagccgt ctggttaccg gtcgttttcg tctggaagaa   1020
attaatgaag ccgtcaaaat gctggaagaa ggtgaagcaa ttcgtagcct gattattccg   1080
taa                                                                 1083
```

<210> SEQ ID NO 229  
<211> LENGTH: 4107  
<212> TYPE: DNA  
<213> ORGANISM: Artificial Sequence  
<220> FEATURE:  
<223> OTHER INFORMATION: Synthetic Construct - chimeric gene for the
    expression of malate kinase, malate semi aldehyde dehydrognase and
    DHB dehydrogenase

<400> SEQUENCE: 229

```
ttgacaatta atcatcggct cgtataatgt gtggaattgt gagcggataa caatttcaca     60
caggaaacag aattcgagct cggtacccgg ggatcctcta gaaataattt tgtttaactt    120
taagaaggag atataccatg gcagcagcc atcatcatca tcatcacagc agcggcctgg    180
tgccgcgcgg cagccatatg tctgaaattg ttgtctccaa atttggcggt accagcgtag    240
ctgattttga cgccatgaac cgcagcgctg atattgtgct ttctgatgcc aacgtgcgtt    300
tagttgtcct ctcggcttct gctggtatca ctaatctgct ggtcgcttta gctgaaggac    360
tggaacctgg cgagcgattc gaaaaaactcg acgctatccg caacatccag tttgccattc    420
tggaacgtct gcgttacccg aacgttatcc gtgaagagat tgaacgtctg ctggagaaca    480
ttactgttct ggcagaagcg gcggcgctgg caacgtctcc ggcgctgaca gatgagctgg    540
tcagccatgg cggcctgatg tcgacctgc tgtttgttga tcctgcgc gaacgcgatg    600 ttcaggcaca gtggtttgat gtacgtaaag tgatgcgtac caacgaccga tttggtcgtg    660
cagagccaga tatagccgcg ctggcggaac tggccgcgct gcagctgctc ccacgtctca    720
atgaaggctt agtgatcacc cagggattta tcggtagcga aaataaaggt cgtacaacga    780
cgcttggccg tggaggcagc gattatacgg cagccttgct ggcggaggct ttacacgcat    840
ctcgtgttga tatctggacc gacgtcccgg gcatctacac caccgatcca cgcgtagttt    900
ccgcagcaaa acgcattgat gaaatcgcgt ttgccgaagc ggcaaagatg gccactttg    960 gtgcaaaagt actgcatccg gcaacgttgc tacccgcagt acgcagcgat atcccggtct   1020
ttgtcggctc cagcaaagac ccacgcgcag tggtacgct ggtgtgcaat aaaactgaaa    1080
atccgccgct gttccgcgct ctggcgcttc gtcgcaatca gactctgctc actttgcaca    1140
gcctgaatat gctgcattct cgcggtttcc tcgcggaagt tttcggcatc ctcgcgcggc   1200
ataatatttc ggtagactta atcaccacgt cagaagtgag cgtggcatta acccttgata    1260
```

```
ccaccggttc aacctccact ggcgatacgt tgctgacgca atctctgctg atggagcttt      1320
ccgcactgtg tcgggtggag gtggaagaag gtctggcgct ggtcgcgttg attggcaatg      1380
acctgtcaaa agcctgcggc gttggcaaag aggtattcgg cgtactggaa ccgttcaaca      1440
ttcgcatgat ttgttatggc gcatccagcc ataacctgtg cttcctggtg cccggcgaag      1500
atgccgagca ggtggtgcaa aaactgcata gtaatttgtt tgagtaaata ctggatccgt      1560
ttaactttaa gaaggagata taccatgggc agcagccatc atcatcatca tcacagcagc      1620
ggcctggtgc cgcgcggcag ccatatggct agcatgaaaa atgttggttt tatcggctgg      1680
cgcggtatgg tcggctccgt tctcatgcaa cgcatggttg aagagcgcga cttcgacgcc      1740
attcgccctg tcttcttttc tacttctcag cttggccagg ctgcgccgtc ttttggcgga      1800
accactggca cacttcagga tgcctttgat ctggaggcgc taaaggccct cgatatcatt      1860
gtgacctgtc agggcggcga ttataccaac gaaatctatc aaagcttcg tgaaagcgga       1920
tggcaaggtt actggattga cgcagcatcg tctctgcgca tgaaagatga cgccatcatc      1980
attcttgacc ccgtcaatca ggacgtcatt accgacggat aaataatgg catcaggact       2040
tttgttggcg gtaactgtac cgtaagcctg atgttgatgt cgttgggtgg tttattcgcc      2100
aatgatcttg ttgattgggt gtccgttgca acctaccagg ccgcttccgg cggtggtgcg      2160
cgacatatgc gtgagttatt aacccagatg ggccatctgt atggccatgt ggcagatgaa      2220
ctcgcgaccc cgtcctctgc tattctcgat atcgaacgca aagtcacaac cttaacccgt      2280
agcggtgagc tgccggtgga taactttggc gtgccgctgg cgggtagcct gattccgtgg      2340
atcgacaaac agctcgataa cggtcagagt cgacaggagt ggaaagggca ggcggaaacc      2400
aacaagatcc tcaacacatc ttccgtaatt ccggtagatg gtttatgtgt gcgtgtcggg      2460
gcattgcgct gccacagcca ggcattcact attaaattga aaaagatgt gtctattccg       2520
accgtggaag aactgctggc tgcgcacaat ccgtgggcga aagtcgttcc gaacgatcgg      2580
gaaatcacta tgcgtgagct aaccccagct gccgttaccg gcacgctgac cacgccggta      2640
ggccgcctgc gtaagctgaa tatgggacca gagttcctgt cagcctttac cgtgggcgac      2700
cagctgctgt gggggccgc ggagccgctg cgtcggatgc ttcgtcaact ggcgtaagaa       2760
ttcgagctcc gtcgacaagc ttgcggccgc gtttaacttt aagaaggaga tataccatgg      2820
gcagcagcca tcatcatcat catcacagca gcggcctggt gccgcgcggc agccatatgg      2880
ctagcatgaa agcagcagtt ctgcatacct ataaagaacc gctgagcatt gaagatgtga      2940
atatttcaca gccgaaagcc ggtgaagtga aaatcaaagt taaagcaacc ggtctgtgtc      3000
gtagtgatgt tcatgttttt gaaggtaaaa caccggttcc gcctccggtt gttgcaggtc      3060
atgaaattag cggtattgtt gaagaggttg gtccgggtgt tacccgtgtt aaaccgggtg      3120
atcgtgttat tagcgcattt attcatccgt gtggtaaatg cggtaattgt gttgccggta      3180
aagaaaatct gtgtgaaacc tttagccagg ttcgtctgaa aggtgttatg ccggatggca      3240
ccagccgtct gagcaaagat ggcaaagaaa ttcgtaccct tctgggtggt ggttttgcag      3300
aatatgcaat tgttggtgaa aatgcactga cccgtgttcc ggaagatatg gatctggaaa      3360
aagttgcagt tctgggttgt gccggtctga ccggttatgt gcaattagc agcagcaaaa       3420
ttgaacctgg tgataccgtt gcagttattg gtgttggtgg tgtgggtctg agcaccattc      3480
agctgctgcg tgcaagcggt gcaggtcgta ttattgcagt tggcaccaaa aaatggaaac      3540
tggatcgtgc aatggaactg ggtgcaaccg atgttgttaa cagtaaagaa attgatccgg      3600
```

```
tgaaagccat caaagaaatc accggtggtg gtccgcaggt tgttattgaa gccggtggta    3660
atgaagatac cattcacatg gcactggata gcgttcgtat tggtggtaaa gttgttctgg    3720
ttggtctgcc tccggcaacc gcaatgattc cgattcgtgt tgcaagcatt gttcgtggtg    3780
gtattgaagt tgttggtaat tatggtggtc gtccgcgtgt tgatatgccg aaactgctgg    3840
aactggttcg tcagggtcgt tatgatccga gccgtctggt taccggtcgt tttcgtctgg    3900
aagaaattaa tgaagccgtc aaaatgctgg aagaaggtga agcaattcgt agcctgatta    3960
ttccgtaagc tcgagcacca ccaccaccac cactgagatc cggctgctaa caaagcccga    4020
aaggaagctg agttggctgc tgccaccgct gagcaataac tagcataacc ccttggggcc    4080
tctaaacggg tcttgagggg ttttttg                                       4107
```

<210> SEQ ID NO 230
<211> LENGTH: 1104
<212> TYPE: DNA
<213> ORGANISM: Escherichia coli

<400> SEQUENCE: 230

```
atgaaaaatg ttggttttat cggctggcgc ggtatggtcg gctccgttct catgcaacgc      60
atggttgaag agcgcgactt cgacgccatt cgccctgtct tctttttctac ttctcagctt    120 ggccaggctg cgccgtcttt tggcggaacc actggcacac ttcaggatgc ctttgatctg    180
gaggcgctaa aggccctcga tatcattgtg acctgtcagg cggcgattaa taccaacgaa    240
atctatccaa agcttcgtga agcggatggc aaggttact  ggattgacgc agcatcgtct    300
ctgcgcatga agatgacgc catcatcatt cttgaccccg tcaatcagga cgtcattacc    360
gacggattaa ataatggcat caggactttt gttggcggta actgtaacgt gtccctgatg    420
ttgatgtcgt tgggtggttt attcgccaat gatcttgttg attgggtgtc cgttgcaacc    480
taccaggccg cttccggcgg tggtgcgcga catatgcgtg agttattaac ccagatgggc    540
catctgtatg gccatgtggc agatgaactc gcgaccccgt cctctgctat tctcgatatc    600
gaacgcaaag tcacaaacctt aacccgtagc ggtgagctgc cggtggataa cttt ggcgtg    660 ccgctggcgg gtagcctgat tccgtggatc gacaaacagc tcgataacgg tcagagtcga    720
caggagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac cccagctgcc    960
gttaccggca cgctgaccac gccggtaggc cgcctgcgta agctgaatat gggaccagag   1020
ttcctgtcag cctttaccgt gggcgaccag ctgctgtggg gggccgcgga gccgctgcgt   1080
cggatgcttc gtcaactggc gtaa                                          1104
```

<210> SEQ ID NO 231
<211> LENGTH: 367
<212> TYPE: PRT
<213> ORGANISM: Escherichia coli

<400> SEQUENCE: 231

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly

```
                35                  40                  45
Gly Thr Thr Gly Thr Leu Gln Asp Ala Phe Asp Leu Glu Ala Leu Lys
        50                  55                  60

Ala Leu Asp Ile Ile Val Thr Cys Gln Gly Gly Asp Tyr Thr Asn Glu
 65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
                100                 105                 110

Pro Val Asn Gln Asp Val Ile Thr Asp Gly Leu Asn Asn Gly Ile Arg
                115                 120                 125

Thr Phe Val Gly Gly Asn Cys Asn Val Ser Leu Met Leu Met Ser Leu
        130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
                180                 185                 190

Pro Ser Ser Ala Ile Leu Asp Ile Glu Arg Lys Val Thr Thr Leu Thr
                195                 200                 205

Arg Ser Gly Glu Leu Pro Val Asp Asn Phe Gly Val Pro Leu Ala Gly
        210                 215                 220

Ser Leu Ile Pro Trp Ile Asp Lys Gln Leu Asp Asn Gly Gln Ser Arg
225                 230                 235                 240

Gln Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
                260                 265                 270

Cys His Ser Gln Ala Phe Thr Ile Lys Leu Lys Lys Asp Val Ser Ile
                275                 280                 285

Pro Thr Val Glu Glu Leu Leu Ala Ala His Asn Pro Trp Ala Lys Val
        290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
                340                 345                 350

Trp Gly Ala Ala Glu Pro Leu Arg Arg Met Leu Arg Gln Leu Ala
        355                 360                 365
```

METHOD OF PRODUCTION OF 2,4-DIHYDROXYBUTYRIC ACID

This is a continuation of application Ser. No. 13/882,372 filed Jun. 20, 2013, which is a National Stage Application of PCT/IB2011/002870 filed Oct. 27, 2011, and claims the benefit of International Application Nos. PCT/IB2010/003153 filed Oct. 28, 2010 and PCT/IB2011/001559 filed May 23, 2011. The entire disclosures of the prior applications are hereby incorporated by reference in their entirety.

The present invention relates to a novel method of production of 2,4-dihydroxybutyric acid from malate by the implementation of a synthetic pathway that comprises enzymes having malate kinase, malate semialdehyde dehydrogenase, and 2,4-dihydroxybutyrate dehydrogenase activity, respectively.

The carboxylic acids cited within the present application are equally named under their salt (e.g. 2,4-dihydroxyburyrate) or acid forms (e.g. 2,4-dihydroxybutyric acid).

2,4-dihydroxybutyric acid (equally 2,4-DHB or DHB) is a compound of considerable economic interest. DHB can be readily converted into α-hydroxy-γ-butyrolactone in aqueous media by adjusting the appropriate pH. α-hydroxy-γ-butyrolactone is a prominent precursor for the production of the methionine substitute 2-hydroxy-4-(methylthio)-butyrate (HMTB) (Deck et al., 2008) which has a large market in animal nutrition. At present, α-hydroxy-γ-butyrolactone is derived from γ-butyrolactone by a multi-stage process that implies halogenation of the γ-butyrolactone in position α, and subsequent substitution of the halogen atom by a hydroxyl group in alkaline medium (Deck et al., 2008).

From growing oil prices the need for the production of DHB from renewable resources arises. Microorganisms are capable of transforming biomass-derived raw material, e.g. sugars or organic acids, into a large variety of different chemical compounds (Werpy & Petersen, 2004). With the growing body of biochemical and genomic information it is possible to modify microorganisms such that they overproduce naturally occurring metabolic intermediates with high yield and productivity (Bailey, 1991). Optimization of production microorganisms often requires rational engineering of metabolic networks which ensures, among others, overexpression of enzymes required for the biosynthesis of the metabolite of interest, and alleviation of product feedback inhibition. Another possibility is the implementation of novel enzymatic systems that catalyze the production of a metabolite of interest.

Metabolic engineering approaches and enzymatic catalyses require detailed knowledge on the biochemistry and regulation of the metabolic pathway leading to the metabolite of interest. In the case of DHB production, this information is not available. Only few studies report the occurrence of DHB in patients with succinic semialdehyde dehydrogenase deficiency (Shinka et al., 2002) without, however, identifying enzymatic reactions implicated in DHB production. The zymotic or enzymatic production of DHB, therefore, requires (i) the identification of a thermodynamically feasible pathway which transforms an accessible precursor into DHB, (ii) the identification or construction of enzymes that are capable to catalyze individual reaction steps in the pathway and (iii) the functional expression of the pathway enzymes in an appropriate production organism.

Accordingly, one object of the present invention is a method of producing 2,4-DHB comprising a first step of transforming malate in 4-phospho-malate using a malate kinase, a second step of transforming 4-phospho-malate in malate-4-semialdehyde using a malate semialdehyde dehydrogenase, a third step of transforming malate-4-semialdehyde in 2,4-DHB using a DHB dehydrogenase.

In the first reaction (see FIG. 1 (*i*)), malate (1) is converted into 4-phospho-malate (2) by the action of an enzyme which possesses malate kinase activity (A). In the second reaction (B), 4-phospho-malate is converted into malate-4-semialdehyde (3) by the action of an enzyme which possesses malate semialdehyde dehydrogenase activity. More precisely, reaction (B) is catalysed by an enzyme bearing dephosphorylating 4-phospho-malate reductase activity in the biosynthetic sense of the pathway. In the third reaction (C), malate-4-semialdehyde is converted into DHB (4) by the action of an enzyme which possesses DHB dehydrogenase activity. More precisely, reaction (C) is catalysed by an enzyme bearing malate-4-semialdehyde reductase activity in the biosynthetic sense of the pathway.

None of the above cited enzymes and intermediary products have been so far neither described nor identified in living cells. As such malate kinase, malate semialdehyde dehydrogenase, DHB dehydrogenase and 4-phospho-malate are further objects of the invention.

Within another aspect of the invention, the first step of the method of producing 2,4-DHB involves a malate kinase that is characterized in that it transforms malate into 4-phospho-malate. Said enzyme is obtainable by at least one mutation of an enzyme, said mutation(s) improving the activity and/or substrate affinity of the mutated enzyme for malate.

Within the present invention, the expression "improve the activity and/or substrate affinity" means that the enzyme before mutation, was either unable to use the substrate (malate, 4-phospho-malate or malate-4-semialdehyde), and/or synthesized the product of the reaction (4-phospho-malate or malate-4-semialdehyde or DHB) at a maximum specific rate at least three times lower, and/or had an affinity for malate, 4-phospho-malate or malate-4-semialdehyde that was at least three times lower, and/or had an affinity for the natural substrate (aspartate, 4-phospho-asparte, aspartate-4-semialdehyde) which was at least 3 times higher.

Within another of its aspects the invention deals with the use of a malate kinase to transform malate into 4-phospho-malate.

The malate kinase activity can be measured by the enzymatic test described in example 1 (see "Enzymatic assay").

According to another aspect of the invention, the malate kinase can be obtained by mutation of an aspartate kinase.

FIG. 2 shows the alignment of amino acid sequences of aspartate kinases of different biological origin. All references to the position of amino acids are made based on the amino acid sequence of aspartate kinase encoded by the LysC gene of *E. coli* (represented by SEQ ID NO: 4). The relative positions of corresponding conserved regions in the other aspartate kinases from different organisms can easily be found by the man skilled in the art by simple sequence alignment as represented in FIG. 2 with enzymes listed below:

AKIII—aspartate kinase III of *E. Coli* (SEQ ID NO: 4),
AKI (SEQ ID NO: 87) aspartate kinase I of *E. coli*,
AKII (SEQ ID NO: 88)—aspartate kinase II of *E. coli*,
MJ—*Methanococcus jannaschii* (SEQ ID NO: 89),
TT—*Thermus thermophilus* (SEQ ID NO: 90),
CG—*Corynebacterium glutamicum* (SEQ ID NO: 91),
AT—*Arabidopsis thaliana* (SEQ ID NO: 92),
SC—*Saccharomyces cerevisiae*. (SEQ ID NO: 93).

Said alignment can be done with the ClustalW2 software. For example, the E119 residue of the aspartate kinase represented by SEQ ID NO: 4 corresponds to the E207 residue of the aspartate kinase of *A. thaliana* (SEQ ID NO: 50) or to the E147 residue of the aspartate kinase of *S. cerevisiae* (SEQ ID NO: 51).

The mutated aspartate kinase according to the invention comprises at least one mutation, when compared to the wild type enzyme, in at least one of the following positions: S39, T45, V115, E119, F184 and/or S201, wherein the naturally occurring amino acid in said positions is replaced by anyone of the other 19 naturally existing proteinogenic amino acids, that is by either alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

In a non-exclusive example, the construction of a malate kinase by site directed mutagenesis is demonstrated using the aspartate kinase Lys C of *Escherichia coli* as the template. According to one aspect of the invention, the substrate specificity of LysC was changed towards malate by replacing the glutamic acid in position 119 by either asparagine, glutamine, cysteine, proline, serine, threonine, valine or glycine.

Within a further aspect of the invention, the malate kinase is represented by SEQ ID NO: 9, and more specifically by SEQ ID NO:12, SEQ ID NO:14, SEQ ID NO:16, SEQ ID NO:18, SEQ ID NO:20, SEQ ID NO:22, SEQ ID NO:24 or SEQ ID NO:26.

Aspartate kinases are typically inhibited by either methionine, threonine or lysine. Therefore, malate kinases that were constructed by random or site directed mutagenesis of aspartate kinases may also be inhibited by said amino acids. In a further aspect of the invention, the inhibition of malate kinase by methionine, lysine or threonine is alleviated by mutagenesis of the malate kinase.

In a specific aspect of the invention, the above described mutated LysC (malate kinase) is rendered insensitive to lysine inhibition by mutation of at least one the following amino acids E250, M318, S321, V339, S338, F324, L325, V339, S345, E346, D340, T344 and/or T352 (see example 3).

The present invention also encompasses such modified enzymes and more particularly those represented by SEQ ID NO: 39, SEQ ID NO:41, SEQ ID NO:43 or SEQ ID NO:45.

Within a still further aspect, the second step of the method of producing 2,4-DHB according to the invention involves a malate semialdehyde dehydrogenase characterized in that it transforms 4-phospho-malate into malate-4-semialdehyde, said enzyme bearing a dephosphorylating 4-phospho-malate reductase activity in the biosynthetic sense of the pathway.

The malate semialdehyde dehydrogenase activity can be measured by the enzymatic test described in example 4 (see "Enzymatic assay").

This enzyme is obtainable by at least one mutation of an enzyme, said mutation(s) improving the activity and/or substrate affinity of the mutated enzyme for 4-phospho-malate.

According to another aspect, the malate semialdehyde dehydrogenase of the invention can be obtained by mutation of an enzyme having reported semialdehyde dehydrogenase activity, more specifically having dephosphorylating activity in the reductive sense of the reaction, more specifically acting on organic molecules that consist of 3, 4, or 5 carbon molecules. In a specific aspect of the invention said malate semialdehyde dehydrogenase is obtained by mutation of an aspartate semialdehyde dehydrogenase.

The aspartate semialdehyde dehydrogenase, Asd of *E. coli* and Hom2 of *Saccharomyces cerevisiae* naturally exhibit dehydrogenase activity on 4-phospho-malate 2.

According to another aspect of the invention, the malate semialdehyde dehydrogenase can be improved by the mutation of aspartate semialdehyde dehydrogenase.

FIG. 3 shows the alignment of amino acid sequences of aspartate semialdehyde dehydrogenases of different biological origin. All references to amino acids are made based on the aspartate semialdehyde dehydrogenase encoded by the Asd gene of *E. coli* (as represented by SEQ ID NO: 20). The relative positions of corresponding conserved regions in the other aspartate semialdehyde dehydrogenases from different organisms can easily be found by the man skilled in the art by simple sequence alignment as represented in FIG. 4 with enzymes listed below:

EC—*E. Coli* (SEQ ID NO: 49),
MJ—*Methanococcus jannaschii* (SEQ ID NO: 94),
TT—*Thermus thermophilus* (SEQ ID NO: 95),
BS—*Bacillus subtilis* (SEQ ID NO: 96),
CG—*Corynebacterium glutamicum* (SEQ ID NO: 97),
AT—*Arabidopsis thaliana* (SEQ ID NO: 98),
SC—*Saccharomyces cerevisiae*. (SEQ ID NO: 99)

Said alignment can easily be done using the ClustalW2 software.

The construction of enzymes having improved malate semialdehyde dehydrogenase activity can be done as follows.

The malate semialdehyde dehydrogenase according to the invention corresponds in a specific aspect to an aspartate semialdehyde dehydrogenase comprising at least one mutation when compared to the wild type enzyme in at least one of the positions T136, Q162, 1230, E241 and/or H274 wherein the naturally occurring amino acid in said positions is replaced by anyone of the other 19 naturally existing proteinogenic amino acids, that is by either alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

As demonstrated in Example 5, site-directed mutagenesis of asd from *E. coli* can improve activity and substrate affinity of the mutated enzyme for 4-phospho-malate, at the same time diminishing the preference of the enzyme for its natural substrate 4-phospho-aspartate.

In order to improve the activity of Asd on 4-phospho-malate, and according to one aspect of the invention, E241 was replaced by a glutamine, alanine, cysteine, glycine, histidine, isoleucine or methionine residue by site directed mutagenesis (Example 5).

Within a further aspect of the invention, the malate semialdehyde dehydrogenase is represented by SEQ ID NO: 68 and more specifically by SEQ ID NO:54, SEQ ID NO:56, SEQ ID NO:58, SEQ ID NO:60, SEQ ID NO:62, SEQ ID NO:64 or SEQ ID NO:66.

Within another of its aspect the invention deals with the use of a malate semialdehyde dehydrogenase to transform 4-phospho-malate in malate-4-semialdehyde.

Within another aspect, the third step of the method of producing 2,4-DHB according to the invention involves a DHB dehydrogenase characterized in that it transforms malate-4-semialdehyde into 2,4-DHB, said enzyme bearing malate-4-semialdehyde reductase activity in the biosynthetic sense of the pathway.

Candidate DHB dehydrogenase enzymes that potentially already possess DHB dehydrogenase activity can be chosen from the class of beta-hydroxyacid dehydrogenases that act on C3, C4, or C5 compounds.

According to a still further aspect of the invention, said DHB dehydrogenase enzymes can be structurally and mechanistically related to β-hydroxyacid dehydrogenases such as tartronate semialdehyde reductases, succinate semialdehyde reductases, malonate semialdehyde reductases, methylbutyraldehyde reductases, zinc-type alcohol dehydrogenases, L-threonine-3-dehydrogenases, or homoserine reductases.

The present invention also deals with the use of a methylbutyraldehyde reductase or of a succinic semialdehyde reductase to transform malate-4-semialdehyde in 2,4-DHB. In specific embodiments, said methylbutyraldehyde reductase is represented by SEQ ID NO: 74 and said succinic semialdehyde reductase is represented by SEQ ID NO: 76. The DHB dehydrogenase activity can be measured by the enzymatic test described in example 6 (see "Enzymatic assay").

The affinity of DHB dehydrogenase for malate-4-semi aldehyde can be increased by at least one mutation of an enzyme, said mutation(s) increasing the activity and/or substrate affinity of the mutated enzyme for malate-4-semi-aldehyde, and/or reducing the activity or affinity for its natural substrate by at least factor 2.

The DHB dehydrogenase according to the invention corresponds in a specific aspect to *M. sedula* succinic semialdehyde reductase (SEQ ID No76) comprising at least one mutation when compared to the wild type enzyme in at least one of the positions S40, N43, H39 T49, F85, Q108, L281 and N305 wherein the naturally occurring amino acid in said positions is replaced by anyone of the other 19 naturally existing proteinogenic amino acids, that is by either alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

As demonstrated in a non-exclusive example, the affinity of *M sedula* succinic semialdehyde reductase for (L)-malate-4-semialdehyde was increased by introducing the double mutation H39R N43H by site-directed mutagenesis, as represented by SEQ ID NO: 81. Simple mutants H39R (SEQ ID NO: 225) and N43H (SEQ ID NO: 227) are also encompassed by the present invention (Example 7).

DHB dehydrogenase can be used to transform malate-4-semialdehyde into 2,4-DHB, which constitutes a further aspect of the invention.

The nucleic acid sequence of genes can be adapted to the codon usage of the host organism thereby increasing the production of the heterogeously expressed proteins. This constitutes a further aspect of the invention.

The synthesis of a synthetic gene coding for *M. sedula* succinic semialdehyde reductase H39R N43H whose nucleotide sequence was optimized for the expression of said enzyme in *E. Coli* as represented by SEQ ID NO:228 is a further aspect of the invention.

In a still further aspect, the present invention also deals with nucleic acids, and more particularly with isolated nucleic acid sequences encoding a malate kinase as above described.

In another aspect, said nucleic acid is represented by SEQ ID NO: 13, SEQ ID NO:15, SEQ ID NO:17, SEQ ID NO:19, SEQ ID NO:21, SEQ ID NO:23, SEQ ID NO:25, SEQ ID NO:27, SEQ ID NO:38, SEQ ID NO:40, SEQ ID NO:42 or SEQ ID NO:44.

In a still further aspect, the present invention also deals with isolated nucleic acid sequences encoding a malate semialdehyde dehydrogenase as above described.

More specifically, said nucleic acid is preferentially represented by SEQ ID NO: 55, SEQ ID NO:57, SEQ ID NO:59, SEQ ID NO:61, SEQ ID NO:63, SEQ ID NO:65 or SEQ ID NO:67.

In a still further aspect, the present invention also deals with isolated nucleic acid sequences encoding a DHB dehydrogenase as above described.

In another aspect, said nucleic acid is represented by SEQ ID NO: 73 or SEQ ID NO: 75, SEQ ID NO: 224, SEQ ID NO: 226 or SEQ ID NO:82

In accordance with this invention, a "nucleic acid sequence" refers to a DNA or RNA molecule in single or double stranded form, preferably a DNA molecule. An "isolated DNA", as used herein, refers to a DNA which is not naturally-occurring or no longer in the natural environment wherein it was originally present, e.g., a DNA coding sequence associated with other regulatory elements in a chimeric gene, a DNA transferred into another host cell, or an artificial, synthetically-made DNA sequence having a different nucleotide sequence compared to any naturally-occurring DNA sequence.

The present invention also relates to a chimeric gene comprising, functionally linked to one another, at least one promoter which is functional in a host organism, a polynucleotide encoding anyone of the malate kinase, malate semialdehyde dehydrogenase or DHB dehydrogenase according to the invention, and a terminator element that is functional in the same host organism. The various elements which a chimeric gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art. The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, the promoters used for expression in bacteria may be chosen from the promoters mentioned below. For expression in *Escherichia coli* mention may be made of the lac, trp, lpp, phoA, recA, araBAD, prou, cst-I, tetA, cadA, nar, tac, trc, lpp-lac, Psyn, cspA, PL, PL-9G-50, PR-PL, T7, [lambda]PL-PT7, T3-lac, T5-lac, T4 gene 32, nprM-lac, VHb and the protein A promoters or else the Ptrp promoter (WO 99/64607). For expression in Gram-positive bacteria such as *Corynebacteria* or *Streptomyces*, mention may be made of the PtipA or PS1 and PS2 (FR91/09870) promoters or those described in application EP0629699A2. For expression in yeasts and fungi, mention may be made of the *K. lactis* PLAC4 promoters or the *K. lactis* Ppgk promoter (patent application FR 91/05294), the *Trichoderma* tef1 or cbh1 promoter (WO 94/04673), the *Penicillium* his, csl or apf promoter (WO 00/68401) and the *Aspergillus* gla promoter.

According to the invention, the chimeric gene may also comprise other regulatory sequences, which are located between the promoter and the coding sequence, such as transcription activators (enhancers).

As such, the chimeric gene of the invention comprises in a specific embodiment at least, in the direction of transcription, functionally linked, a promoter regulatory sequence which is functional in a host organism, a nucleic acid sequence encoding the malate kinase of the malate semialdehyde dehydrogenase of the invention and a terminator regulatory sequence which is functional in said host organism The present invention also relates to a cloning and/or expression vector comprising a chimeric gene according to the invention or a nucleic acid sequence of the invention. The vector according to the invention is of use for transforming a host organism and expressing in this organism anyone of the malate kinase, malate semialdehyde dehydrogenase and/or DHB dehydrognase. This vector may be a plasmid, a cosmid, a bacteriophage or a virus. Preferentially, the transformation vector according to the invention is a plasmid. Generally, the main qualities of this vector should be an ability to maintain itself and to self-replicate in the cells of the host organism, in particular by virtue of the presence of an origin of replication, and to express anyone of the malate kinase, malate semialdehyde dehydrogenase and/or DHB dehydrognase therein. For the purpose of stable transformation of a host organism, the vector may also integrate into the genome. The choice of such a vector, and also the techniques of insertion of the chimeric gene according to the invention into this vector and are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. According to a particular embodiment of the invention, the host organism to be transformed is a bacterium, a yeast, a fungus. Among the selectable markers which can be used, mention may be made of markers containing genes for resistance to antibiotics, such as, for example, the hygromycin phosphotransferase gene. Other markers may be genes to complement an auxotrophy, such as the pyrA, pyrB, pyrG, pyr4, arg4, argB and trpC genes, the molybdopterin synthase gene or that of acetamidase. Mention may also be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to transformed host organisms containing at least one chimeric gene according to the invention, either integrated into their genome or carried on an extrachromosomal genetic element, for example a plasmid. In a more specific aspect of the invention, the transformed host organism comprises a nucleic acid of the invention encoding a malate kinase or a chimeric gene comprising a nucleic acid encoding a malate kinase or an expression vector comprising a nucleic acid encoding a malate kinase, and/or a nucleic acid encoding a malate semialdehyde dehydrogenase, or a chimeric gene comprising a nucleic acid encoding a malate semialdehyde dehydrogenase or an expression vector comprising a nucleic acid encoding a malate semialdehyde dehydrogenase, and/or a nucleic acid encoding a DHB dehydrogenase, a chimeric gene comprising a nucleic acid encoding a DHB dehydrogenase or an expression vector comprising a nucleic acid encoding a DHB dehydrogenase.

In a specific aspect of the invention, the nucleic acid encoding the malate kinase is represented by SEQ ID NO: 13, SEQ ID NO:15, SEQ ID NO:17, SEQ ID NO:19, SEQ ID NO:21, SEQ ID NO:23, SEQ ID NO:25, SEQ ID NO:27, SEQ ID NO:38, SEQ ID NO:40, SEQ ID NO:42 or SEQ ID NO:44, the nucleic acid encoding the malate semialdehyde dehydrogenase is represented by SEQ ID 55, SEQ ID NO:57, SEQ ID NO:59, SEQ ID NO:61, SEQ ID NO:63, SEQ ID NO:65, or SEQ ID NO:67 and the nucleic acid encoding the DHB dehydrogenase is represented by SEQ ID NO: 73, SEQ ID NO:75, SEQ ID NO: 224, SEQ ID NO: 226 or SEQ ID NO: 82.

The term "host organism" is intended to mean any lower monocellular organism into which the chimeric gene(s), nucleic acid(s) or vector(s) according to the invention may be introduced in order to produce 2,4-DHB. Preferably, the host organism is a microorganism, in particular a fungus, for example of the *Penicillium, Aspergillus* and more particularly *Aspergillus flavus, Chrysosporium* or *Trichoderma* genus, a yeast, in particular of the *Saccharomyces, Kluyveromyces* or the *Pichia* genus and more particularly *Zygosaccharomyces rouxii*, a bacterium, for example of the *Escherichia* genus, in particular *E. coli*, or the *Corynebacterium* genus, more particularly *Corynebacterium glutamicum*, or of the *Streptomyces* genus or a baculovirus.

The host organism can be a host organism that naturally overproduces malate or succinate from sugars such as glucose or a host organism that was engineered to overproduce malate or succinate from sugars such as glucose and in which all potential membrane transporters that facilitate export of organic acids, such as malate, pyruvate, succinate, and fumarate have been deleted. The host organism can be an organism that was engineered to overproduce DHB and in which all membrane transporters that facilitate export of organic acids such as malate, pyruvate, succinate, and fumarate have been deleted. Examples of permeases that facilitate export of malate and other organic acids are Mae1 from *Schizosaccharomyces pombe* (Camarasa et al., 2001; Grobler et al., 1995), DctA from *Bacillus subtilis* (Groeneveld et al., 2010), Dct 1-4 from *E. Coli*, Jen1 from *S. cerevisiae* (Akita et al., 2000). For an expert it will be possible to identify candidate permeases in other microorganisms based on sequence homology. These constructions will serve to keep malate and other organic acids inside the cell to make them available for DHB production.

The expression "transformed host organism" is intended to mean a host organism which has incorporated into its genome, or in an extra chromosomal genetic element, for example a plasmid, at least one chimeric gene according to the invention, and consequently produces any one of malate kinase, malate semialdehyde dehydrogenase and/or DHB dehydrogenase in its tissues, or in a culture medium. To obtain the host organisms according to the invention, those skilled in the art may use one of the many known transformation methods.

One of these methods consists in bringing the cells of the host organisms to be transformed into contact with polyethylene glycol (PEG) and with the vectors according to the invention. Electroporation is another method, which consists in subjecting the cells to be transformed and the vectors of the invention to an electric field. Another method consists in directly injecting the vectors into the cells or the tissues by microinjection. The "biolistic" method may be used. It consists in bombarding cells or tissues with particles onto which the vectors of the invention are adsorbed (U.S. Pat. No. 4,945,050).

Several methods for transforming bacteria are described in the literature for *Escherichia coli* and other Gram-negative bacteria. Conjugation may also be used. For Gram-positive bacteria, electroporation may be used, and also protoplast transformation, in particular for bacteria of the *Streptomyces* genus.

Several methods for transforming fungi are also described in the literature. Protoplast transformation with PEG is described for *Aspergillus* in EP 0260762, and an adaptation of this method to the species *Penicillium funiculosum* is described in WO 00/36120. Transformation by restriction enzyme mediated integration, or REMI, is also known, as is protoplast transformation using bacteria of the *Agrobacterium* genus. Techniques for transforming yeasts are also described in the literature, In a further aspect, the invention deals with a process of production of 2,4-DHB comprising the step of cultivating a transformed microorganism of the invention.

For the production of DHB various carbohydrates could be utilized individually or as a mixture such as glucose, fructose, sucrose, molasses, maltose, blackstrap molasses, starch hydrolysate (glucose, oligosaccharides), lactose, maltose, starch and starch hydrolysates, cellulose, cellulose hydrolysate, glycerol and certainly hydrocarbons, oils and fats such as soy bean oil, sunflower oil, groundnut oil and coconut oil as well as fatty acids such as e.g. palmitic acid, stearic acid and linoleic acid. Those substances may be used individually or as mixtures.

Various sources of nitrogen could be utilized individually or as mixtures for the commercial and pilot scale production, including inorganic compounds such as gaseous and aqueous ammonia, ammonium salts of inorganic or organic acids such as ammonium sulphate, ammonium nitrate, ammonium phosphate, ammonium chloride, ammonium acetate and ammonium carbonate. Alternatively, natural nitrogen containing organic materials like soybean-hydrolysate, soy protein HCl-hydrolysate (total nitrogen of about 7%), soy bean meal, soybean cake hydrolysate, corn steep liquor, casein hydrolysate, yeast extract, meat extract, malt extract, urea, peptones and amino acids may also be utilized The production process can be carried out under aerobic, anaerobic, and oxygen limited conditions. It can be carried out as a fed-batch process or a batch process.

Said production of 2,4-DHB can be made by cultivating the host organism in media where malate (or another organic acid such as pyruvate, succinate, or fumarate) was added alone or together with another carbon source that ensures growth. Malate (and other organic acids) can be added either directly, or by designing a two-stage fermentation process where malate (or other organic acids) is produced in a first process stage by a malate-overproducing microorganism, and 2,4-DHB production is realised in the following stage by a host organism according to the invention.

Product separation and purification is very important factor enormously affecting overall process efficiency and product costs. Methods for product recovery commonly comprise the steps cell separation, as well as product purification, concentration and drying, respectively.

Cell Separation

Ultrafiltration and centrifugation can be used to separate cells from the fermentation medium. Cell separation from fermentation media is often complicated by high medium viscosity. Therefore, we can add additives such as mineral acid or alkali salts, or heating of the culture broth to optimize cell separation.

Product Recovery

A variety of ion-exchange chromatographic methods can be applied for the separation of DHB either before or after biomass removal. They include the use of primary cation exchange resins that facilitate separation of products according to their isoelectric point. Typically, the resin is charged with the solution, and retained product is eluted separately following increase of pH (eg by adding ammonium hydroxide) in the eluent. Another possibility represents the use of ion-exchange chromatography using fixed or simulated moving bed resins. Different chromatographic steps may have to be combined in order to attain adequate product purity. Those purification methods are more economical compared with a costly crystallization step, also providing additional advantages and flexibility regarding the form of final product.

Product Concentration and Drying

The purification process can also comprises a drying step which may involve any suitable drying means such as a spray granulator, spray dryer, drum dryer, rotary dryer, and tunnel dryer. Concentrated DHB solutions can be obtained by heating fermentation broths under reduced pressure by steam at 130° C. using a multipurpose concentrator or thin film evaporator.

Efficient production of DHB can be ensured by optimizing carbon flux repartitioning in the metabolic network of the host organism and by ensuring sufficient NADPH and ATP supply for the three enzymes of the DHB pathway. Channeling of carbon flux into a desired metabolic pathway and supply of NAD(P)H cofactor is commonly facilitated by deleting or alleviating competing natural fermentative pathways. Nonexclusive examples are the optimization of malate production in *S. cerevisiae* by impeding the formation of ethanol (by the deletion of pyruvate decarboxylases (Zelle et al., 2008; Zelle et al., 2010).

the optimization of succinate or malate production in *E. coli* by impeding the formation of lactate (e.g. deletion of ldhA), the formation of acetate (e.g. deletion of pta, ackA), the formation of ethanol (e.g. deletion of adhE), the formation of formate (e.g. deletion of pflB, focA), the oxidation of pyruvate (e.g. deletion of poxB), the degradation of malate (deletion of maeB and scfA), the formation of succinate (e.g. deletion of frdBC), the formation of methylglyoxal (deletion of mgsA) (Jantama et al., 2008a; Jantama et al., 2008b; Lin et al., 2005; Sanchez et al., 2005a; Zhang et al., 2011).

Another possibility to increase carbon flux and ATP supply for the production of organic acids is the engineering of the phosphoenolpyruvate (PEP)/pyruvate/oxaloacetate branch node (reviewed in (Sauer & Eikmanns, 2005)). Nonexclusive examples for metabolic engineering strategies that ensure the increase of carbon flux from phosphoenolpyruvate to oxaloacetate are the optimization of malate production in *S. cerevisiae* by impeding the function of pyruvate kinase and increasing the activity of PEP carboxykinase (Zelle et al., 2010).

the optimization of succinate production in *E. coli* by increasing the activity of natural or heterologously expressed PEP carboxylase, PEP carboxykinase, or pyruvate carboxylase (Millard et al., 1996; Sanchez et al., 2005b; Zhang et al., 2009).

Another possibility to increase carbon flux and ATP supply for the production of organic acids in *E. coli* and other bacteria employing the PEP-consuming phosphotransferase system (PTS) for the initial phosphorylation step of glucose is the deletion of essential components of the PTS system (for example ptsl or ptsG) (Lin et al., 2005; Zhang et al., 2009). To ensure further glucose uptake in mutants carrying deleterious mutations of the PTS system, the activity of alternative glucose uptake systems (e.g. GalP) has to be ensured.

Another possibility to increase carbon flux into the desired pathways for the production of organic acids is the engineering of the citric acid and glyoxylate cycle. Non-exclusive examples are:

the optimization of succinic acid production in *E. coli* by increasing the activity of isocitrate lyase (deletion of transcriptional repressor iciR) (Lin et al., 2005; Sanchez et al., 2005a).

the optimization of succinic acid production by the deletion of isocitrate dehydrogenase, and/or succinate dehydrogenase (Lin et al., 2005).

Another possibility to increase carbon flux into the desired pathways for the production of DHB is the expression of appropriate pyruvate dehydrogenases and citrate synthases in the production organism. Natural pyruvate dehydrogenase and citrate synthase of *E. coli* are inhibited by high intracellular NADH concentrations rendering these enzymes less active under anaerobic conditions. In *E coli*, the expression of a pyruvate dehydrogenase mutant that is insensitive to NADH resulted in the overproduction of acetyl-CoA under anaerobic conditions and modified carbon flux repartitioning between the fermentative end-products (acetate, lactate, ethanol, formate, and pyruvate) (Wang et al., 2010). The heterologous expression of the *Bacillus subtilis* citrate synthase which is insensitive to NADH increased succinic acid production in engineered *E. coli* strains (Sanchez et al., 2005a). In combination with the above described mutations, the use of the appropriate pyruvate dehydrogenases and citrate synthases (NADH sensitive or insensitive) enables the tuning of carbon flux repartitioning between glyoxylate and citric acid cycle reactions and fermentative pathways under anaerobic and aerobic conditions.

Another possibility to increase carbon flux through the DHB pathway is the deletion of enzymatic reactions that may degrade the pathway intermediates 4-phosphomalate, 4-malate semialdehyde. Candidate enzymes that may degrade malate semialdehyde are succinic semialdehyde dehydrogenases (sad, gabD), and other dehydrogenases that are able to oxidize C4 molecules with terminal aldehyde groups.

Another possibility to increase DHB productivity of the host organism is the deletion of metabolic reactions that degrade DHB. DHB is a competitive inhibitor of malic enzyme, thus, having comparatively high affinity for the active site of this enzyme (Rognstad & Katz, 1979). Therefore, DHB may be recognized by other enzymes and potentially degraded. These enzymes can be identified and deleted from the host organism.

When 2,4-DHB production is based on addition of malate or other organic acids, the 2,4-DHB-producing microorganisms should functionally express a membrane transport protein that facilitates uptake of malate (or other organic acids such as pyruvate, succinate, etc).

The following examples illustrate the invention. These examples are for purposes of illustration only and are not to be construed as limiting the scope of the invention in any manner.

BRIEF DESCRIPTION OF THE DRAWINGS

FIGS. 2A-2C: Alignment of amino acid sequences of aspartate kinases from different organisms. (Ec_AKIII—aspartate kinase III (SEQ ID NO: 4), LysC, of *E. coli*, Ec_AKI (SEQ ID NO: 87)—aspartate kinase I, ThrA, of *E. coli*, Ec_AKII (SEQ ID NO: 88—aspartate kinase II, MetL, of *E. coli*, Mj—*Methanococcus jannaschii* (SEQ ID NO: 89), Tt—*Thermus thermophilus* (SEQ ID NO: 90), Cg—*Corynebacterium glutamicum* (SEQ ID NO: 91), At—*Arabidopsis thaliana* (SEQ ID NO: 92), Sc—*Saccharomyces cerevisiae*. (SEQ ID NO: 93)) The figure was produced using ClustalW2 (Larkin et al., 2007).

FIG. 3: Alignment of amino acid sequences of aspartate semialdehyde dehydrogenases from different organisms. (Ec—*E. Coli* (SEQ ID NO: 49), Mj—*Methanococcus jannaschii* (SEQ ID NO: 94), Tt—*Thermus thermophilus* (SEQ ID NO: 95), Bs—*Bacillus subtilis* (SEQ ID NO: 96), Cg—*Corynebacterium glutamicum* (SEQ ID NO: 97), At—*Arabidopsis thaliana* (SEQ ID NO: 98), Sc—*Saccharomyces cerevisiae*. (SEQ ID NO: 99)) The figure was produced using ClustalW2 (Larkin et al., 2007).

EXAMPLES

Example 1

Figure 1:
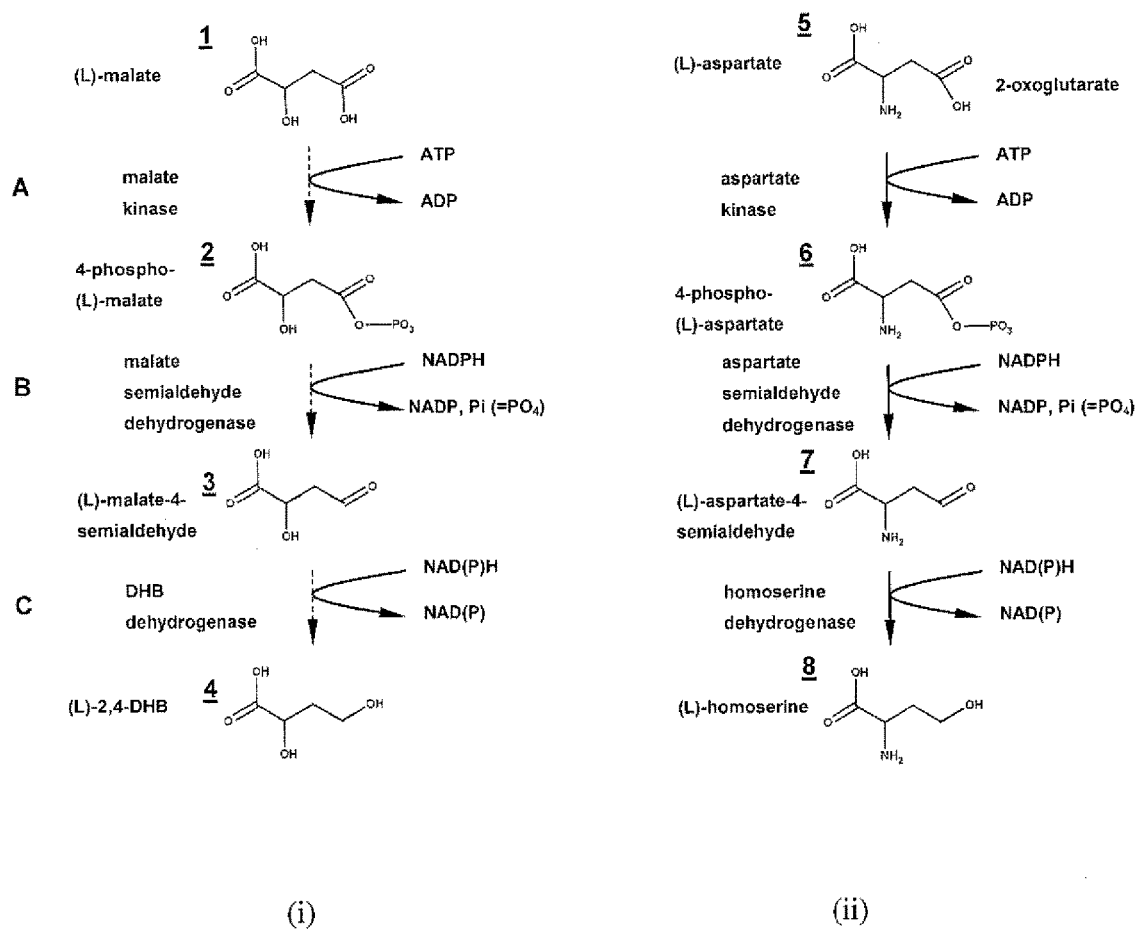
FIG. 1: (i) Reaction scheme that describes the conversion of (L)-malate into (L)-2,4-dihydroxybutyrate (DHB), and (ii) the analogy to the conversion of (L)-aspartate into (L)-homoserine.

Test of Aspartate Kinases LysC and Hom3 from *Escherichia coli* and *Saccharomyces cerevisiae*, Respectively, for Aspartate and Malate Kinase Activity Construction of plasmids containing wild-type genes of aspartate kinase: The plasmid pLYSCwt was constructed by amplifying the lysC gene by PCR using high fidelity polymerase Phusion™ (Finnzymes) and the direct and reverse primers $^{5'}$CACGAGGTACATATGTCTGAAATTGTTGTCTCC$^{3'}$ (SEQ ID NO: 1) and $^{5'}$CTTCCAGGGGATCCAGT-ATTTACTCAAAC$^{3'}$ (SEQ ID NO: 2) that introduce a NdeI and BamHI restriction sites upstream of the start codon and downstream of the stop codon, respectively. Genomic DNA from *E. coli* DH5a was used as the template. The PCR product was digested with NdeI and BamHI, ligated into the corresponding sites of the pET28a (Novagen) expression vector using T4 DNA ligase (Biolabs), and transformed into E. coli DH5α cells. The resulting pAKIIIwt plasmid was isolated and shown by DNA sequencing to contain the full-length lysC gene having the correct sequence (SEQ ID NO: 3). The corresponding protein is represented by SEQ ID NO: 4.

The plasmid pHOM3 wt was constructed by amplifying the HOM3 gene by PCR using high fidelity polymerase Phusion™ (Finnzymes) and the direct and reverse primers 5'ATAATGCTAGCATGCCAATGGATTTCCAACC3' (SEQ ID NO: 5) and 5'TATAATGAATTCT-TAAATTC-CAAGTCTTTTCAATTGTTC3' (SEQ ID NO: 6) that introduce a NheI and an EcoRI restriction sites upstream of the start codon and downstream of the stop codon, respectively. Genomic DNA from S. cerevisiae BY4741 wt was used as the template. The PCR product was digested with NheI and EcoRI, and ligated into the corresponding sites of the pET28a (Novagen) expression vector using T4 DNA ligase (Biolabs), and transformed into E. coli DH5α cells. The resulting pHOM3 wt plasmid was isolated and shown by DNA sequencing to contain the full-length HOM3 gene having the correct sequence (SEQ ID NO: 7). The corresponding protein is represented by SEQ ID NO: 8.

Expression of enzymes: E. coli BL21 D3 star cells were transformed with the appropriate plasmids. Enzymes with an N-terminal hexa-His tag were expressed in 250 mL LB cultures that were inoculated from an overnight culture at $OD_{600}$ of 0.1 and grown to $OD_{600}$ of 0.6 before protein expression was induced by addition of 1 mM isopropyl β-D-1-thiogalactopyranoside (IPTG) to the culture medium. After 3 h of protein expression, cells were harvested by centrifugation at 13000 g for 10 min and stored at −20° C. until further analysis. Growth and protein expression were carried out at 37° C. Culture media contained 50 μg/L kanamycin.

Purification of enzymes: Frozen cell pellets of expression cultures were resuspended in 0.5 mL of breakage buffer (50 mM Hepes, 300 mM NaCl, pH 7.5) and broken open by four successive rounds of sonication (Bioblock Scientific, Vibra-Cell™ 72437) with the power output set to 30%. Cell debris was removed by centrifuging the crude extracts for 15 min at 4° C. at 13000 g and retaining the clear supernatant. RNA and DNA were removed from the extracts by adding 15 mg/mL streptomycin (Sigma), centrifuging the samples at 13000 g for 10 min at 4° C. and retaining the supernatant. Clear protein extract was incubated for 1 h at 4° C. with 0.75 mL bed volumes of Talon™ Cobalt affinity resin (Clontech). The suspension was centrifuged at 700 g in a table top centrifuge and supernatant was removed. The resin was washed with 10 bed volumes of wash buffer (50 mM Hepes, 300 mM NaCl, 15 mM Imidazole, pH 7.5) before aspartate kinases were eluted with 0.5 mL of elution buffer (50 mM Hepes, 300 mM NaCl, 500 mM Imidazole, pH 7.5). Purity of eluted enzymes was verified by SDS-PAGE analysis.

Enzymatic assay: Aspartate or malate kinase activities were assayed by coupling ADP production in the kinase reactions to NADH oxidation in the presence of phosphoenolpyruvate, pyruvate kinase, and lactate dehydrogenase.
Reaction Scheme:
Aspartate (or Malate) Kinase

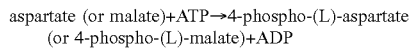
aspartate (or malate)+ATP→4-phospho-(L)-aspartate (or 4-phospho-(L)-malate)+ADP Pyruvate Kinase

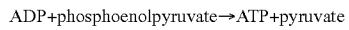
ADP+phosphoenolpyruvate→ATP+pyruvate

Lactate Dehydrogenase

pyruvate+NADH→NAD⁺+lactate

The assay mixture contained 50 mM Hepes (pH 7.5), 50 mM KCl, 5 mM $MgCl_2$, 0.24 mM NADH, 0.96 mM ATP, 0.96 mM PEP, 9 μg/mL of lactate dehydrogenase (Sigma, L2500), 12.4 μg/mL pyruvate kinase (Sigma, P1506), and appropriate amounts of purified aspartate (malate) kinase. Reactions were started by adding 50 mM (L)-aspartate or (L)-malate. Enzymatic assays were carried out at 30° C. in 96-well flat bottomed microtiter plates in a final volume of 250 μL. The reactions were followed by the characteristic absorption of NADH at 340 nm in a microplate reader (BioRad 680XR).

Hydroxamate assay: To verify phosphorylation of the substrate, i.e. formation of an acylphosphate anhydride, by wild-type or mutated aspartate kinases, the product of the kinase reaction was incubated with hydroxylamine to form the corresponding aspartate or malate hydroxamate derivative. The assay mixture contained 120 mM Hepes (pH 8), 200 mM KCl, 10 mM ATP, 200 mM hydroxylamine, 10 mM aspartate or malate, and appropriate amount of purified protein. The reaction was stopped after 30 min by addition of an equal volume of 1.7% (w/v) $FeCl_3$ in 1 M hydrochloric acid. Formation of the hydroxamate-iron complex was verified by measuring its characteristic absorbance at 540 nm in a microtiter plate reader. Assay mixtures containing all components except for ATP were used as a blank.

Results: Purified LysC (without His-tag, SEQ ID NO: 4) and Hom3 (without His-tag, SEQ ID NO:7) enzymes exhibited aspartate kinase activity but were not able to phosphorylate malate as verified by the hydroxamate assay (Keng & Viola, 1996). Maximum activities for LysC and Hom3 on aspartate were 4.5 μmol/(min*$mg_{prot}$) and 1.6 μmol/(min*$mg_{prot}$), respectively. The Km value for aspartate was estimated with the method of Eadie and Hofstee by measuring initial reaction rates (v) at different substrate concentrations (c) and by extracting the slope of the v versus v/c plot. The Km of purified His-tagged LysC was estimated around 0.6 mM showing that the His-tagged protein has the same substrate affinity as the non-tagged purified enzyme which was reported to be 0.6 mM (Marco-Marin et al., 2003).

Example 2

Site Directed Mutagenesis of Aspartate Kinase LysC from *Escherichia coli* and Test of Mutant Enzymes for Malate Kinase Activity Site-directed mutagenesis was carried out using the oligonucleotide pairs listed in Table 1 and the pLYSCwt (SEQ ID NO:3) plasmid as the template. Point mutations to change the amino acid sequence were introduced by PCR (Phusion 1 U, HF buffer 20% (v/v), dNTPs 2.5 mM, direct and reverse primers 1 μM each, template plasmid 200 ng, water) using the oligonucleotide pair listed in Table 1. Plasmids created by PCR contained a new restriction site for Nco1 (introduced using silent mutations) in addition to the functional mutation to facilitate identification of mutated clones. The PCR products were digested by DpnI at 37° C. for 1 h to remove template DNA, and transformed into NEB 5-alpha competent E. coli cells (NEB). The mutated plasmids were identified by restriction site analysis and verified to carry the desired mutations by DNA sequencing.

TABLE 1

Oligonucleotides used to mutate aspartate kinase lysC from *E. coli* in position E119.

| Mutation | Sequence 5'-3' |
|---|---|
| E119nnk | GCTGGTCAGCCATGGCNNNCTGATGTCGACCCTGC (SEQ ID NO: 10)<br>GCAGGGTCGACATCAGNNNGCCATGGCTGACCAGC (SEQ ID NO: 11) |

The sequence representing a mutation in position 119 can be represented by SEQ ID NO:9, wherein the residue in position 119 is X, X being anyone of the 19 naturally occurring amino acid (except glutamine).

Mutant enzymes were expressed, purified and tested for aspartate and malate kinase activity as described in Example 1. Results are summarized in Table 2.

TABLE 2

Characterization of mutant enzymes for malate kinase activities. Values correspond to the average from at least two independent experiments.

| Amino acid in position 119 (Corresponding SEQ ID NO:) | Vmax [μmol/(mg*min]] | Km [mM]] |
|---|---|---|
| C (SEQ ID NO:12) | 0.97 | 19.7 |
| G (SEQ ID NO:14) | 0.49 | 16.0 |
| N (SEQ ID NO:16) | 0.13 | 27.1 |
| P (SEQ ID NO: 18) | 0.71 | 19.0 |
| Q (SEQ ID NO:20) | 0.01 | 39.9 |
| S (SEQ ID NO:22) | 0.83 | 15.7 |
| T (SEQ ID NO:24) | 0.33 | 26.8 |
| V (SEQ ID NO:26) | 0.29 | 39.7 |

None of the mutants listed in Table 2 had activity on aspartate.

The results show that aspartate kinase can be transformed into malate kinase by replacing the conserved glutamate at position 119 by cysteine, glycine, asparagine, proline, glutamine, serine, threonine, or valine.

The corresponding nucleic acid sequences of the enzyme listed in Table 2 are SEQ ID NO:13, SEQ ID NO:15, SEQ ID NO:17, SEQ ID NO:19, SEQ ID NO:21, SEQ ID NO:23, SEQ ID NO:25 and SEQ ID NO:27.

Example 3

Construction of a Malate Kinase with Strongly Decreased Sensitivity for Inhibition by Lysine Site-directed mutagenesis was carried out using the oligonucleotide pairs listed in Table 3 and the pLYSC_E119G plasmid as the template (The pLYSC_E119G plasmid was obtained as described in Example 2 by introducing the following changes in the DNA sequence of the lysC gene: (SEQ ID NO: 15). Point mutations to change the amino acid sequences were introduced by PCR (Phusion 1U, HF buffer 20% (v/v), dNTPs 2.5 mM, direct and reverse primers 1 μM each, template plasmid 200 ng, water) using the oligonucleotide pairs listed in Table 1. When possible, plasmids created by PCR contained new restriction sites (introduced using silent mutations) in addition to the functional mutation to facilitate identification of mutated clones. The PCR products were digested by DpnI at 37° C. for 1 h to remove template DNA, and transformed into NEB 5-alpha competent *E. coli* cells (NEB). The mutated plasmids were identified by restriction site analysis and verified to carry the desired mutations by DNA sequencing.

TABLE 3

Oligonucleotides used to mutate malate kinase lysC E119G from *E. coli*.

| Mutation | Sequence 5'-3' |
|---|---|
| E250K | GCGTTTGCCGAAGCGGCAAAGATGGCCACTTTTG (SEQ ID NO: 28)<br>CAAAAGTGGCCATCTTTGCCGCTTCGGCAAACGC (SEQ ID NO: 29) |
| T344M | GGTAGATCTAATCACCATGTCAGAAGTGAGCGTGG (SEQ ID NO: 30)<br>CCACGCTCACTTCTGACATGGTGATTAGATCTACC (SEQ ID NO: 31) |
| S345L | GGTAGATCTAATCACCACGTTAGAAGTGAGCGTGGC (SEQ ID NO: 32)<br>GCCACGCTCACTTCTAACGTGGTGATTAGATCTACC (SEQ ID NO: 33) |
| T344M | GGTAGATCTAATCACCATGTCAGAAGTGAGCGTGG (SEQ ID NO: 34)<br>CCACGCTCACTTCTGACATGGTGATTAGATCTACC (SEQ ID NO: 35) |
| T352I | GTCAGAAGTGAGCGTGGCATTAATTCTAGATACCAC (SEQ ID NO: 36)<br>GTGGTATCTAGAATTAATGCCACGCTCACTTCTGAC (SEQ ID NO: 37) |

The nucleic acid sequence of the protein LysC E119G comprising an additional mutation corresponding to (i) the replacement of the glutamic acid in position 250 by a lysine is represented by SEQ ID NO: 38; its corresponding amino acid sequence is represented by SEQ ID NO: 39; (ii) the replacement of the threonine in position 344 by methionine is represented by SEQ ID NO: 40; its corresponding amino acid sequence is represented by SEQ ID NO: 41; (iii) the replacement of the threonine in position 352 by isoleucine is represented by SEQ ID NO: 42; its corresponding amino acid sequence is represented by SEQ ID NO: 43, (iv) the replacement of the serine in position 345 by leucine is represented by SEQ ID NO: 44; its corresponding amino acid sequence is represented by SEQ ID NO: 45.

Expression and purification of enzymes: Protein expression for the His-tagged enzymes LysC E119G, LysC E119G E250K, LysC E119G T344M, LysC E119G S345L, LysC E119G T352I was carried out as described in Example 1.

Enzymatic assay: Malate kinase activities were assayed as described in Example 1. Lysine concentration in the reaction buffer was varied.

Figure 4:
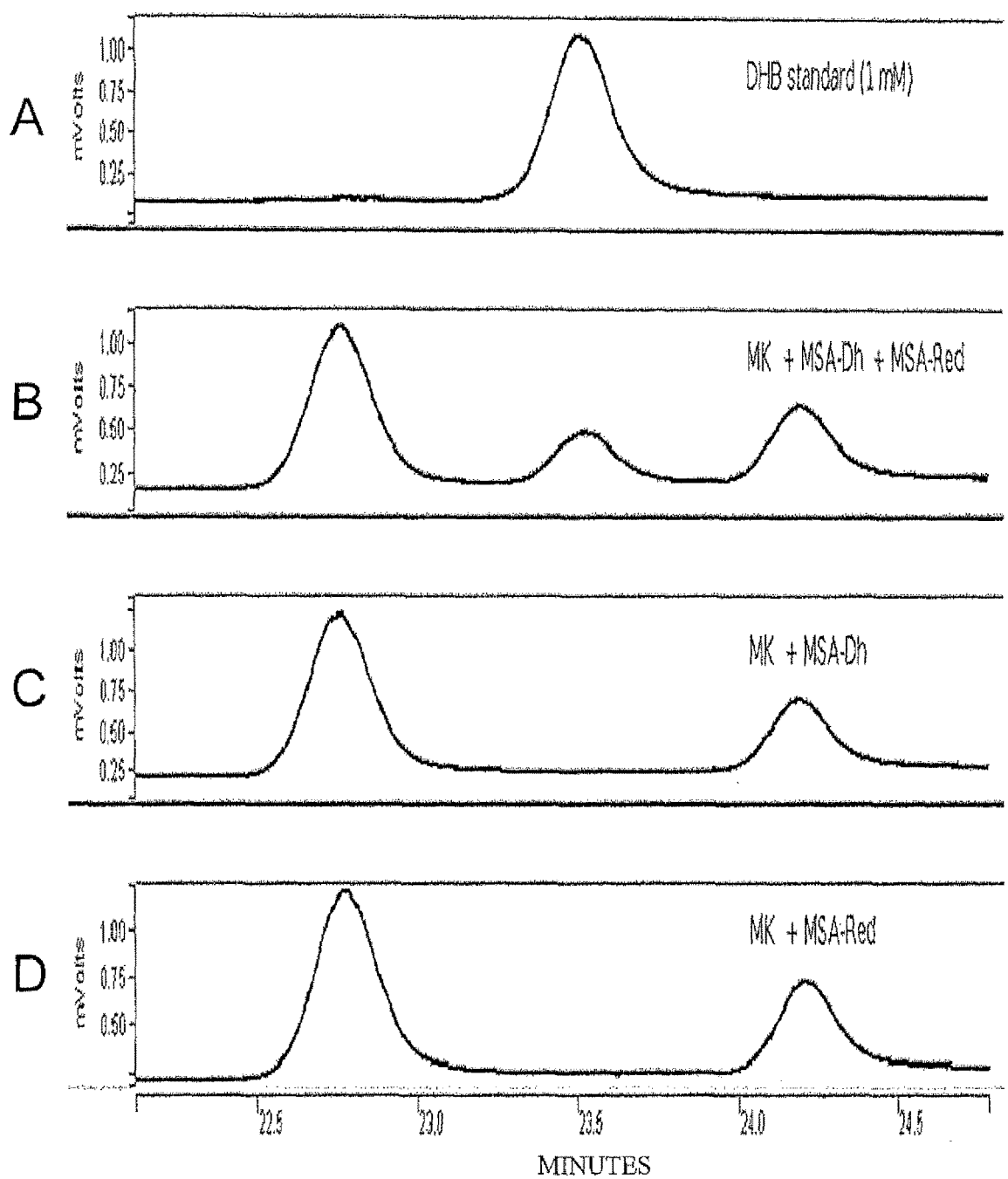
FIG. 4: GC chromatograms zooming on the region that corresponds to the retention time of DHB showing: (A) DHB standard (concentration=1 mM); (B) composition of Reaction A containing malate kinase (MK), malate semialdehyde dehydrogenase (MSA-Dh), and malate semialdehyde reductase (MSA-Red); (C) composition of control Reaction B (same as A but lacking MSA-Red); (D) composition of control Reaction C (same as A but lacking MSA-Dh).

Results: The introduction of mutations E250K, T344M or S345L into LysC E119G renders the malate kinase activity largely insensitive to elevated lysine concentrations (See FIG. 4).

Example 4

Test of Aspartate Semialdehyde Dehydrogenases Asd from *Escherichia coli* for Aspartate and Malate Semialdehyde Dehydrogenase Activity Construction of Plasmids Containing Wild-Type Genes of Aspartate Semialdehyde Dehydrogenase: The plasmid pAS-Dwt was constructed by amplifying the asd gene of *E. coli* by PCR using high fidelity polymerase Phusion™ (Finnzymes) and the direct and reverse primers 5'ATAAT-GCTAGCATGAAAAATGTTGGTTTTATCGG3' (SEQ ID NO: 46) and 5'ATAATGGATCCTTACGCCAGTTGAC- GAAGC3' (SEQ ID NO: 47) that introduce a NheI and BamHI restriction site upstream of the start codon and downstream of the stop codon, respectively. Genomic DNA from *E. coli* DH5α was used as the template. The PCR product was digested with NheI and BamHI, ligated into the corresponding sites of the pET28a (Novagen) expression vector using T4 DNA ligase (Biolabs), and transformed into *E. coli* DH5α cells. The resulting pASDwt plasmid was isolated and shown by DNA sequencing to contain the full-length asd gene having the correct sequence (SEQ ID NO: 48). The corresponding amino acid sequence of said enzyme is represented by SEQ ID NO: 49.

Expression and purification of enzymes: Protein expression for the His-tagged enzymes Asd was carried out as described in Example 1.

Enzymatic assay: Aspartate or malate semialdehyde dehydrogenase activities were assayed in the reverse biosynthetic direction by following the reduction of NADP during the oxidation of aspartate or malate semialdehyde to 4-phospho-(L)-aspartate or 4-phospho-(L)-malate, respectively (Roberts et al., 2003).

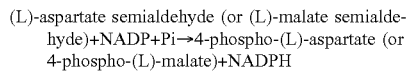

(L)-aspartate semialdehyde (or (L)-malate semialdehyde)+NADP+Pi→4-phospho-(L)-aspartate (or 4-phospho-(L)-malate)+NADPH The assay mixture contained 200 mM Hepes (pH 9), 50 mM $K_2HPO_4$, 0.25 mM NADP. Reactions were started by adding (L)-aspartate semialdehyde or (L)-malate semialdehyde. (L)-Aspartate semialdehyde was added in the form of L-aspartic acid β-semialdehyde hydrate trifluoroacetate (maintained at pH3 to prevent degradation) which is a suitable substrate for enzymatic tests of homoserine dehydrogenase and aspartate semialdehyde dehysrogenase (Roberts et al., 2003). Unstable malate semialdehyde was produced freshly prior to the enzymatic tests by the deprotection of the stable malate semialdehyde derivative 2-[(4S)-2,2-dimethyl-5-oxo-1,3-dioxolan-4-yl]acetaldehyde (DMODA). Malate semialdehyde was obtained by incubating DMODA in 2M hydrochloric acid for 15 min at 25° C., and evaporation of the released acetone (35° C., 50 mbar). The pH of the malate semialdehyde solution was fixed at 3 using sodium bicarbonate.

Enzymatic assays were carried out in 96-well flat bottomed microtiter plates in a final volume of 250 μL at 30° C. The reactions were followed by the characteristic absorption of NADPH at 340 nm in a microplate reader (BioRad 680XR).

Results: His-tagged wild-type aspartate semialdehyde dehydrogenase, Asd, oxidised (L)-aspartate semialdehyde to 4-phospho-(L)-aspartate with a maximum specific activity of 160 μmol/(min*$mg_{prot}$). On (L)-malate semialdehyde the enzyme had an activity of 0.01 μmol/(min*$mg_{prot}$).

Example 5

Site Directed Mutagenesis of Aspartate Semialdehyde Dehydrogenase Asd from *Escherichia coli* and Test of Mutant Enzymes for Malate Semialdehyde Dehydrogenase Activity Point mutations in the amino acid sequence of Asd were introduced using the pASDwt plasmid as the template and following the protocol outlined in Example 2. The oligonucleotide pairs listed in Table 4 were used to mutate the glutamate residue in position 241 or the threonine residue in position 136. The mutated plasmids were identified by restriction site analysis and verified to carry the desired mutations by DNA sequencing.

The Asd protein mutated in position 241 can be represented by SEQ ID NO: 68 wherein the residue in position 241 is X, X being anyone of the other 19 biologically occurring amino acid (except glutamine).

TABLE 4

Oligonucleotides used to mutate aspartate semialdehyde dehydrogenase Asd from *E. coli* in position E241 and T136.

| Mutation | Sequence 5'-3' |
|---|---|
| E241nnn | AGCTCGATAACGGTCAGAGTCGANNNGAGTGG AAAGGGCAGGCGG (SEQ ID NO: 50) CCGCCTGCCCTTTCCACTCNNNTCGACTCTGA CCGTTATCGAGCT (SEQ ID NO: 51) |
| T136N | TTTTGTTGGCGGTAACTGTAACGTGTCCCTGA TGTTG (SEQ ID NO: 52) CAACATCAGGGACACGTTACAGTTACCGCCAA CAAAA (SEQ ID NO: 53) |

Results: Activities and Km values of Asd mutated in position E241 are summarized in Table 5. Asd mutants where glutamate 241 was replaced by alanine, cysteine, glycine, histidine, isoleucine, methionine, or glutamine oxidised (L)-aspartate-4-semialdehyde to 4-phospho-(L)-aspartate with a significantly higher maximum specific activity than the wild-type enzyme. The double mutant Asd E241Q T136N (SEQ ID NO:231) had a maximum specific activity of 0.25 μmol/(min*$mg_{prot}$) and a Km of 0.25 mM.

TABLE 5

Characterization of mutant enzymes for malate semialdehyde dehydrogenase activities. Values correspond to the average from at least two independent experiments.

| Amino acid in position 241 (Corresponding SEQ ID NO:) | Vmax [μmol/(mg*min]] | Km* [mM] |
|---|---|---|
| A (SEQ ID NO:54) | 0.09 | 0.378 |
| C (SEQ ID NO:56) | 0.18 | 0.5 |
| E (= wt) (SEQ ID NO:49) | 0.01 | |
| G (SEQ ID NO:58) | 0.09 | 0.18 |
| H (SEQ ID NO:60) | 0.10 | 0.8 |
| I (SEQ ID NO:62) | 0.10 | 0.23 |
| M (SEQ ID NO:64) | 0.15 | 0.43 |
| Q (SEQ ID NO:66) | 0.39 | 0.52 |

*Km values were only estimated for selected mutants

The corresponding nucleic acids are represented by SEQ ID NO:55, SEQ ID NO:57, SEQ ID NO:48, SEQ ID NO:59, SEQ ID NO:61, SEQ ID NO:63, SEQ ID NO:65 and SEQ ID NO:67.

The double mutant Asd E241Q T136N has a nucleic acid sequence represented by SEQ ID NO: 230.

Example 6

Identification of a 2,4 DHB Dehydrogenase

To identify a suitable 2,4 DHB dehydrogenase, beta-hydroxyacid dehydrogenases from different biological sources were tested for their ability to reduce malate semialdehyde. Among the tested enzymes were the methylbutyraldehyde reductase, Ypr1 (Ford & Ellis, 2002))(SEQ ID NO: 73 and SEQ ID NO: 74), from *Saccharomyces cerevisiae*; and the succinic semialdehyde reductase, Ms-Ssr from

*Metallosphaera sedula* (Kockelkorn & Fuchs, 2009)(SEQ ID NO: 75 and SEQ ID NO: 76). The genes YPR1 and Ms-SSR were amplified using primers listed in Table 6 and cloned into vector pET28 (restriction enzymes see Table 3) yielding plasmids pYPR1 and pMs-SSR, respectively. The proteins were expressed and purified as described in Example 1.

TABLE 6

Primers and restriction enzymes used to clone candidate beta-hydroxyacid dehydrogenases

| Enzyme | Accession No | Primer 5'-3' | Restriction enzymes |
|---|---|---|---|
| Ms-SSR | GI:146304190 | TATAATGCTAGCATG AAAGCTGCAGTACTT CA (SEQ ID NO: 69) | NheI |
| | | TATAATGAATTCTTA CGGGATTATGAGACT TC (SEQ ID NO: 70) | EcoRI |
| YPR1 | GI:6320576 | TATAATGCTAGCATG CCTGCTACGTTAAAG AA (SEQ ID NO: 71) | NheI |
| | | TATAATGAGCTCTCA TTGGAAAATTGGGAA GG (SEQ ID NO: 72) | SacI |

Test for Malate Semialdehyde Reductase Activity:
Reaction:

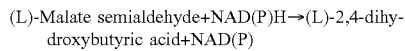

(L)-Malate semialdehyde+NAD(P)H→(L)-2,4-dihydroxybutyric acid+NAD(P)

The assay mixture contained 200 mM Hepes (pH 7.5), 50 mM KCl, 5 mM $MgCl_2$, 0.24 mM NADH or NADPH, and appropriate amounts of purified enzyme. Reactions were started by adding 10 mM (L)-malate semialdehyde (malate semialdehyde was prepared freshly for each test, see Example 4). Enzymatic assays were carried out at 30° C. in 96-well flat bottomed microtiter plates in a final volume of 250 μL. The reactions were followed by the characteristic absorption of NAD(P)H at 340 nm in a microplate reader (BioRad 680XR). Results are listed in Table 7.

TABLE 7

Reducing activity of selected beta-hydroxyacid dehydrogenases on malate semialdehyde (Results represent the average of at least two independent experiments).

| Enzyme | Origin | Reported function | Activity on malate semialdehyde (cofactor NADH) [μmol/(min*mg_prot)] | Activity on malate semialdehyde (cofactor NADPH) [μmol/(min*mg_prot)] |
|---|---|---|---|---|
| Ms-SSR (SEQ ID NO: 76) | *M. sedula* | Succinic semialdehyde reductase | 4.9 | 4.9 |
| YPR1 (SEQ ID NO: 74) | *S. cerevisiae* | Methyl-butyraldehyde reductase | nd | 0.19 |

The succinic semialdehyde dehydrogenase from *M. sedula* and the methylbutyraldehyde reductase from *S. cerevisiae* have malate semialdehyde reductase activity. The Km of Ms-SSR for malate semialdehyde was 1.1 mM.

Example 7

Site Directed Mutagenesis of Succinic Semialdehyde Reductase from *M. sedula*

Site-directed mutagenesis was carried out using the oligonucleotide pairs listed in Table 8 and the pMs-SSR plasmid as the template. Point mutations to change the amino acid sequences were introduced by PCR (Phusion 1U, HF buffer 20% (v/v), dNTPs 2.5 mM, direct and reverse primers 1 μM each, template plasmid 200 ng, water). When possible, plasmids created by PCR contained new restriction sites (introduced using silent mutations) in addition to the functional mutation to facilitate identification of mutated clones. The PCR products were digested by DpnI at 37° C. for 1 h to remove template DNA, and transformed into NEB 5-alpha competent *E. coli* cells (NEB). The mutated plasmids were identified by restriction site analysis and verified to carry the desired mutations by DNA sequencing. Table 9 summarizes kinetic parameters of the mutants. The results demonstrate that the double mutant Ms-SSR H39R N43H (SEQ ID NO: 81, SEQ ID NO: 82) has improved affinity for malate semialdehyde when compared to the wild type enzyme.

TABLE 8

Primer pairs used to mutate *M. sedula* succinic semialdehyde reductase (Ms-SSR)

| Mutation | Primer 5'-3' | Restriction enzymes |
|---|---|---|
| H39R | gtcaaggcaaccggtctctg tcgctccgacgtcaatg (SEQ ID NO: 77) cattgacgtcggagcgacag agaccggttgccttgac (SEQ ID NO: 78) | NheI |
| N43H | ggctctgtcactccgacgta catgtctttgaggggaaaac (SEQ ID NO: 79) gttttcccctcaaagacatg tacgtcggagtgacagagcc (SEQ ID NO: 80) | NheI |

TABLE 9

Summary of kinetic parameters of *M. sedula* succinic semialdehyde reductase (Ms-SSR) mutants (Results represent the average of at least two independent experiments).

| Mutant | Maximum activity [μmol/(min* $mg_{prot}$)] | Km [mmol/L] |
|---|---|---|
| Wild type ((SEQ ID NO: 76) | 4.9 | 1.1 |
| H39R (SEQ ID NO:225) | 1.7 | 0.5 |
| N43H (SEQ ID NO:227) | 4.3 | 2.5 |
| H39R N43H (SEQ ID NO: 81) | 4.7 | 0.4 |

The corresponding nucleic sequences are represented by SEQ ID NO: 224, SEQ ID NO: 226 and SEQ ID NO: 82.

Example 8

In vitro Production of DHB

The enzymes malate kinase (LysC E119G, SEQ ID NO: 15), malate semialdehyde dehydrogenase (Asd E241Q; SEQ ID NO: 67), and malate semialdehyde reductase (Ms SSrR, SEQ ID NO: 76) were expressed and purified as described in Example 1. Production of DHB was demonstrated in vitro by adding 50 mM malate to a reaction mixture that contained 50 mM Hepes (pH 7.5), 50 mM KCl, 5 mM MgCl$_2$, 1 mM NADPH, 180 µg/mL of malate kinase (Lys E119G), 325 µg/mL of malate semialdehyde dehydrogenase (Asd E241Q), and 130 µg/mL of malate semialdehyde reductase (Ms_Ssr) (Reaction A). Control reactions contained all components but were lacking either malate semialdehyde reductase (Reaction B) or malate semialdehyde dehydrogenase (Reaction C). After 30 min of incubation at 30° C., the reaction mixture was analysed by gas chromatography [CPG Varian Series 430; equipped with FID detector; autosampler CP8400; splitless injector 1177 (230° C.); column: CP-WAX58/FFAP, 30 m×0.53 mm, d$_f$ 0.50 µm; and liner: Inlet Sleeve, gooseneck 6.5×78.5×4 mm GWOL (Varian). Carrier gas was nitrogen at a flow rate of 25 mL/min. Flame ionization was carried out using an air-hydrogen mixture (flow rates were 300 mL/min and 30 mL/min, respectively). Detector temperature was 240° C. Injected sample volume was 1 µL. Temperature program is provided in Table 10.

TABLE 10

Temperature program for analysis of reaction mixtures

| Column temperature [° C.] | Hold [min] | Gradient [° C./min] | Runtime [min] |
|---|---|---|---|
| 90 | 0 | 0 | 0 |
| 115 | 1.8 | 30 | 2.63 |
| 160 | 2 | 2 | 27.13 |
| 230 | 1 | 50 | 29.53 |

Figure 5:
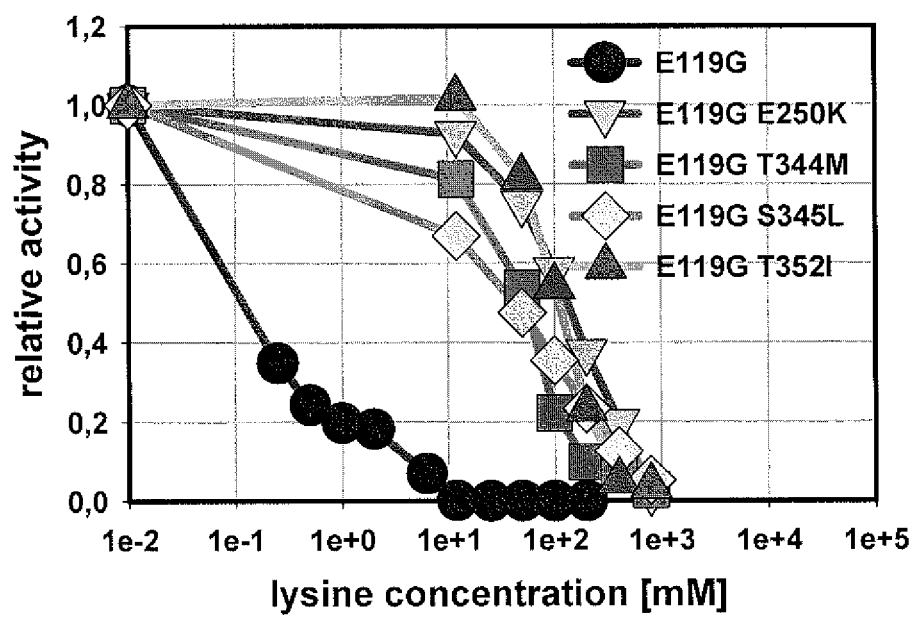
FIG. 5: Relative activities of purified LysC E119G, LysC E119G E250K, LysC E119G T344M, LysC E119G S345L, LysC E119G T344M, and LysC E119G T352I mutants with respect to lysine concentration in the reaction buffer.

DHB production was detected in reaction A (presence of all enzymes), but was absent in control reaction B and C (FIG. 5).

Example 9

Optimization of the Coding Sequence of *M. sedula* Succinic Semialdehyde Reductase for its Expression in *E. coli*

The coding sequence of *M. sedula* succinic semialdehyde reductase including the mutations H39R and N43H was optimized for maximum expression in *E. coli*, using the GeneOptimizer® software. The synthetic gene was produced by GeneArt® Gene Synthesis (Invitrogen Life Technologie). NheI and EcoRI restriction sites were introduced upstream of the start codon and downstream of the stop codon, respectively, allowing direct cloning into pET28a+ (Novagen).

The resulting pSSR-H39RN43H-opt plasmid was isolated and shown by DNA sequencing to contain the full-length *M sedula* SSR H39R N43H gene having the correct sequence (SEQ ID NO:228).

Example 10

Construction of a Plasmid that Facilitates the Simultaneous Expression of Malate Kinase (Mutant of the lysC Gene from *E. coli*), Malate Semialdehyde Dehydrogenase, (Mutant of the Asd Gene from *E. coli*), and DHB Dehydrogenase (Mutant of the *M. sedula* Succinic Semialdehyde Reductase Gene) Using *E. coli* as the Host Organism The plasmid pLYSC-E119G E250K (SEQ ID NO:38) was used as the backbone for the operon construction. A DNA fragment containing the pET28 (Novagen) ribosome binding site (rbs) and the coding region of ASD-E241Q was obtained by PCR (high fidelity polymerase Phusion™ (Finnzymes)) using pASD-E241Q (SEQ ID NO: 55 as the template, and the direct and reverse primers 5'ATAAGGATCCGTTTAACTTTAAGAAGGAGATATAC-CATGGG3' (SEQ ID NO: 83) and 5'ATAAGAATTCT-TACGCCAGTTGACGAAG3' (SEQ ID NO: 84) that introduced a BamHI and a EcoRI restriction site upstream of the rbs and downstream of the stop codon, respectively. The PCR products were digested with BamHI and EcoRI, ligated into the corresponding sites of pLYSC-E119G E250K, using T4 DNA ligase (Biolabs), and transformed into *E. coli* DH5α cells. The resulting pLYSC-E119G-E250K_ASD-E241Q plasmid was isolated and shown by DNA sequencing to have the correct sequence.

A DNA fragment containing the pET28 ribosome binding site (rbs) and the coding region of the codon-optimized Ms-SSR-H39RN43H-opt was obtained by PCR using pSSR-H39RN43H-opt as the template, and the direct and reverse primers 5'ATAAGCGGCCGCGTTTAACTT-TAAGAAGGAGATAT3' (SEQ ID NO:85) and 5'TATAAACTCGAGCTTACGGAATAATCAGG3' (SEQ ID NO: 86) that introduced a NotI and a PspXI restriction site upstream of the rbs and downstream of the stop codon, respectively. The PCR products were digested with NotI and PspXI, ligated into the corresponding sites of pLYSC-E119G-E250K_ASD-E241Q, using T4 DNA ligase (Biolabs), and transformed into *E. coli* DH5α cells. The resulting pET28-DHB plasmid (SEQ ID NO: 229) was isolated and shown by DNA sequencing to have the correct sequence.

The 5' upstream promoter region simultaneously regulating the expression of the three genes (ie T7 promoter in pET28-DHB) can be replaced with any other promoter, inducible or constitutive, by digesting pET28-DHB with SphI and XbaI and cloning another promoter region with suitable restriction sites. As an example for the use of an inducible promoter, the T7 promoter of the pET28-DHB backbone was replaced by the tac promoter whose characteristics allow for protein expression in the presence of glucose (de Boer et al., 1983). The tac promoter was obtained from plasmid pEXT20 (Dykxhoorn et al., 1996) by digesting the plasmid with SphI and XbaI. The DNA fragment containing the promoter was purified and cloned into the SphI/XbaI digested pET28-DHB plasmid. The resulting pTAC-DHB plasmid was isolated and shown by DNA sequencing to have the correct sequence.

TABLE 11

List of plasmid constructed in this study

| Plasmid | Regulation | Features |
|---|---|---|
| pET28-DHB | T7 | lysC-E119G-E250K, asd-E241Q, Ms_SSR-H39R-N43H codon optimized |

TABLE 11-continued

List of plasmid constructed in this study

| Plasmid | Regulation | Features |
|---|---|---|
| pTAC-DHB | tac | lysC-E119G-E250K, asd-E241Q, Ms_SSR-H39R-N43H codon optimized |

Example 11

Construction of E. coli Strains to Optimise Carbon Flux Repartitioning and NADPH-cofactor Supply for Fermentative DHB Production Several genes were disrupted in E. coli strain MG1655 in order to optimise carbon flux repartitioning and cofactor supply for DHB production. Gene deletions were carried out using the lambda red recombinase method according to Datsenko et al. (Datsenko & Wanner, 2000).

The deletion cassettes were prepared by PCR using high fidelity polymerase Phusion™ (Finnzymes), and the FRT-flanked kanamycin resistance gene (kan) of plasmid pKD4 as the template (Datsenko & Wanner, 2000). Sense primers contained sequences corresponding to the 5' end of each targeted gene (underlined) followed by 20 by corresponding to the FRT-kan-FRT cassette of pKD4. Anti-sense primers contained sequences corresponding to the 3' end region of each targeted gene (underlined) followed by 20 bp corresponding to the cassette. The primers are described in Table 12. PCR products were digested with DpnI and purified prior to transformation.

E. coli MG1655 strain was rendered electro-competent by growing the cells to an $OD_{600}$ of 0.6 in LB liquid medium at 37° C., concentrating the cells 100-fold and washing twice with ice-cold 10% glycerol. The cells were transformed with plasmid pKD46 (Datsenko & Wanner, 2000) by electroporation (2.5 kV, 200 Ω, 25 µF, in 2 mm gap cuvettes). Transformants were selected at 30° C. on ampicillin (100 µg/mL) LB solid medium.

Disruption cassettes were transformed into electro-competent E. coli strains harbouring the lambda Red recombinase-expressing plasmid pKD46. The cells were grown at 30° C. in liquid SOB medium containing ampicillin (100 µg/mL). The lambda red recombinase system was induced by adding 10 mM arabinose when $OD_{600}$ of the cultures reached 0.1. Cells were further grown to an $OD_{600}$ of 0.6 before they were harvested by centrifugation, washed twice with ice-cold 10% glycerol, and transformed with the disruption cassette by electroporation. After an overnight phenotypic expression at 30° C. in LB liquid medium, cells were plated on solid LB medium containing 25 µg/mL kanamycin. Transformants were selected after cultivation at 30° C.

The gene replacement was verified by colony PCR using Crimson Taq polymerase (NEB). A first reaction was carried out with the flanking locus-specific primers (see tables 13) to verify simultaneous loss of the parental fragment and gain of the new mutant specific fragment. Two additional reactions were done by using nearby locus-specific primers with the respective common test primer k1 rev, or k2 for (see Table 13) within the FRT-kanamycin resistance cassette (sense locus primer/k1 rev and k2 for/reverse locus primer).

The resistance gene (FRT-kan-FRT) was subsequently excised from the chromosome using the FLP recombinase-harbouring plasmid pCP20 (Cherepanov & Wackernagel, 1995) leaving a scar region containing one FRT site. pCP20 is an ampicillin and CmR plasmid that shows temperature-sensitive replication and thermal induction of FLP recombinase synthesis. Kanamycin resistant mutants were transformed with pCP20, and ampicillin-resistant transformants were selected at 30° C. Transformants were then grown on solid LB medium at 37° C. and tested for loss of all antibiotic resistances. Excision of the FRT-kanamycin cassette was analysed by colony PCR using crimson taq polymerase and the flanking locus-specific primers (Table 13). Multiple deletions were obtained by repeating the above described steps.

Strains carrying single or multiple deletions were rendered electro-competent as described above, transformed with the pTAC-DHB plasmid which allows for the IPTG-inducible expression of the DHB pathway enzymes (see Example 10), and selected on solid LB medium containing 50 µg/mL kanamycin.

The plasmid pACT3-pck harbouring the PEP carboxykinase encoding pck gene of E. coli was constructed by amplifying the pck coding sequence using genomic DNA from E. coli MG1655 as the template and the forward and reverse primers, respectively, 5'ATAATCCCGGGATGCGCGTTAACAATGGTTTGACC3' (SEQ ID NO: 100) and 5'ATAATTCTAGATTACAGTTTCGGACCAGCCG3' (SEQ ID NO: 101). The DNA fragment was digested with XmaI and XbaI, ligated into the corresponding sites of the pACT3 expression vector (Dykxhoorn et al., 1996) using T4 DNA ligase (Biolabs), and transformed into E. coli DH5α cells. The transformants were selected on solid LB medium containing chloramphenicol (25 µg/mL). The resulting plasmid was isolated and correct insertion of the pck gene was verified by sequencing. Plasmids pACT3-aceA, pACT3-ppc, pACT3-galP, pACT3-pykA and pACT3-pyc harbouring, respectively, aceA, ppc, galP, or pykA (all E. coli) or pycA from Lactococcus lactis were constructed analogously using the primers listed in Table 14.

The above mentioned pACT3-derived plasmids and the pTAC-DHB plasmid were transformed into E. coli MG1655 mutants carrying combinations of the deletions listed in Table 12. Transformants containing both plasmids were selected on solid LB medium containing chloramphenicol (25 µg/mL) and kanamycin (50 µg/mL). Examples for constructed strains are listed in Table 15.

TABLE 12

Primers used for gene disruptions. Sequences homologous to target genes are underlined.

| Gene | Primer | Sequence |
|---|---|---|
| ldhA | Δ_ldhA_for | Gaaggttgcgcctaca ctaagcatagttgttg atgagtgtaggctgga gctgcttc (SEQ ID NO: 102) |
|  | Δ_ldhA_rev | Ttaaaccagttcgttc gggcaggtttcgcctt tttcatgggaattagc catggtcc (SEQ ID NO: 103) |
| adhE | Δ_adhE_for | Atggctgttactaatg tcgctgaacttaacgc actcgtagagcgtgtg taggctggagctgctt c (SEQ ID NO: 104) |

TABLE 12-continued

Primers used for gene disruptions.
Sequences homologous to target genes are underlined.

| Gene | Primer | Sequence |
|---|---|---|
|  | Δ_adhE_rev | Ttaagcggattttttc gcttttttctcagctt tagccggagcagccat atgaatatcctcctta g (SEQ ID NO: 105) |
| ackA | Δ_ackA_for | atgtcgagtaagttag tactggttctgaactg cggtagttcttcagtg taggctggagctgctt c (SEQ ID NO: 106) |
|  | Δ_ackA_rev | tcaagcagtcaggcgg ctcgcatcttgcgcga taaccagttcttccat atgaatatcctcctta g (SEQ ID NO: 107) |
| focA-pflB | Δ_focA-pflB_for | ttactccgtatttgca taaaaaccatgcgagt tacgggcctataagtg taggctggagctgctt c (SEQ ID NO: 108) |
|  | Δ_focA-pflB_rev | atagattgagtgaagg tacgagtaataacgtc ctgctgctgttctcat atgaatatcctcctta g (SEQ ID NO: 109) |
| pta | Δ_pta_for | gtgtcccgtattatta tgctgatccctaccgg aaccagcgtcggtgtg taggctggagctgctt c (SEQ ID NO: 110) |
|  | Δ_pta_rev | ttactgctgctgtgca gactgaatcgcagtca gcgcgatggtgtacat atgaatatcctcctta g (SEQ ID NO: 111) |
| poxB | Δ_poxB_for | atgaaacaaacggttg cagcttatatcgccaa aacactcgaatcggtg taggctggagctgctt c (SEQ ID NO: 112) |
|  | Δ_poxB_rev | ttaccttagccagttt gttttcgccagttcga tcacttcatcacccat atgaatatcctcctta g (SEQ ID NO: 113) |
| sad | Δ_sad_for | atgaccattactccgg caactcatgcaatttc gataaatcctgccgtg taggctggagctgctt c (SEQ ID NO: 114) |
|  | Δ_sad_rev | tcagatccggtctttc cacaccgtctggatat tacagaattcgtgcat atgaatatcctcctta g (SEQ ID NO: 115) |
| gabD | Δ_gabD_for | atgaaacttaacgaca gtaacttattccgcca gcaggcgttgattgtg taggctggagctgctt c (SEQ ID NO: 116) |
|  | Δ_gabD_rev | ttaaagaccgatgcac atatatttgatttcta agtaatcttcgatcat atgaatatcctcctta g (SEQ ID NO: 117) |
| gadA | Δ_gadA_for | atggaccagaagctgt taacggatttccgctc agaactactcgatgtg taggctggagctgctt c (SEQ ID NO: 118) |
|  | Δ_gadA_rev | tcaggtgtgtttaaag ctgttctgctgggcaa taccctgcagtttcat atgaatatcctcctta g (SEQ ID NO: 119) |
| gadB | Δ_gadB_for | atggataagaagcaag taacggatttaaggtc ggaactactcgatgtg taggctggagctgctt c (SEQ ID NO: 120) |
|  | Δ_gadB_rev | tcaggtatgtttaaag ctgttctgttgggcaa taccctgcagtttcat atgaatatcctcctta g (SEQ ID NO: 121) |
| gadC | Δ_gadC_for | atgctacatcagtac agacaggtaaagctaa gcagctcacattagtg taggctggagctgctt c (SEQ ID NO: 122) |
|  | Δ_gadC_rev | ttagtgtttcttgtca ttcatcacaatatagt gtggtgaacgtgccat atgaatatcctcctta g (SEQ ID NO: 123) |
| sfcA | Δ_sfcA_for | atggaaccaaaaacaa aaaaacagcgttcgct ttatatcccttacgtg taggctggagctgctt c (SEQ ID NO: 124) |
|  | Δ_sfcA_rev | ttagatggaggtacgg cggtagtcgcggtatt cggcttgccagaacat atgaatatcctcctta g (SEQ ID NO: 125) |
| maeB | Δ_maeB_for | atggatgaccagttaa aacaaagtgcacttga tttccataaatttgta taggctggagctgctt c (SEQ ID NO: 126) |
|  | Δ_maeB_rev | ttacagcggttgggtt tgcgcttctaccacgg ccagcgccaccatcat |

TABLE 12-continued

Primers used for gene disruptions. Sequences homologous to target genes are underlined.

| Gene | Primer | Sequence |
|---|---|---|
| ppc | Δ_ppc_for | atgaatatcctcctta g (SEQ ID NO: 127) atgaacgaacaatatt ccgcattgcgtagtaa tgtcagtatgctcgtg taggctggagctgctt c (SEQ ID NO: 128) |
| | Δ_ppc_rev | ttagccggtattacgc atacctgccgcaatcc cggcaatagtgaccat atgaatatcctcctta g (SEQ ID NO: 129) |
| pykA | Δ_pykA_for | atgtccagaaggcttc gcagaacaaaaatcgt taccacgttaggcgtg taggctggagctgctt c (SEQ ID NO: 130) |
| | Δ_pykA_rev | ttactctaccgttaaa atacgcgtggtattag tagaacccacggtcat atgaatatcctcctta g (SEQ ID NO: 131) |
| pykF | Δ_pykF_for | atgaaaaagaccaaaa ttgttttgcaccatcgg accgaaaaccgaagtg taggctggagctgctt c (SEQ ID NO: 132) |
| | Δ_pykF_rev | ttacaggacgtgaaca gatgcggtgttagtag tgccgctcggtaccat atgaatatcctcctta g (SEQ ID NO: 133) |
| mgsA | Δ_mgsA_for | atggaactgacgactc gcactttacctgcgcg gaaacatattgcggtg taggctggagctgctt c (SEQ ID NO: 134) |
| | Δ_mgsA_rev | ttacttcagacggtcc gcgagataacgctgat aatcggggatcagcat atgaatatcctcctta g (SEQ ID NO: 135) |
| iclR | Δ_iclR_for | atggtcgcaccccattc ccgcgaaacgcggcag aaaacccgccgttgtg taggctggagctactt c (SEQ ID NO: 136) |
| | Δ_iclR_rev | tcagcgcattccaccg tacgccagcgtcactt ccttcgccgctttcat atgaatatcctcctta g (SEQ ID NO: 137) |
| icd | Δ_icd_for | atggaaagtaaagtag ttgttccggcacaagg caagaagatcaccgtg |

TABLE 12-continued

Primers used for gene disruptions. Sequences homologous to target genes are underlined.

| Gene | Primer | Sequence |
|---|---|---|
| | | taggctggagctgctt c (SEQ ID NO: 138) |
| | Δ_icd_rev | ttacatgttttcgatg atcgcgtcaccaaact ctgaacatttcagcat atgaatatcctcctta g (SEQ ID NO: 139) |
| sucA | Δ_sucA_for | atgcagaacagcgctt tgaaagcctggttgga ctcttcttacctcgtg taggctggagctgctt c (SEQ ID NO: 140) |
| | Δ_sucA_rev | ttattcgacgttcagc gcgtcattaaccagat cttgttgctgtttcat atgaatatcctcctta g (SEQ ID NO: 141) |
| sucB | Δ_sucB_for | atgagtagcgtagata ttctggtccctgacct gcctgaatccgtagtg taggctggagctgctt c (SEQ ID NO: 142) |
| | Δ_sucB_rev | ctacacgtccagcagc agacgcgtcggatctt ccagcaactcttttcat atgaatatcctcctta g (SEQ ID NO: 143) |
| frdA | Δ_frdA_for | gtgcaaacctttcaag ccgatcttgccattgt aggcgccggtggcgtg taggctggagctgctt c (SEQ ID NO: 144) |
| | Δ_frdA_rev | tcagccattcgccttc tccttcttattggctg cttccgccttatccat atgaatatcctcctta g (SEQ ID NO: 145) |
| frdB | Δ_frdB_for | atggctgagatgaaaa acctgaaaattgaggt ggtgcgctataacgtg taggctggagctgctt c (SEQ ID NO: 146) |
| | Δ_frdB_rev | ttagcgtgatttcaaa atcgcaataagaaagt ctttcgaacttttcat atgaatatcctcctta g (SEQ ID NO: 147) |
| frdC | Δ_frdC_for | atgacgactaaacgta aaccgtatgtacggcc aatgacgtccaccgtg taggctggagctgctt c (SEQ ID NO: 148) |
| | Δ_frdC_rev | ttaccagtacagggca acaaacaggattacga tggtggcaaccaccat atgaatatcctcctta g (SEQ ID NO: 149) |

TABLE 12-continued

Primers used for gene disruptions. Sequences homologous to target genes are underlined.

| Gene | Primer | Sequence |
|---|---|---|
| frdD | Δ_frdD_for | atgattaatccaaatccaaagcgttctgacgaaccggtattctgggtgtaggctggagctgcttc (SEQ ID NO: 150) |
|  | Δ_frdD_rev | ttagattgtaacgacaccaatcagcgtgacaactgtcaggatagccatatgaatatcctccttag (SEQ ID NO: 151) |
| ptsG | Δ_ptsG_for | atgtttaagaatgcatttgctaacctgcaaaaggtcggtaaatcggtgtaggctggagctgcttc (SEQ ID NO: 152) |
|  | Δ_ptsG_rev | ttagtggttacggatgtactcatccatctcggttttcaggttatccatatgaatatcctccttag (SEQ ID NO: 153) |
| ptsI | Δ_ptsI_for | atgatttcaggcatttagcatccccgggtatcgctttcggtaaagtgtaggctggagctgcttc (SEQ ID NO: 154) |
|  | Δ_ptsI_rev | ttagcaaattattttttcttcaatgaacttgttaaccaacgtcatcatatgaatatcctccttag (SEQ ID NO: 155) |

TABLE 13

Primer pairs used for verification of gene disruptions

| Deleted gene | Forward primer | Reverse primer |
|---|---|---|
| K2 for/ k1 rev | cggtgccctgaatgaactgc (SEQ ID NO: 156) | cagtcatagccgaatagcct (SEQ ID NO: 157) |
| IdhA | atacgtgtcccgagcggtag (SEQ ID NO: 158) | tacacatcccgccatcagca (SEQ ID NO: 159) |
| adhE | gaagtaaacgggaaaatcaa (SEQ ID NO: 160) | agaagtggcataagaaaacg (SEQ ID NO: 161) |
| ackA | ccattggctgaaaattacgc (SEQ ID NO: 162) | gttccattgcacggatcacg (SEQ ID NO: 163) |
| focA_ pflB | atgccgtagaagccgccagt (SEQ ID NO: 164) | tgttggtgcgcagctcgaag (SEQ ID NO: 165) |
| pta | gcaaatctggtttcatcaac (SEQ ID NO: 166) | tcccttgcacaaaacaaagt (SEQ ID NO: 167) |
| poxB | ggatttggttctcgcataat (SEQ ID NO: 168) | agcattaacggtagggtcgt (SEQ ID NO: 169) |
| sad | gctgattctcgcgaataaac (SEQ ID NO: 170) | aaaaacgttcttgcgcgtct (SEQ ID NO: 171) |
| gabD | tctgtttgtcaccaccccgc (SEQ ID NO: 172) | aagccagcacctggaagcag (SEQ ID NO: 173) |
| gadA | aagagctgccgcaggaggat (SEQ ID NO: 174) | gccgccctcttaagtcaaat (SEQ ID NO: 175) |
| gadB | ggattttagcaatattcgct (SEQ ID NO: 176) | cctaatagcaggaagaagac (SEQ ID NO: 177) |
| gadC | gctgaactgttgctggaaga (SEQ ID NO: 178) | ggcgtgcttttacaactaca (SEQ ID NO: 179) |
| sfcA | tagtaaataacccaaccggc (SEQ ID NO: 180) | tcagtgagcgcagtgtttta (SEQ ID NO: 181) |
| maeB | attaatggtgagagtttgga (SEQ ID NO: 182) | tgctttttttttattattcgc (SEQ ID NO: 183) |
| ppc | gctttataaaagacgacgaa (SEQ ID NO: 184) | gtaacgacaattccttaagg (SEQ ID NO: 185) |
| pykA | tttatatgcccatggtttct (SEQ ID NO: 186) | atctgttagaggcggatgat (SEQ ID NO: 187) |
| pykF | ctggaacgttaaatctttga (SEQ ID NO: 188) | ccagtttagtagctttcatt (SEQ ID NO: 189) |
| iclR | gatttgttcaacattaactcatcgg (SEQ ID NO: 190) | tgcgattaacagacacccttt (SEQ ID NO: 191) |
| mgsA | tctcaggtgctcacagaaca (SEQ ID NO: 192) | tatggaagaggcgctactgc (SEQ ID NO: 193) |
| icd | cgacctgctgcataaacacc (SEQ ID NO: 194) | tgaacgctaaggtgattgca (SEQ ID NO: 195) |
| sucA | acgtagacaagagctcgcaa (SEQ ID NO: 196) | catcacgtacgactgcgtcg (SEQ ID NO: 197) |
| sucB | tgcaactttgtgctgagcaa (SEQ ID NO: 198) | tatcgcttccgggcattgtc (SEQ ID NO: 199) |
| frdA | aaatcgatctcgtcaaatttcagac (SEQ ID NO: 200) | aggaaccacaaatcgccata (SEQ ID NO: 201) |
| frdB | gacgtgaagattactacgct (SEQ ID NO: 202) | agttcaatgctgaaccacac (SEQ ID NO: 203) |
| frdC | tagccgcgaccacggtaagaaggag (SEQ ID NO: 204) | cagcgcatcacccggaaaca (SEQ ID NO: 205) |
| frdD | atcgtgatcattaacctgat (SEQ ID NO: 206) | ttaccctgataaattaccgc (SEQ ID NO: 207) |
| ptsG | ccatccgttgaatgagtttt (SEQ ID NO: 208) | tggtgttaactggcaaaatc (SEQ ID NO: 209) |
| ptsI | gtgacttccaacggcaaaag (SEQ ID NO: 210) | ccgttggtttgatagcaata (SEQ ID NO: 211) |

TABLE 14

Primers used for gene overexpression. Restriction sites used for cloning into pACT3 are underlined.

| Gene | Primer | Linker | Sequence |
|---|---|---|---|
| Ec_pck | Ec_pck_clon_for | XmaI | tataatcccgggatgcgcgttaacaatggtttgacc (SEQ ID NO: 212) |
| | Ec_pck_clon_rev | XbaI | tataattctagattacagtttcggaccagccg (SEQ ID NO: 213) |
| Ec_ppc | Ec_ppc_clon_for | XmaI | tataatcccgggatgaacgaacaatattcc (SEQ ID NO: 214) |
| | Ec_ppc_clon_rev | XbaI | tataattctagattagccggtattacgcat (SEQ ID NO: 215) |
| Ec_pykA | Ec_pykA_clon_for | XmaI | tataatcccgggatgtccagaaggcttcgcagaaca (SEQ ID NO: 216) |
| | Ec_pykA_clon_rev | XbaI | tataattctagattactctaccgttaaaatac (SEQ ID NO: 217) |
| Ec_aceA | Ec_aceA_clon_for | XmaI | tataatcccgggatgaaacccgtacacaacaaatt (SEQ ID NO: 218) |
| | Ec_aceA_clon_rev | XbaI | tataattctagattagaactgcgattcttcag (SEQ ID NO: 219) |
| Ll_pycA | Ll_pycA_clon_for | XmaI | tataatcccgggatgaaaaaactactcgtcgccaat (SEQ ID NO: 220) |
| | Ll_pycA_clon_rev | XbaI | tataattctagattaattaatttcgattaaca (SEQ ID NO: 221) |
| Ec_galP | Ec_galP_clon_for | XmaI | tataatcccgggatgcctgacgctaaaaaacagggcggt (SEQ ID NO: 222) |
| | Ec_galP_clon_rev | XbaI | tataattctagattaatcgtgagcgcctatttc (SEQ ID NO: 223) |

TABLE 15

Examples of strains constructed for DHB production

| Strain | Relevant genotype |
|---|---|
| MG1655 | Wild-type |
| ECE1 | pTAC-DHB |
| ECE5 | ΔldhA ΔadhE Δpta-ack pTAC-DHB |
| ECE6 | ΔldhA ΔadhE Δpta-ack pTAC-DHB pACT3-pck |
| ECE7 | ΔldhA ΔadhE Δpta-ack pTAC-DHB pACT3-ppc |
| ECE8 | ΔldhA ΔadhE Δpta-ack pTAC-DHB pACT3-pyc |
| ECE10 | ΔldhA ΔadhE Δpta-ack ΔpoxB pTAC-DHB |
| ECE11 | ΔldhA ΔadhE Δpta-ack ΔpoxB pTAC-DHB pACT3-pck |
| ECE12 | ΔldhA ΔadhE Δpta-ack ΔpoxB pTAC-DHB pACT3-ppc |
| ECE13 | ΔldhA ΔadhE Δpta-ack ΔpoxB pTAC-DHB pACT3-pyc |
| ECE16 | ΔldhA ΔadhE Δpta-ack ΔpoxB Δmae1 ΔsfcA pTAC-DHB pACT3-pck |
| ECE17 | ΔldhA ΔadhE Δpta-ack ΔpoxB Δmae1 ΔsfcA pTAC-DHB pACT3-ppc |
| ECE18 | ΔldhA ΔadhE Δpta-ack ΔpoxB Δmae1 ΔsfcA pTAC-DHB pACT3-pyc |
| ECE21 | ΔldhA ΔadhE Δpta-ack ΔpoxB Δmae1 ΔsfcA ΔfrdBC pTAC-DHB pACT3-pck |
| ECE22 | ΔldhA ΔadhE Δpta-ack ΔpoxB Δmae1 ΔsfcA ΔfrdBC pTAC-DHB pACT3-ppc |
| ECE23 | ΔldhA ΔadhE Δpta-ack ΔpoxB Δmae1 ΔsfcA ΔfrdBC pTAC-DHB pACT3-pyc |
| ECE30 | ΔldhA ΔadhE Δpta-ack ΔpoxB Δmae1 ΔsfcA ΔfrdBC ΔptsG pTAC-DHB pACT3-pck |
| ECE31 | ΔldhA ΔadhE Δpta-ack ΔpoxB Δmae1 ΔsfcA ΔfrdBC ΔptsG pTAC-DHB pACT3-ppc |
| ECE32 | ΔldhA ΔadhE Δpta-ack ΔpoxB Δmae1 ΔsfcA ΔfrdBC ΔptsG pTAC-DHB pACT3-pyc |

Example 12

Production of 2,4-dihydroxybutyric Acid by Fermentation of Glucose

Strains and cultivation conditions: Experiments were carried out with strain *E. coli* ECE1 co-expressing malate kinase, malate semialdehyde dehydrogenase and DHB dehydrogenase from the plasmid pTAC-DHB (see Example 11), and an isogenic control strain containing only the empty plasmid (i.e. the pTAC backbone without the coding sequences of the above mentioned enzymes). 1 Liter culture medium contained, 20 g glucose, 18 g $Na_2HPO_4*12\ H_2O$, 3 g $KH_2PO_4$, 0.5 g NaCl, 2 g $NH_4Cl$, 0.5 g $MgSO_4*7\ H_2O$, 0.015 $CaCl_2*2\ H_2O$, 1 mL of 0.06 mol/L $FeCl_3$ stock solution prepared in 100 times diluted concentrated HCl, 2 mL of 10 mM thiamine HCl stock solution, 20 g MOPS, 50 µg kanamycin sulphate, and 1 mL of trace element solution (containing per liter: 0.04 g $Na_2EDTA*2H_2O$, 0.18 g $CoCl_2*6\ H_2O$, $ZnSO4*7\ H_2O$, 0.04 g $Na_2MoO4*2\ H_2O$, 0.01 g $H_3BO_3$, 0.12 g $MnSO_4*H_2O$, 0.12 g $CuCl_2*H2O$.). pH was adjusted to 7 and medium was filter sterilized. All cultivations were carried out at 37° C. on an Infors rotary shaker running at 170 rpm. Overnight cultures (3 mL medium in test tube) were inoculated from glycerol stocks and used to adjust an initial $OD_{600}$ of 0.05 in 100 mL growth cultures cultivated in 500 mL shake flasks. IPTG was added at a concentration of 1 mmol/L when $OD_{600}$ in the growth cultures reached 0.2.

Estimation of DHB concentration by LC-MS/MS analyses:

Culture medium was separated from the cells by centrifugation (Beckmann-Coulter Allegra 21R, Rotor Beckmann S4180, 10 min, 4800 rpm). Clear supernatant was stored at −20° C. until further analysis. DHB content was quantified using an HPLC (Waters) equipped an ACQUITY UPLC BEH column (C18, 1.7 µm, 100×2.1 mm, Waters), coupled to a mass sensitive detector (TQ, Waters, ESI mode, capillary voltage: 2.5 kV, cone voltage 25 V, Extractor voltage: 3V, source temperature: 150° C., desolvation temperature: 450° C., cone gas flow: 50 L/h, desolvation gas flow: 750 L/h). Column temperature was held at 30° C. Mobile phase was a mixture of 88% of a 0.08% tetra-n-butylammonium hydroxide solution, and 12% acetonitrile. Flow rate was fixed at 0.4 mL/min. Injection volume of the samples was 5 µL.

Results:

The DHB content of the culture medium of strain E. coli ECE1 and the control strain was estimated at 8 h and 24 h after inducing the expression of malate kinase, aspartate semialdehyde dehydrogenase, and DHB dehydrogenase by addition of IPTG. As can be seen in Table 16, the strain ECE1 which expressed the DHB pathway enzymes produced significantly higher amounts of DHB than the control strain demonstrating the possibility of the zymotic production of DHB via the metabolic pathway shown in FIG. 1 (i).

TABLE 16

DHB concentration in the culture medium of E coli ECE1 and control strain

| Time [h] | DHB concentration [mg/L] | |
|---|---|---|
| | ECE1 | control |
| 8 | 0.80 | 0 |
| 24 | 2.53 | 0.24 |

REFERENCES

Akita, O., Nishimori, C., Shimamoto, T., Fujii, T. & Iefuji, H. (2000). Transport of pyruvate in *Saccharomyces cerevisiae* and cloning of the gene encoded pyruvate permease. *Biosci Biotechnol Biochem* 64, 980-984.

Bailey, J. E. (1991). Toward a science of metabolic engineering. *Science* 252, 1668-1675.

Camarasa, C., Bidard, F., Bony, M., Barre, P. & Dequin, S. (2001). Characterization of *Schizosaccharomyces pombe* malate permease by expression in *Saccharomyces cerevisiae*. *Appl Environ Microbiol* 67, 4144-4151.

Cherepanov, P. P. & Wackernagel, W. (1995). Gene disruption in *Escherichia coli*: TcR and KmR cassettes with the option of Flp-catalyzed excision of the antibiotic-resistance determinant. *Gene* 158, 9-14.

Datsenko, K. A. & Wanner, B. L. (2000). One-step inactivation of chromosomal genes in *Escherichia coli* K-12 using PCR products. *Proc Natl Acad Sci USA* 97, 6640-6645.

Deck, P., Exner, K. & Buschhaus, B. (2008). Method for the production of D,L-hydroxy-4-alkylthio butyric acid. Edited by B. AG.

Dykxhoorn, D. M., St Pierre, R. & Linn, T. (1996). A set of compatible tac promoter expression vectors. *Gene* 177, 133-136.

Ford, G. & Ellis, E. M. (2002). Characterization of Ypr1p from *Saccharomyces cerevisiae* as a 2-methylbutyraldehyde reductase. *Yeast* 19, 1087-1096.

Grobler, J., Bauer, F., Subden, R. E. & Van Vuuren, H. J. (1995). The mae1 gene of *Schizosaccharomyces pombe* encodes a permease for malate and other C4 dicarboxylic acids. *Yeast* 11, 1485-1491.

Groeneveld, M., Weme, R. G., Duurkens, R. H. & Slotboom, D. J. (2010). Biochemical characterization of the C4-dicarboxylate transporter DctA from *Bacillus subtilis*. *J Bacteriol* 192, 2900-2907.

James, C. L. & Viola, R. E. (2002). Production and characterization of bifunctional enzymes. Domain swapping to produce new bifunctional enzymes in the aspartate pathway. *Biochemistry* 41, 3720-3725.

Jantama, K., Haupt, M. J., Svoronos, S. A., Zhang, X., Moore, J. C., Shanmugam, K. T. & Ingram, L. O. (2008a). Combining metabolic engineering and metabolic evolution to develop nonrecombinant strains of *Escherichia coli* C that produce succinate and malate. *Biotechnol Bioeng* 99, 1140-1153.

Jantama, K., Zhang, X., Moore, J. C., Shanmugam, K. T., Svoronos, S. A. & Ingram, L. O. (2008b). Eliminating side products and increasing succinate yields in engineered strains of *Escherichia coli* C. *Biotechnol Bioeng* 101, 881-893.

Keng, Y. F. & Viola, R. E. (1996). Specificity of aspartokinase III from *Escherichia coli* and an examination of important catalytic residues. *Arch Biochem Biophys* 335, 73-81.

Kockelkorn, D. & Fuchs, G. (2009). Malonic semialdehyde reductase, succinic semialdehyde reductase, and succinyl-coenzyme A reductase from *Metallosphaera sedula*: enzymes of the autotrophic 3-hydroxypropionate/4-hydroxybutyrate cycle in Sulfolobales. *J Bacteriol* 191, 6352-6362.

Larkin, M. A., Blackshields, G., Brown, N. P. & other authors (2007). Clustal W and Clustal X version 2.0. *Bioinformatics* 23, 2947-2948.

Lin, H., Bennett, G. N. & San, K. Y. (2005). Metabolic engineering of aerobic succinate production systems in *Escherichia coli* to improve process productivity and achieve the maximum theoretical succinate yield. *Metab Eng* 7, 116-127.

Marco-Marin, C., Ramon-Maiques, S., Tavarez, S. & Rubio, V. (2003). Site-directed mutagenesis of *Escherichia coli* acetylglutamate kinase and aspartokinase III probes the catalytic and substrate-binding mechanisms of these amino acid kinase family enzymes and allows three-dimensional modelling of aspartokinase. *J Mol Biol* 334, 459-476.

Millard, C. S., Chao, Y. P., Liao, J. C. & Donnelly, M. I. (1996). Enhanced production of succinic acid by overexpression of phosphoenolpyruvate carboxylase in *Escherichia coli*. *Appl Environ Microbiol* 62, 1808-1810.

Roberts, S. J., Morris, J. C., Dobson, R. C. & Gerrard, J. A. (2003). The preparation of (S)-aspartate semi-aldehyde appropriate for use in biochemical studies. *Bioorg Med Chem Lett* 13, 265-267.

Rognstad, R. & Katz, J. (1979). Effects of 2,4-dihydroxybutyrate on lipogenesis in rat hepatocytes. *J Biol Chem* 254, 11969-11972.

Sanchez, A. M., Bennett, G. N. & San, K. Y. (2005a). Novel pathway engineering design of the anaerobic central metabolic pathway in *Escherichia coli* to increase succinate yield and productivity. *Metab Eng* 7, 229-239.

Sanchez, A. M., Bennett, G. N. & San, K. Y. (2005b). Efficient succinic acid production from glucose through overexpression of pyruvate carboxylase in an *Escherichia coli* alcohol dehydrogenase and lactate dehydrogenase mutant. *Biotechnol Prog* 21, 358-365.

Sauer, U. & Eikmanns, B. J. (2005). The PEP-pyruvate-oxaloacetate node as the switch point for carbon flux distribution in bacteria. *FEMS Microbiol Rev* 29, 765-794.

Shinka, T., Inoue, Y., Ohse, M., Ito, A., Ohfu, M., Hirose, S. & Kuhara, T. (2002). Rapid and sensitive detection of urinary 4-hydroxybutyric acid and its related compounds by gas chromatography-mass spectrometry in a patient with succinic semialdehyde dehydrogenase deficiency. *J Chromatogr B Analyt Technol Biomed Life Sci* 776, 57-63.

Wang, Q., Ou, M. S., Kim, Y., Ingram, L. O. & Shanmugam, K. T. (2010). Metabolic flux control at the pyruvate node in an anaerobic *Escherichia coli* strain with an active pyruvate dehydrogenase. *Appl Environ Microbiol* 76, 2107-2114.

Werpy, T. & Petersen, G. (2004). *Top value added chemicals from biomass. Results of screening for potential candidates from sugars and synthesis gas.* Washington, D.C.: dx.doi.org/10.2172/15008859.

Zelle, R. M., de Hulster, E., van Winden, W. A. & other authors (2008). Malic acid production by *Saccharomyces cerevisiae*: engineering of pyruvate carboxylation, oxaloacetate reduction, and malate export. *Appl Environ Microbiol* 74, 2766-2777.

Zelle, R. M., Trueheart, J., Harrison, J. C., Pronk, J. T. & van Maris, A. J. (2010). Phosphoenolpyruvate carboxykinase as the sole anaplerotic enzyme in *Saccharomyces cerevisiae*. *Appl Environ Microbiol* 76, 5383-5389.

Zhang, X., Jantama, K., Moore, J. C., Jarboe, L. R., Shanmugam, K. T. & Ingram, L. O. (2009). Metabolic evolution of energy-conserving pathways for succinate production in *Escherichia coli*. *Proc Natl Acad Sci USA* 106, 20180-20185.

Zhang, X., Wang, X., Shanmugam, K. T. & Ingram, L. O. (2011). L-malate production by metabolically engineered *Escherichia coli*. *Appl Environ Microbiol* 77, 427-434.

The invention claimed is:

1. A malate kinase that transforms malate into 4-phospho-malate; the sequence of which is selected from the group consisting of SEQ ID NO: 39, 41, 43, and 45.

2. The malate kinase according to claim 1, wherein the malate kinase is set forth in SEQ ID NO: 39.

3. A method of producing 2,4-dihydroxybutyric acid (2,4-DHB), comprising:
   a first step of transforming malate into 4-phospho-malate using a malate kinase of claim 1,
   a second step of transforming 4-phospho-malate into malate-4-semialdehyde using a malate semialdehyde dehydrogenase selected from the group consisting of SEQ ID NO: 68, 54, 56, 58, 60, 62, 64, 66, and 231, and
   a third step of transforming malate-4-semialdehyde into 2,4DHB using a DHB dehydrogenase of SEQ ID NO: 81.

4. The method of claim 3, wherein the malate kinase is set forth in SEQ ID NO: 39.

5. The method according to claim 3, wherein the malate semialdehyde dehydrogenase is set forth in SEQ ID NO: 66.

6. The method of claim 3, wherein the malate semialdehyde dehydrogenase is set forth in SEQ ID NO: 68.

7. An isolated nucleic acid sequence encoding a malate kinase according to claim 1.

8. The isolated nucleic acid of claim 7, the sequence of which being selected from the group consisting of SEQ ID NO: 40, 42, and 44.

9. An expression vector comprising the nucleic acid according to claim 7.

10. A host microorganism expressing a malate kinase; wherein the host microorganism is transformed with the expression vector of claim 9.

11. The host microorganism according to claim 10, wherein the host microorganism is a bacterium, a yeast, or a fungus.

12. The host microorganism of claim 11, wherein the host microorganism is selected from the group consisting of *Escherichia coli, Saccharomyces cerevisiae, Corynebacterium glutamicum, Zygosaccharomyces rouxii*, and *Aspergillus flavus*.

13. A chimeric gene comprising at least, in the direction of transcription, functionally linked:
   a promoter regulatory sequence which is functional in a host organism,
   one or more isolated nucleic acid sequence encoding a malate kinase according to claim 1, and
   a terminator regulatory sequence which is functional in the host organism.

14. The chimeric gene of claim 13 comprising, in the direction of transcription, functionally linked:
   a promoter regulatory sequence which is functional in a host organism,
   a nucleic acid sequence encoding a malate semialdehyde dehydrogenase that transforms 4-phospho-malate into malate-4-semialdehyde, that has an enzyme that is an aspartate semialdehyde dehydrogenase, and the sequence being selected from the group consisting of SEQ ID NO: 54, 56, 58, 60, 62, 64, 66, and 231, and
   a terminator regulatory sequence that is functional in the host organism.

15. The chimeric gene of claim 14 having the sequence of SEQ ID NO: 229.

16. An expression vector comprising the chimeric gene according to claim 15.

17. A host microorganism, which is transformed with the expression vector of claim 16.

18. A process of production of 2,4-DHB comprising cultivating the host microorganism according to claim 17.

19. A method of producing 4-phospho-malate, comprising transforming malate by the maltase kinase according to claim 1.

20. A malate semialdehyde dehydrogenase that transforms 4-phospho-malate into malate-4-semialdehyde; the sequence of which is selected from the group consisting of SEQ ID NO: 54, 56, 58, 60, 62, 64, 66, and 231.

21. The malate semialdehyde dehydrogenase according to according to claim 20, wherein the malate semialdehyde dehydrogenase is set forth in SEQ ID NO: 66.

22. An isolated nucleic acid sequence encoding a malate semialdehyde dehydrogenase according to claim 20.

23. The isolated nucleic acid of claim 22, wherein the nucleic acid has a sequence selected from the group consisting of SEQ ID NO: 55, 57, 59, 61, 63, 65, and 230.

24. An expression vector comprising the nucleic acid according to claim 22.

25. A host microorganism expressing a malate semialdehyde dehydrogenase; wherein the host microorganism is transformed with the expression vector of claim 24.

26. The host microorganism according to claim 25, wherein the host microorganism is a bacterium, a yeast, or a fungus.

27. The host microorganism of claim 26, wherein the host microorganism is selected from the group consisting of *Escherichia coli, Saccharomyces cerevisiae, Corynebacterium glutamicum, Zygosaccharomyces rouxii*, and *Aspergillus flavus*.

28. A process of production of malate-4-semialdehyde comprising:
   cultivating the host microorganism according to claim 25 and expressing a malate semialdehyde dehydrogenase, and transforming 4-phospho-malate into malate-4-semialdehyde using the malate semialdehyde dehydrogenase.

29. A host microorganism, which is transformed with:
   an expression vector comprising an isolated nucleic acid sequence encoding a malate kinase that transforms malate into 4-phospho-malate, the sequence of which is selected from the group consisting of SEQ ID NO: 39, 41, 43, and 45;
   the expression vector of claim 24; and
   an expression vector comprising an isolated nucleic acid sequence encoding a DHB dehydrogenase that transforms malate-4-semialdehyde into 2,4-DHB, where the DHB dehydrogenase is set forth in SEQ ID NO: 81.

30. A process of production of 2,4-DHB comprising cultivating the host microorganism according to claim 29.

31. A method of producing malate-4-semialdehyde, comprising transforming 4-phospho-malate by the malate semialdehyde dehydrogenase according to claim 20.

32. A DHB dehydrogenase that transforms malate-4-semialdehyde into 2,4-DHB; wherein the DHB dehydrogenase is set forth in SEQ ID NO: 81.

33. An isolated nucleic acid sequence encoding DHB dehydrogenase according to claim 32.

34. The isolated nucleic acid of claim 33 the sequence of which being SEQ ID NO: 82.

35. An expression vector comprising the nucleic acid according to claim 33.

36. A host microorganism expressing a DHB dehydrogenase; wherein the host microorganism is transformed with the expression vector of claim 35.

37. The host microorganism according to claim 36, wherein the host microorganism is a bacterium, a yeast, or a fungus.

38. The host microorganism of claim 37, wherein the host microorganism is selected from the group consisting of *Escherichia coli, Saccharomyces cerevisiae, Corynebacterium glutamicum, Zygosaccharomyces rouxii*, and *Aspergillus flavus*.

39. A process of production of 2,4-DHB, comprising:
   cultivating the host microorganism according to claim 36 and expressing a DHB dehydrogenase, and
   transforming malate-4-semialdehyde into 2,4-DHB using the DHB dehydrogenase.

40. The process of production of 2,4-DHB according to claim 39, wherein the host microorganism is cultivated in a medium where malate, pyruvate, succinate, or fumarate is added.

41. The process of claim 40, wherein the culture medium further comprises another carbon source.

* * * * *